(12) United States Patent
Raisoni et al.

(10) Patent No.: US 10,772,503 B2
(45) Date of Patent: Sep. 15, 2020

(54) WIRELESS ANALYTE MONITORING

(71) Applicant: Senseonics, Incorporated, Germantown, MD (US)

(72) Inventors: Barkha Raisoni, Germantown, MD (US); David Lerner, St. Paul, MN (US); Christina Long, Falls Church, VA (US); Xiaoxiao Chen, Washington, DC (US); Todd Whitehurst, Redwood City, CA (US); Ravi Rastogi, Columbia, MD (US); Andrew Dehennis, Germantown, MD (US)

(73) Assignee: Senseonics, Incorporated, Germantown, MD (US)

(*) Notice: Subject to any disclaimer, the term of this patent is extended or adjusted under 35 U.S.C. 154(b) by 553 days.

(21) Appl. No.: 15/167,559

(22) Filed: May 27, 2016

(65) Prior Publication Data

US 2016/0345874 A1    Dec. 1, 2016

Related U.S. Application Data

(60) Provisional application No. 62/166,972, filed on May 27, 2015.

(51) Int. Cl.
*A61B 5/00* (2006.01)
*G16H 40/67* (2018.01)
(Continued)

(52) U.S. Cl.
CPC ............ *A61B 5/002* (2013.01); *A61B 5/0022* (2013.01); *A61B 5/1455* (2013.01); *A61B 5/1495* (2013.01); *A61B 5/14503* (2013.01); *A61B 5/14532* (2013.01); *A61B 5/7221* (2013.01); *A61B 5/746* (2013.01); *A61M 5/142* (2013.01); *A61M 5/1723* (2013.01); *G16H 40/67* (2018.01);
(Continued)

(58) Field of Classification Search
CPC . A61B 5/1495; A61B 5/14532; A61B 5/1455; A61B 5/002; A61B 5/7475; A61B 5/0022; A61B 5/14503; A61B 5/6898; A61B 5/7435; A61B 5/7221; A61B 5/746; A61B 2562/0219; A61M 5/142
See application file for complete search history.

(56) References Cited

U.S. PATENT DOCUMENTS

| 6,895,263 B2 | 5/2005 | Shin et al. |
| 7,920,906 B2 | 4/2011 | Goode, Jr. et al. |

(Continued)

FOREIGN PATENT DOCUMENTS

| EP | 2 335 584 A2 | 6/2011 |
| EP | 2 329 770 B1 | 9/2014 |

(Continued)

*Primary Examiner* — Lisa E Peters
(74) *Attorney, Agent, or Firm* — Rothwell, Figg, Ernst & Manbeck, P.C.

(57) ABSTRACT

A computing device receives analyte data produced by an analyte monitoring sensor over a communications link from at least one first device. Health data, comprising at least part of the analyte data, may be communicated over a communications link to at least one second device in response to a request. The first device may be positioned over the analyte monitoring sensor using signal strength and location information. External analyte data may be employed to calibrate the analyte monitoring sensor.

78 Claims, 23 Drawing Sheets

(51) Int. Cl.
*A61B 5/145* (2006.01)
*A61B 5/1455* (2006.01)
*A61B 5/1495* (2006.01)
*A61M 5/172* (2006.01)
*A61M 5/142* (2006.01)

(52) U.S. Cl.
CPC ............ *A61B 5/6898* (2013.01); *A61B 5/749* (2013.01); *A61B 5/7435* (2013.01); *A61B 5/7475* (2013.01); *A61B 5/7495* (2013.01); *A61B 2562/0219* (2013.01)

(56) References Cited

U.S. PATENT DOCUMENTS

| | | | |
|---|---|---|---|
| 8,394,021 B2 | 3/2013 | Goode et al. | |
| 8,731,630 B2 | 5/2014 | Kamath et al. | |
| 2005/0027180 A1 | 2/2005 | Goode, Jr. et al. | |
| 2007/0020181 A1* | 1/2007 | Workman | A61B 5/14532 424/9.1 |
| 2008/0033254 A1 | 2/2008 | Kamath et al. | |
| 2008/0288180 A1* | 11/2008 | Hayter | A61B 5/0008 702/23 |
| 2009/0036760 A1 | 2/2009 | Hayter | |
| 2009/0055149 A1* | 2/2009 | Hayter | A61B 5/14532 703/11 |
| 2009/0085768 A1* | 4/2009 | Patel | A61B 5/14532 340/870.05 |
| 2009/0208734 A1* | 8/2009 | MacFie | G01N 27/3272 428/332 |
| 2009/0247857 A1* | 10/2009 | Harper | A61B 5/14532 600/365 |
| 2010/0094112 A1* | 4/2010 | Heller | A61B 5/14532 600/345 |
| 2010/0234710 A1* | 9/2010 | Budiman | A61B 5/14532 600/365 |
| 2010/0280782 A1* | 11/2010 | Harper | A61B 5/14532 702/104 |
| 2011/0029269 A1* | 2/2011 | Hayter | A61B 5/14532 702/104 |
| 2011/0144616 A1* | 6/2011 | Michaud | A61M 5/172 604/500 |
| 2011/0184268 A1* | 7/2011 | Taub | A61B 5/14532 600/365 |
| 2011/0287528 A1* | 11/2011 | Fern | A61B 6/14532 435/287.1 |
| 2011/0320130 A1* | 12/2011 | Valdes | G06F 19/3418 702/19 |
| 2012/0108931 A1* | 5/2012 | Taub | A61B 5/14532 600/347 |
| 2012/0130209 A1 | 5/2012 | Bunge | |
| 2012/0172691 A1* | 7/2012 | Brauker | A61B 5/14532 600/347 |
| 2012/0197576 A1* | 8/2012 | Feldman | A61B 5/14532 702/104 |
| 2012/0232520 A1* | 9/2012 | Sloan | A61B 5/14532 604/504 |
| 2014/0060145 A1* | 3/2014 | Hoss | G01N 33/48792 73/1.03 |
| 2014/0082607 A1* | 3/2014 | Bernstein | G06F 11/0751 717/174 |
| 2016/0091450 A1* | 3/2016 | McColl | G01N 27/3272 205/777.5 |

FOREIGN PATENT DOCUMENTS

| | | |
|---|---|---|
| WO | 03/094714 A1 | 11/2003 |
| WO | 2014/052136 A1 | 4/2014 |

* cited by examiner

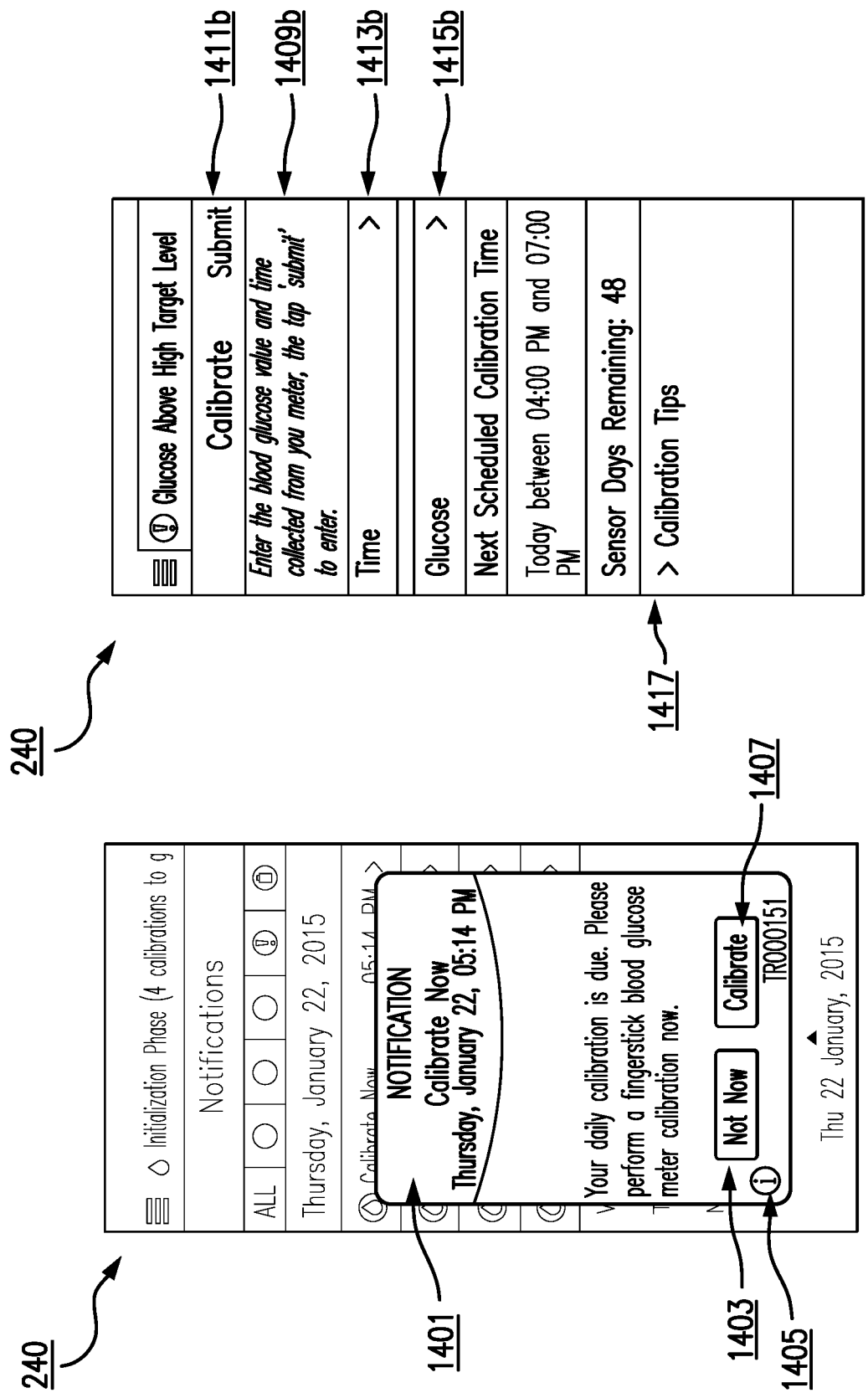

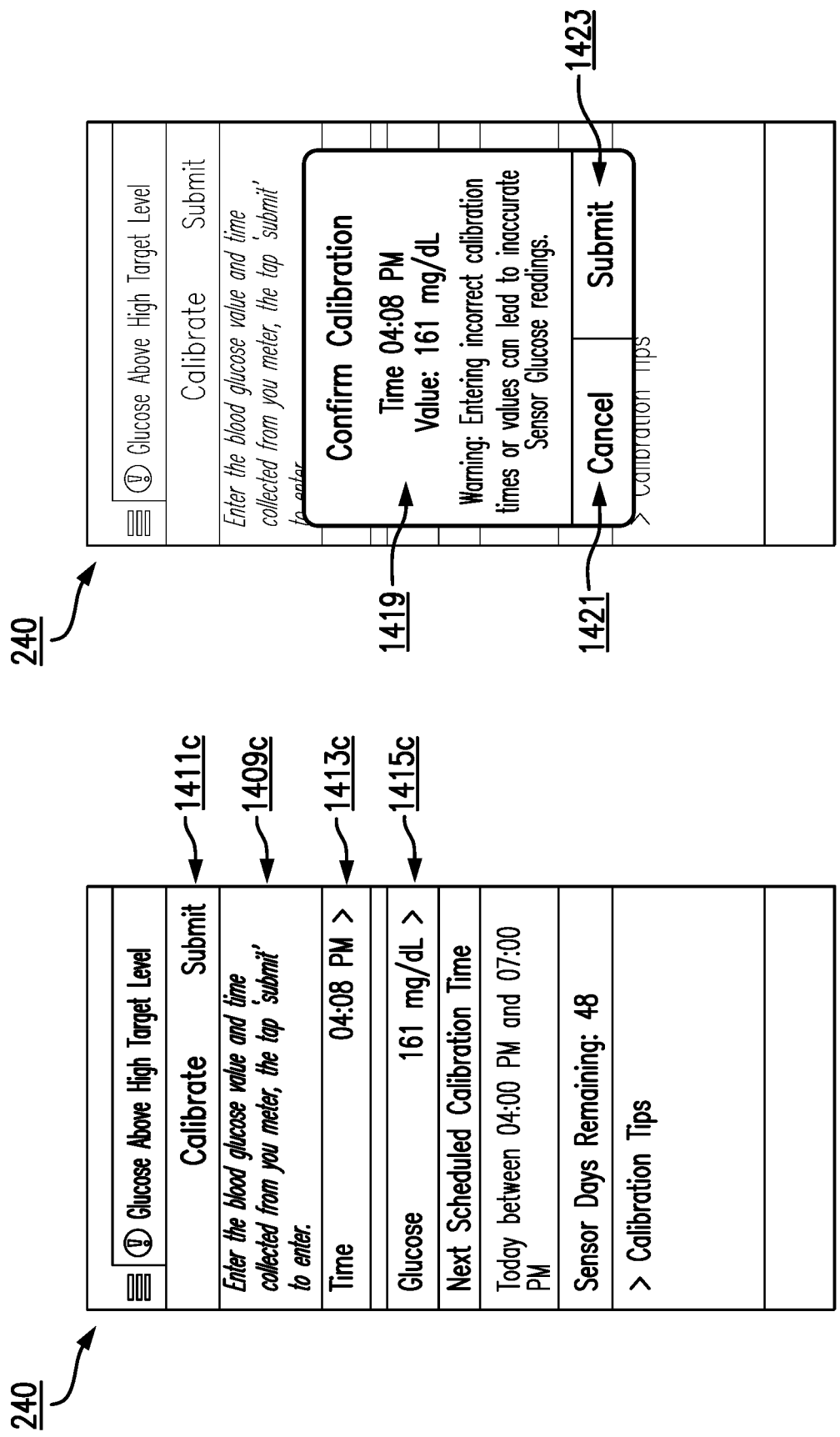

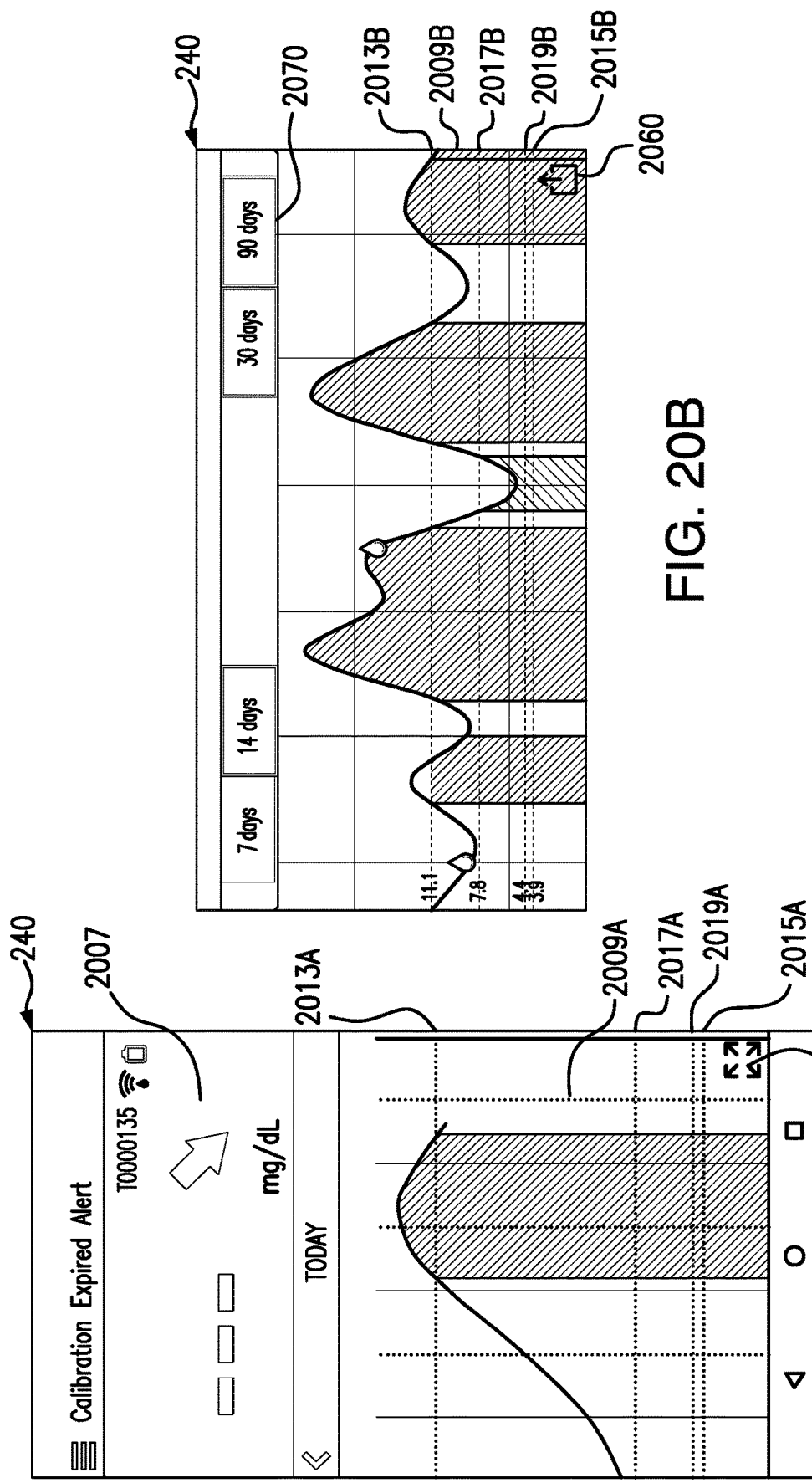

WIRELESS ANALYTE MONITORING

CROSS REFERENCE TO RELATED APPLICATIONS

This application claims priority from U.S. provisional patent application Ser. No. 62/166,972, filed May 27, 2015, which is incorporated by reference herein in its entirety.

BACKGROUND

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels <7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations comprising, but not limited to: sensor positioning, calibration, and data sharing using one or more devices in communication with the sensor(s).

SUMMARY OF THE INVENTION

The present invention overcomes the disadvantages of prior systems by providing, among other advantages, an improved analyte monitoring system having improved communication and/or user interface capabilities.

One aspect of the invention may provide a method comprising: obtaining, by an analyte monitoring device, analyte data; obtaining, by the analyte monitoring device, a plurality of information items, the plurality of information items comprising: a high analyte alarm level, a low analyte alarm level, an analyte high target level, and an analyte low target level; and, displaying, on a display device electronically coupled to the analyte monitoring device, one or more interactive graphical control elements comprising the plurality of information items and the analyte data.

In some embodiments, one of the one or more interactive graphical control elements comprises an analyte trend graph, the trend graph comprising a plurality of analyte levels over a first time interval, wherein the trend graph comprises one or more of a line graph, a pie chart, log book, or modal day.

In some embodiments, the method may further comprise: displaying, on the display device, a single-tap electronic communication icon, wherein in response to receiving a selection of the icon the analyte monitoring device transmits the analyte trend graph in an electronic communication.

In some embodiments, the method may further comprise the steps of: receiving, by the analyte monitoring device, a command; and, in response to receiving the command, displaying on the display device a plurality of analyte levels over a second time interval different than the first time interval. In some embodiments, the command comprises one of: an entry of the second time interval or a gesture.

In some embodiments, the method may further comprise: displaying an area of the trend graph below each of the plurality of analyte values as a first color when a corresponding analyte value is outside of the high analyte alarm level and low analyte alarm level, displaying the area of the trend graph below each of the plurality of analyte values as a second color when a corresponding analyte value is between the high analyte target level and the low analyte target level, and displaying the area of the trend graph below each of the plurality of analyte values as a third color when a corresponding analyte value is either between the high analyte target level and the high analyte alarm level or between the low analyte target level and the low analyte alarm level, wherein the first, second, and third colors are different colors.

In some embodiments, one or more interactive graphical control elements may further comprise one or more selectable event icons, wherein displaying the one or more interactive graphical control elements comprises, in response to a selection of one of the one or more selectable event icons, displaying, on the display device electronically coupled to the analyte monitoring device, a window with information about the selected event icon.

In some embodiments, the method may further comprise displaying each of the high analyte alarm level, the low analyte alarm level, the analyte high target level, and the analyte low target level in the one or more graphical control elements as a line. In some embodiments, the lines for each of the high analyte alarm level and the low analyte alarm level are a first color, and the lines for the analyte high target level and the analyte low target level are a second color different from the first color.

In some embodiments, the analyte high target level and the analyte low target level are associated with a first user profile. In some embodiments, the method further comprises: receiving, by the analyte monitoring device, a command; and, in response to receiving the command, displaying on the display the analyte target level and the analyte low target level associated with a second user profile different from the first user profile.

Another aspect of the invention may provide a method comprising: obtaining, by an analyte monitoring device, a plurality of information items, the plurality of information items comprising: a high analyte alarm level, a low analyte alarm level, an analyte high target level, an analyte low target level, a current analyte level, a connection status, a trend arrow, a trend graph, and a profile; and, simultaneously displaying, on a display device electronically coupled to the analyte monitoring device, one or more interactive graphical control elements and the plurality of information items.

In some embodiments, the method may further comprise: receiving, by the analyte monitoring device, a command; and, in response to receiving the command, output an auditory reading of one or more of the information items.

In some embodiments, the informational items may further comprise one or more notifications, alarms, or alerts.

Another aspect of the invention may provide a method comprising: obtaining, by an analyte monitoring device, a plurality of information items, the plurality of information items comprising one or more of a plurality of events; and, simultaneously displaying, on a display device electronically coupled to the analyte monitoring device, one or more interactive graphical control elements and the plurality of information items, wherein the one or more graphical control elements comprise an event log, the event log comprising the plurality of events and a selectable icon associated with each of the events.

In some embodiments, the method may further comprise: receiving, by the analyte monitoring device, a selection of one of the selectable icons; and, in response to receiving the selection, displaying a window with details of an event associated with the selected icon.

In some embodiments, the selectable icon associated with each of the plurality of events comprises one or more of: a blood glucose meter test icon, a meal event icon, an insulin dosage icon, a health condition icon, an exercise event icon, and a calibration measurement icon.

In some embodiments, one or more interactive graphical control elements comprise one or more selectable filtering options, wherein each selectable filtering option corresponds to one or more event types.

In some embodiments, the method further comprises: receiving, by the analyte monitoring device, a selection of one of the selectable filtering options; and, in response to receiving the selection, displaying in the event log only a set of events from the plurality of events that correspond to an event type associated with the selected filtering option.

Another aspect of the invention may provide a method comprising: obtaining, by an analyte monitoring device, a plurality of information items, the plurality of information items comprising one or more alarms, events, and notifications; and, simultaneously displaying, on a display device electronically coupled to the analyte monitoring device, one or more interactive graphical control elements and the plurality of information items, wherein the one or more graphical control elements comprise a list, the list comprising the one or more alarms, events, and notifications and a selectable icon associated with each of the one or more alarms, events, and notifications.

In some embodiments, the method further comprises: receiving, by the analyte monitoring device, a selection of one of the selectable icons; and, in response to receiving the selection, displaying a window with one or more recommended actions associated with the selected icon.

In some embodiments, the selectable icon associated with each of the one or more alerts, alarms, and notifications comprises an indication of one or more of type, severity, and frequency, wherein the type comprises one or more of: low glucose, out of range low glucose, high glucose, out of range high glucose, calibration past due, calibration expired, battery empty, sensor replacement, high ambient light, high temperature, low temperature, error, sensor instability, predicted low glucose, predicted high glucose, rate falling, rate rising, calibrate now, charge battery, new sensor detected, sensor days, invalid time, temporary profile duration ended, and basil rate testing, the severity comprises one or more of: critical, non-critical, and, the frequency comprises one or more than one.

In some embodiments, the one or more interactive graphical control elements comprise one or more selectable filtering options, wherein each selectable filtering option corresponds to one or more of type, severity, or frequency.

In some embodiments, the method further comprises: receiving, by the analyte monitoring device, a selection of one of the selectable filtering options; and, in response to receiving the selection, displaying in the list only a set of alerts, alarms, and notifications from the one or more alerts, alarms, and notifications that correspond to one or more of a type, frequency, or severity associated with the selected filtering option.

Another aspect of the invention may provide a non-transitory tangible computer readable medium comprising computer readable instructions configured to cause one or more processors in an analyte monitoring device to perform a process comprising: obtaining, by the analyte monitoring device, analyte data; obtaining, by the analyte monitoring device, a plurality of information items, the plurality of information items comprising: a high analyte alarm level, a low analyte alarm level, an analyte high target level, and an analyte low target level; and, displaying, on a display device electronically coupled to the analyte monitoring device, one or more interactive graphical control elements comprising the plurality of information items and the analyte data.

Another aspect of the invention may provide a non-transitory tangible computer readable medium comprising computer readable instructions configured to cause one or more processors in an analyte monitoring device to perform a process comprising: obtaining, by the analyte monitoring device, a plurality of information items, the plurality of information items comprising: a high analyte alarm level, a low analyte alarm level, an analyte high target level, an analyte low target level, a current analyte level, a connection status, a trend arrow, a trend graph, and a profile; and, simultaneously displaying, on a display device electronically coupled to the analyte monitoring device, one or more interactive graphical control elements and the plurality of information items.

Another aspect of the invention may provide a non-transitory tangible computer readable medium comprising computer readable instructions configured to cause one or more processors in an analyte monitoring device to perform a process comprising: obtaining, by the analyte monitoring device, a plurality of information items, the plurality of information items comprising one or more of a plurality of events; and, simultaneously displaying, on a display device electronically coupled to the analyte monitoring device, one or more interactive graphical control elements and the plurality of information items, wherein the one or more graphical control elements comprise an event log, the event log comprising the plurality of events and a selectable icon associated with each of the events.

Another aspect of the invention may comprise a non-transitory tangible computer readable medium comprising computer readable instructions configured to cause one or more processors in an analyte monitoring device to perform a process comprising: obtaining, by the analyte monitoring device, a plurality of information items, the plurality of information items comprising one or more alarms, events, and notifications; and, simultaneously displaying, on a display device electronically coupled to the analyte monitoring device, one or more interactive graphical control elements and the plurality of information items, wherein the one or more graphical control elements comprise a list, the list comprising the one or more alarms, events, and notifications and a selectable icon associated with each of the one or more alarms, events, and notifications.

Another aspect of the invention may provide an analyte monitoring device comprising: one or more processors; and a non-transitory tangible computer readable medium comprising computer readable instruction configured to cause the one or more processors to perform a process comprising: obtaining, by the analyte monitoring device, analyte data; obtaining, by the analyte monitoring device, a plurality of information items, the plurality of information items comprising: a high analyte alarm level, a low analyte alarm level, an analyte high target level, and an analyte low target level; and, displaying, on a display device electronically coupled to the analyte monitoring device, one or more interactive graphical control elements comprising the plurality of information items and the analyte data.

Another aspect of the invention may provide an analyte monitoring device comprising: one or more processors; and a non-transitory tangible computer readable medium comprising computer readable instruction configured to cause the one or more processors to perform a process comprising: obtaining, by the analyte monitoring device, a plurality of information items, the plurality of information items comprising: a high analyte alarm level, a low analyte alarm level, an analyte high target level, an analyte low target level, a current analyte level, a connection status, a trend arrow, a trend graph, and a profile; and, simultaneously displaying, on a display device electronically coupled to the analyte monitoring device, one or more interactive graphical control elements and the plurality of information items.

Another aspect of the invention may provide an analyte monitoring device comprising: one or more processors; and a non-transitory tangible computer readable medium comprising computer readable instruction configured to cause the one or more processors to perform a process comprising: obtaining, by the analyte monitoring device, a plurality of information items, the plurality of information items comprising: a high analyte alarm level, a low analyte alarm level, an analyte high target level, an analyte low target level, a current analyte level, a connection status, a trend arrow, a trend graph, and a profile; and, simultaneously displaying, on a display device electronically coupled to the analyte monitoring device, one or more interactive graphical control elements and the plurality of information items.

Another aspect of the invention may provide an analyte monitoring device comprising: one or more processors; and a non-transitory tangible computer readable medium comprising computer readable instruction configured to cause the one or more processors to perform a process comprising: obtaining, by the analyte monitoring device, a plurality of information items, the plurality of information items comprising one or more alarms, events, and notifications; and, simultaneously displaying, on a display device electronically coupled to the analyte monitoring device, one or more interactive graphical control elements and the plurality of information items, wherein the one or more graphical control elements comprise a list, the list comprising the one or more alarms, events, and notifications and a selectable icon associated with each of the one or more alarms, events, and notifications.

Another aspect of the invention may provide a non-transitory tangible computer readable medium comprising computer readable instructions configured to cause one or more processors in an analyte monitoring device to: receive analyte data based on measurements obtained from an analyte monitoring sensor, wherein the analyte data is received over a communications link from at least one first device; store the analyte data in a memory; receive a request for health data over a communications link from at least one second device, the requested health data comprising at least part of the analyte data; and transmit the requested health data to the at least one second device over a second communications link.

In some embodiments, the analyte monitoring sensor is a wireless analyte monitoring sensor.

In some embodiments, the computer readable instructions are configured to cause the one or more processors in the analyte monitoring device to receive the analyte data wirelessly.

In some embodiments, the computer readable instructions are configured to cause the one or more processors in the analyte monitoring device to receive a request to enable a setting to share the stored analyte data.

In some embodiments, transmit the requested health data further comprises transmit the requested health data as one or more of: a simple mail transfer protocol (SMTP) message, an enhanced messaging service (EMS) message, or a telephonic message.

In some embodiments, the at least one second device is associated with a member, the member comprising one or more of: caregiver, physician, and family member.

In some embodiments, at least one of the at least one first device is one of: an analyte monitoring device, an intermediary device, or one of the at least one second device.

In some embodiments, at least one of the at least one second device is one of: a mobile device, a peer device, a blood glucose meter, and an insulin pump.

In some embodiments, at least one of the at least one second device comprises a mobile medical application.

In some embodiments, at least part of the second communications link communicates over one or more of: a cellular network, a wired network, the Internet, an Intranet, Wi-Fi, Bluetooth, Near-Field Communications (NFC), and infrared.

In some embodiments, the computer readable instructions are configured to cause the one or more processors in the analyte monitoring device to communicate at least part of the analyte data over a communications link to a plurality of devices.

In some embodiments, the request is a synchronization request.

In some embodiments, the health data comprises at least one of the following: food data; exercise data; well-being data; fitness data; medicine data; trend data; notification data; reminder data; scheduling data; sleep data; alert data; settings; preferences; calibration data; and device health.

Another aspect of the invention may provide a process performed by an analyte monitoring device comprising: receiving analyte data based on measurements obtained from an analyte monitoring sensor, wherein the analyte data is received over a communications link from at least one first device; storing the analyte data in a memory; receiving a request for health data over a communications link from at least one second device, the requested health data comprising at least part of the analyte data; and transmitting the requested health data to the at least one second device over a second communications link.

In some embodiments, the analyte monitoring sensor is a wireless analyte monitoring sensor.

In some embodiments, receiving the analyte data comprises receiving the analyte data wirelessly.

In some embodiments, the process further comprises receiving a request to enable a setting to share the stored analyte data.

In some embodiments, transmitting the requested health data further comprises transmitting the requested health data as one or more of: a simple mail transfer protocol (SMTP) message, an enhanced messaging service (EMS) message, or a telephonic message.

In some embodiments, the at least one second device is associated with a member, the member comprising one or more of: caregiver, physician, and family member.

In some embodiments, at least one of the at least one first device is one of: the analyte monitoring device, an intermediary device, or one of the at least one second device.

In some embodiments, at least one of the at least one second device is one of: a mobile device, a peer device, a blood glucose meter, and an insulin pump.

In some embodiments, at least one of the at least one second device comprises a mobile medical application.

In some embodiments, at least part of the second communications link communicates over one or more of: a cellular network, a wired network, the Internet, an Intranet, Wi-Fi, Bluetooth, Near-Field Communications (NFC), and infrared.

In some embodiments, the process further comprises communicating at least part of the analyte data over a communications link to a plurality of devices.

In some embodiments, the request is a synchronization request.

In some embodiments, the health data comprises at least one of the following: food data; exercise data; well-being data; fitness data; medicine data; trend data; notification data; reminder data; scheduling data; sleep data; alert data; settings; preferences; calibration data; and device health.

Another aspect of the invention may provide an analyte monitoring device comprising: one or more processors; a first communications interface; a second communications interface; a memory; and a non-transitory tangible computer readable medium comprising computer readable instructions configured to cause the one or more processors to perform a process comprising: receiving analyte data based on measurements obtained from an analyte monitoring sensor, wherein the analyte data is received over the first communications interface from at least one first device; storing the analyte data in the memory; receiving a request for health data over the second communications interface from at least one second device, the requested health data comprising at least part of the analyte data; and transmitting the requested health data to the at least one second device over a second communications interface.

In some embodiments, the analyte monitoring sensor is a wireless analyte monitoring sensor.

In some embodiments, the first and second communications interfaces are wireless communications interfaces.

In some embodiments, the computer readable instructions are further configured to cause the one or more processors to receive a request to enable a setting to share the stored analyte data.

In some embodiments, the transmitting the requested health data further comprises transmitting the requested health data as one or more of: a simple mail transfer protocol (SMTP) message, an enhanced messaging service (EMS) message, or a telephonic message.

In some embodiments, the at least one second device is associated with a member, the member comprising one or more of: caregiver, physician, and family member.

In some embodiments, at least one of the at least one first device is the analyte monitoring device.

In some embodiments, at least one of the at least one first device is one of: an intermediary device or one of the at least one second device.

In some embodiments, at least one of the at least one second device is one of: a mobile device, a peer device, a blood glucose meter, or an insulin pump.

In some embodiments, wherein at least one of the at least one second device comprises a mobile medical application.

In some embodiments, at least part of the second communications interface is configured to communicate with one or more of: a cellular network, a wired network, the Internet, an Intranet, Wi-Fi, Bluetooth, Near-Field communication (NFC), and infrared.

In some embodiments, the instructions are further configured to cause the one or more processors to communicate at least part of the analyte data over at least one of the first communications interface and second communications interface to a plurality of devices.

In some embodiments, the request is a synchronization request. In some embodiments, the health data comprises at least one of the following: food data; exercise data; well-being data; fitness data; medicine data; trend data; notification data; reminder data; scheduling data; sleep data; alert data; settings; preferences; calibration data; and device health.

Another aspect of the invention may provide a non-transitory tangible computer readable medium comprising computer readable instructions configured to cause one or more processors in an analyte monitoring device to perform a process comprising: receiving first analyte data based on measurements obtained from an analyte monitoring sensor over a communications link from at least one first device, the first analyte data representing first analyte information for a first living being; determining whether calibration is appropriate; and, in response to determining that calibration is appropriate, configuring a graphical user interface on a display of the analyte monitoring device to allow an entry of second analyte data representing second analyte information for the first living being, or in response to determining that calibration is not appropriate, configuring the graphical user interface element on the display of the analyte monitoring device to prevent the entry of the second analyte data.

In some embodiments, the analyte monitoring sensor is a wireless analyte monitoring sensor.

In some embodiments, the computer readable instructions are configured to cause the one or more processors in the analyte monitoring device to receive the first analyte data wirelessly. In some embodiments, the computer readable instructions are configured to cause the one or more processors in the analyte monitoring device to perform a process further comprising: receiving the second analyte data; and, transmitting the second analyte data over the first communications link to the first device.

In some embodiments, the receiving first analyte data further comprises accepting manual data input via the graphical user interface.

In some embodiments, the receiving first analyte data further comprises accepting manual data input via the graphical user interface employing at least one of the following: a scroll selector; a keypad entry; a suggested values list; an icon; a location on a graphic; a voice entry system; a scanner; and an image.

In some embodiments, the communications link comprises at least one of the following: Wi-Fi; Bluetooth; Induction; and Near-Field Communications (NFC).

In some embodiments, determining whether calibration is appropriate further comprises: determining a first quality factor for the first analyte data; determining a second quality factor for the second analyte data; and determining whether both the first quality factor and the second quality factor exceed a threshold.

In some embodiments, the determining at least one of the first quality factor and the second quality factor further comprises determining the rate of change with respect to earlier analyte data measurements.

In some embodiments, the determining at least one of the first quality factor and the second quality factor further comprises accounting for the time of the last calibration.

In some embodiments, the determining at least one of the first quality factor and the second quality factor further comprises accounting for the amount of analyte data collected.

In some embodiments, the determining at least one of the first quality factor and the second quality factor further comprises verifying that the first analyte data falls within an operating range.

In some embodiments, the determining at least one of the first quality factor and the second quality factor further comprises accounting for the operating conditions when the analyte data was collected.

In some embodiments, the determining at least one of the first quality factor and the second quality factor further comprises accounting for statistical changes from previous measurements.

In some embodiments, the receiving second analyte data comprises receiving second analyte data collected from at least one blood glucose meter or finger-stick blood glucose test.

In some embodiments, the analyte monitoring device comprises a communication interface comprising at least one of the following: a touch screen; a voice interface; a multimedia interface; an audio interface; a tactile interface; and a visual interface.

In some embodiments, the analyte monitoring device comprises at least one of the following: a mobile device; a smart phone; a tablet; a PC; and a netbook.

In some embodiments, at least one of the at least one first device is one of: the analyte monitoring sensor, an intermediary device, a data repeating device.

In some embodiments, the analyte monitoring sensor comprises a fluorometer.

In some embodiments, in response to determining that calibration is appropriate, the computer readable instructions are further configured to cause the one or more processors in the analyte monitoring device to display one or more notifications, the one or more notifications comprising one or more information items, the information items comprising one or more of: a next scheduled calibration time, a number of calibrations completed, and a calibration phase.

In some embodiments, the calibration phase comprises one of a daily calibration phase or an initialization calibration phase.

Another aspect of the invention may provide a process performed by an analyte monitoring device, the process comprising: receiving first analyte data based on measurements obtained from an analyte monitoring sensor over a communications link from at least one first device, the first analyte data representing first analyte information for a first living being; determining whether calibration is appropriate; and, in response to determining that calibration is appropriate, configuring a graphical user interface on a display of the analyte monitoring device to allow an entry of second analyte data representing second analyte information for the first living being, or in response to determining that calibration is not appropriate, configuring the graphical user interface element on the display of the analyte monitoring device to prevent the entry of the second analyte data.

In some embodiments, the analyte monitoring sensor is a wireless analyte monitoring sensor.

In some embodiments, receiving the first analyte data comprises receiving the first analyte data wirelessly.

In some embodiments, the process further comprises: receiving the second analyte data; and, transmitting the second analyte data over the communications link to the first device.

In some embodiments, the receiving first analyte data further comprises accepting manual data input via the graphical user interface.

In some embodiments, the receiving first analyte data further comprises accepting manual data input via the graphical user interface employing at least one of the following: a scroll selector; a keypad entry; a suggested values list; an icon; a location on a graphic; a voice entry system; a scanner; and an image.

In some embodiments, the communications link comprises at least one of the following: Wi-Fi; Bluetooth; Induction; and Near-Field Communications (NFC).

In some embodiments, determining whether calibration is appropriate further comprises: determining a first quality factor for the first analyte data; determining a second quality factor for the second analyte data; and determining whether both the first quality factor and the second quality factor exceed a threshold.

In some embodiments, the determining at least one of the first quality factor and the second quality factor further comprises determining the rate of change with respect to earlier analyte data measurements.

In some embodiments, the determining at least one of the first quality factor and the second quality factor further comprises accounting for the time of the last calibration.

In some embodiments, the determining at least one of the first quality factor and the second quality factor further comprises accounting for the amount of analyte data collected.

In some embodiments, the determining at least one of the first quality factor and the second quality factor further comprises verifying that the first analyte data falls within an operating range.

In some embodiments, the determining at least one of the first quality factor and the second quality factor further comprises accounting for the operating conditions when the analyte data was collected.

In some embodiments, the determining at least one of the first quality factor and the second quality factor further comprises accounting for statistical changes from previous measurements.

In some embodiments, the receiving second analyte data comprises receiving second analyte data collected from at least one blood glucose meter or finger-stick blood glucose test. In some embodiments, the analyte monitoring device comprises a communication interface comprising at least one of the following: a touch screen; a voice interface; a multimedia interface; an audio interface; a tactile interface; and a visual interface.

In some embodiments, the analyte monitoring device comprises at least one of the following: a mobile device; a smart phone; a tablet; a PC; and a netbook.

In some embodiments, at least one of the at least one first device is one of: the analyte monitoring sensor, an intermediary device, a data repeating device.

In some embodiments, the analyte monitoring sensor comprises a fluorometer.

In some embodiments, in response to determining that calibration is appropriate, the process further comprises configuring the graphical user interface to display one or more notifications, the one or more notifications comprising one or more information items, the information items comprising one or more of: a next scheduled calibration time, a number of calibrations completed, and a calibration phase.

In some embodiments, the calibration phase comprises one of a daily calibration phase or an initialization calibration phase.

Another aspect of the invention may provide an analyte monitoring device comprising: one or more processors; a communications interface; and a non-transitory tangible computer readable medium comprising computer readable instruction configured to cause the one or more processors to perform a process comprising: receiving first analyte data based on measurements obtained from an analyte monitoring sensor over the communications interface from at least one first device, the first analyte data representing first analyte information for a first living being; determining whether calibration is appropriate; and, in response to determining that calibration is appropriate, configuring a graphical user interface on a display of the analyte monitoring device to allow an entry of second analyte data representing second analyte information for the first living being, or in response to determining that calibration is not appropriate, configuring the graphical user interface element on the display of the analyte monitoring device to prevent the entry of the second analyte data.

In some embodiments, the analyte monitoring sensor is a wireless analyte monitoring sensor.

In some embodiments, the communications interface is wireless communications interfaces.

In some embodiments, the process further comprises: receiving the second analyte data; and, transmitting the second analyte data over the communications link to the first device.

In some embodiments, the receiving first analyte data further comprises accepting manual data input via the graphical user interface.

In some embodiments, the receiving first analyte data further comprises accepting manual data input via the graphical user interface employing at least one of the following: a scroll selector; a keypad entry; a suggested values list; an icon; a location on a graphic; a voice entry system; a scanner; and an image.

In some embodiments, the first analyte data and second analyte data each comprises at least one of the following: glucose data; sugar data; oxygen data; antibodies data; temperature data; cell counts data; and ph. data. In some embodiments, the communications link comprises at least one of the following: Wi-Fi; Bluetooth; Induction; and Near-Field Communications (NFC).

In some embodiments, determining whether calibration is appropriate further comprises: determining a first quality factor for the first analyte data; determining a second quality factor for the second analyte data; and determining whether both the first quality factor and the second quality factor exceed a threshold. In some embodiments, the determining at least one of the first quality factor and the second quality factor further comprises determining the rate of change with respect to earlier analyte data measurements.

In some embodiments, the determining at least one of the first quality factor and the second quality factor further comprises accounting for the time of the last calibration.

In some embodiments, the determining at least one of the first quality factor and the second quality factor further comprises accounting for the amount of analyte data collected.

In some embodiments, the determining at least one of the first quality factor and the second quality factor further comprises verifying that the first analyte data falls within an operating range.

In some embodiments, the determining at least one of the first quality factor and the second quality factor further comprises accounting for the operating conditions when the analyte data was collected.

In some embodiments, the determining at least one of the first quality factor and the second quality factor further comprises accounting for statistical changes from previous measurements.

In some embodiments, the receiving second analyte data comprises receiving second analyte data collected from at least one blood glucose meter or finger-stick blood glucose test.

In some embodiments, the analyte monitoring device comprises a communication interface comprising at least one of the following: a touch screen; a voice interface; a multimedia interface; an audio interface; a tactile interface; and a visual interface.

In some embodiments, the analyte monitoring device comprises at least one of the following: a mobile device; a smart phone; a tablet; a PC; and a netbook.

In some embodiments, at least one of the at least one first device is one of: the wireless analyte monitoring sensor, an intermediary device, a data repeating device.

In some embodiments, the wireless analyte monitoring sensor comprises a fluorometer.

In some embodiments, in response to determining that calibration is appropriate, the process further comprises displaying one or more notifications, the one or more notifications comprising one or more information items, the information items comprising one or more of: a next scheduled calibration time, a number of calibrations completed, and a calibration phase.

In some embodiments, the calibration phase comprises one of a daily calibration phase or an initialization calibration phase.

Another aspect of the invention may provide a non-transitory tangible computer readable medium comprising computer readable instruction configured to cause one or more processors in an analyte monitoring device to: receive an electronic communication from a wireless transceiver, the electronic communication comprising information on wireless signal of a first communications link between the wireless transceiver and a wireless analyte monitoring sensor; determine a real-time signal strength for the wireless signal in response to receiving the electronic communication; and display the signal strength on a graphical user interface of a display coupled to the analyte monitoring device.

In some embodiments, the display comprises a touch screen.

In some embodiments, the computer readable instruction is further configured to cause the one or more processors in the analyte monitoring device to provide a suggested movement of the wireless transceiver.

In some embodiments, the wireless analyte monitoring sensor comprises a wireless glucose monitoring sensor.

In some embodiments, the wireless analyte monitoring sensor is configured to be implanted subcutaneously.

In some embodiments, the wireless transceiver is integrated with the analyte monitoring device.

In some embodiments, the wireless transceiver comprises a near field communication transceiver.

In some embodiments, the wireless transceiver is configured to provide power to the wireless analyte monitoring sensor.

In some embodiments, the electronic communication is transmitted by the wireless transceiver to the analyte monitoring device via one of: a cellular link, a Wi-Fi link, a wired-link.

In some embodiments, the analyte monitoring device comprises one of: a mobile device, a medical device, or a computer.

In some embodiments, the computer readable instruction is further configured to cause the one or more processors in the analyte monitoring device to track the relative position of the wireless transceiver.

In some embodiments, the computer readable instruction is further configured to cause the one or more processors in the analyte monitoring device to track the relative position of the wireless transceiver using an accelerometer.

In some embodiments, the computer readable instruction is further configured to cause the one or more processors in the analyte monitoring device to track the signal strength with respect to the relative position of the wireless transceiver to the wireless analyte monitoring sensor.

In some embodiments, the computer readable instruction is further configured to cause the one or more processors in the analyte monitoring device to track the signal strength with respect to the position of the wireless transceiver.

In some embodiments, the computer readable instruction is further configured to cause the one or more processors in the analyte monitoring device to track the signal strength with respect to the position of the wireless analyte monitoring sensor.

In some embodiments, the computer readable instruction is further configured to cause the one or more processors in the analyte monitoring device to display suggested movements of the wireless transceiver to increase signal strength.

In some embodiments, the computer readable instruction is further configured to cause the one or more processors in the analyte monitoring device to display suggested movements of the wireless transceiver to maximize the signal strength.

In some embodiments, the computer readable instruction is further configured to cause the one or more processors in the analyte monitoring device to display suggested movements of the wireless transceiver to obtain a signal strength that exceeds a threshold.

In some embodiments, the computer readable instruction is further configured to cause the one or more processors in the analyte monitoring device to display instructions for adhering the wireless transceiver to a location having a signal strength that exceeds a threshold.

In some embodiments, the location is external to the body part containing the wireless analyte monitoring sensor.

In some embodiments, the location is on the surface of a body part containing the wireless analyte monitoring sensor.

In some embodiments, the computer readable instruction is further configured to cause the one or more processors in the analyte monitoring device to locate the wireless analyte monitoring sensor for extraction.

In some embodiments, the wireless analyte monitoring sensor comprises a fluorometer.

In some embodiments, the computer readable instruction is further configured to cause the one or more processors in the analyte monitoring device to provide a suggested movement of the wireless analyte monitoring sensor.

In some embodiments, the suggested movement comprises a depth.

In some embodiments, the suggested movement comprises a lateral movement.

Another aspect of the invention may provide a process performed by an analyte monitoring device, the process comprising: receiving an electronic communication from a wireless transceiver, the electronic communication comprising information on a wireless signal of a first communications link between the wireless transceiver and a wireless analyte monitoring sensor; determining a real-time signal strength for the wireless signal in response to receiving the electronic communication; and displaying the signal strength on a graphical user interface of a display coupled to the analyte monitoring device.

In some embodiments, the display comprises a touch screen.

In some embodiments the process further comprises providing a suggested movement of the wireless transceiver.

In some embodiments, the wireless analyte monitoring sensor comprises a wireless glucose monitoring sensor.

The process wherein the wireless analyte monitoring sensor is configured to be implanted subcutaneously.

In some embodiments, the wireless transceiver is integrated with the analyte monitoring device.

In some embodiments, the wireless transceiver comprises a Near-Field Communication (NFC) transceiver.

In some embodiments, the wireless transceiver is configured to provide power to the wireless analyte monitoring sensor.

In some embodiments, the electronic communication is transmitted by the wireless transceiver to the analyte monitoring device via one of: a cellular link, a Wi-Fi link, and a wired link.

In some embodiments, the analyte monitoring device comprises one of: a mobile device, a medical device, or a computer.

In some embodiments, the communications link is a first communications link, and the wireless transceiver communicates to the computing device via a second communications link.

In some embodiments, the process further comprises tracking the relative position of the wireless transceiver.

In some embodiments, the process further comprises tracking the relative position of the wireless transceiver using an accelerometer.

In some embodiments, the process further comprises tracking the signal strength with respect to the relative position of the wireless transceiver to the wireless analyte monitoring sensor.

In some embodiments, the process further comprises tracking the signal strength with respect to the position of the wireless transceiver.

In some embodiments, the process further comprises tracking the signal strength with respect to the position of the wireless analyte monitoring sensor.

In some embodiments, the process further comprises displaying suggested movements of the wireless transceiver to increase signal strength.

In some embodiments, the process further comprises displaying suggested movements of the wireless transceiver to maximize the signal strength.

In some embodiments, the process further comprises displaying suggested movements of the wireless transceiver to obtain a signal strength that exceeds a threshold.

In some embodiments, the process further comprises displaying instructions for adhering the wireless transceiver to a location having a signal strength that exceeds a threshold.

In some embodiments, the location is external to the body part containing the wireless analyte monitoring sensor.

In some embodiments, the location is on the surface of a body part containing the wireless analyte monitoring sensor.

In some embodiments, the process further comprises locating the wireless analyte monitoring sensor for extraction.

In some embodiments, the wireless analyte monitoring sensor comprises a fluorometer.

The process further comprising providing a suggested movement of the wireless analyte monitoring sensor.

In some embodiments, the suggested movement comprises a depth.

In some embodiments, the suggested movement comprises a lateral movement.

Another aspect of the invention may provide a wireless analyte monitoring device comprising: one or more processors; a communications interface; a display; a graphical user interface; a memory; and a non-transitory tangible computer readable medium comprising computer readable instruction configured to cause the one or more processors to perform a process comprising: receiving, via the communications interface, an electronic communication from a wireless transceiver, the electronic communication comprising information on a wireless signal of a first communications link between the wireless transceiver and a wireless analyte monitoring sensor; determining a real-time signal strength for the wireless signal in response to receiving the electronic communication; and displaying the signal strength on the graphical user interface of the display.

In some embodiments, the display comprises a touch screen.

In some embodiments, the process further comprises providing a suggested movement of the wireless transceiver.

In some embodiments, the wireless analyte monitoring sensor is a wireless glucose monitoring sensor.

In some embodiments, the wireless analyte monitoring sensor is configured to be implanted subcutaneously.

In some embodiments, the wireless transceiver is integrated with the wireless analyte monitoring device.

In some embodiments, the wireless transceiver is an NFC transceiver.

In some embodiments, the wireless transceiver is configured to provide power to the wireless analyte monitoring sensor.

In some embodiments, the wireless transceiver comprises a cellular communications device.

In some embodiments, the wireless analyte monitoring device comprises one of: a mobile device, a medical device, or a computer.

In some embodiments, the wireless transceiver communicates with the wireless analyte monitoring device via a communications interface comprising one of: a wireless link, a Wi-Fi interface, or a wired interface.

In some embodiments, the process further comprises tracking the relative position of the wireless transceiver.

In some embodiments, the process further comprises tracking the relative position of the wireless transceiver employing an accelerometer.

In some embodiments, the process further comprises tracking the signal strength with respect to the relative position of the wireless transceiver to the wireless implanted analyte monitoring sensor.

In some embodiments, the process further comprises tracking the signal strength with respect to the position of the wireless transceiver.

In some embodiments, the process further comprises tracking the signal strength with respect to the position of the wireless analyte monitoring sensor.

In some embodiments, the process further comprises displaying suggested movements of the wireless transceiver to increase signal strength.

In some embodiments, the process further comprises displaying suggested movements of the wireless transceiver to maximize the signal strength.

In some embodiments, the process further comprises displaying suggested movements of the wireless transceiver to obtain a signal strength that exceeds a threshold.

In some embodiments, the process further comprises displaying instructions for adhering the wireless transceiver to a location having a signal strength that exceeds a threshold.

In some embodiments, the location is external to the body part containing the wireless analyte monitoring sensor. In some embodiments, the location is on the surface of a body part containing the wireless analyte monitoring sensor.

In some embodiments, the process further comprises locating the wireless analyte monitoring sensor for extraction.

In some embodiments, the wireless analyte monitoring sensor comprises a fluorometer.

In some embodiments, the process further comprises providing a suggested movement of the wireless analyte monitoring sensor.

In some embodiments, the suggested movement comprises a depth.

In some embodiments, the suggested movement comprises a lateral movement.

Further variations encompassed within the devices, processes, and computer readable mediums are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 14A is an example calibration notification screen display of a medical mobile application in accordance with aspects of various embodiments of the present invention.

FIGS. 14B-C are example calibration screen displays of a medical mobile application in accordance with aspects of various embodiments of the present invention.

FIG. 14D is an example calibration confirmation screen display of a medical mobile application in accordance with aspects of various embodiments of the present invention.

FIGS. 20A-B are an example home screen displays in portrait and landscape mode of a medical mobile application in accordance with aspects of various embodiments of the present invention.

DETAILED DESCRIPTION OF PREFERRED EMBODIMENTS

Embodiments of the present invention interact with, directly and/or indirectly, analyte monitoring sensor(s) to enhance the technological capabilities of the analyte monitoring. An analyte monitoring sensor may be employed to continually measure, among other biological factors, analyte (e.g., glucose) levels. In some embodiments, the sensor may be an implantable sensor, which may be implanted fully or partially under the skin by, for example, a physician. However, this is not required, and, in some alternative embodiments, the sensor may be an external sensor. In some embodiments, the sensor may be wireless analyte monitoring sensor. However, this is not required, and, in some alternative embodiments, the sensor may be wired (e.g., transcutaneous analyte monitoring system). Non-limiting examples of analyte monitoring sensors and systems may be found in co-pending application Ser. Nos. 14/580,289, 13/761,839, and 13/650,016, which are hereby incorporated by reference in their entirety.

Figure 1:
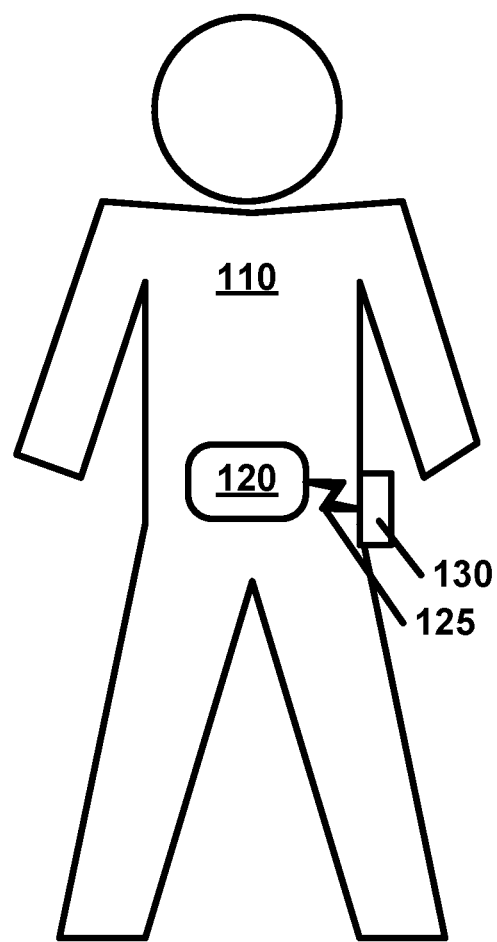
FIG. 1 is a block diagram of a wireless analyte monitoring system employed in accordance with an aspect of an embodiment of the present invention.

FIG. 1 is a block diagram of an analyte monitoring sensor 120 in accordance with an aspect of an embodiment of the present invention. In some embodiments, as shown in the FIG. 1, the analyte monitoring sensor 120 may be a wireless, implantable sensor inserted subcutaneously inside a patient 110. The analyte monitoring sensor 120 may measure interstitial fluid glucose levels and communicate these levels wirelessly via a wireless channel 125 to a transceiver 130. The transceiver 130 may employ an application to interact with the analyte monitoring sensor 120. The transceiver 130 may be worn externally within communications range of the sensor. This location may be, for example, over the implanted analyte monitoring sensor 120.

The transceiver 130 may be a reusable device configured to power the analyte monitoring sensor 120, via wireless power transfer mechanisms. Wireless power transfer or wireless energy transmission is the transmission of electrical power from a power source to a consuming device without using solid wires or conductors. It is a term that refers to a number of different power transmission technologies that may use, for example, time-varying electromagnetic fields. Wireless transmission is useful to power electrical devices in cases where interconnecting wires are inconvenient, are hazardous, or are not possible. In wireless power transfer, a transmitter device (e.g. transceiver 130) may be connected to a power source, such as a battery, a transformer, a power line, and the like. The transmitter device may transmit power by electromagnetic fields across an intervening space to one or more receiver devices, where the electromagnetic fields are converted back to electric power and utilized.

Wireless power techniques may be non-radiative and/or radiative. In near-field or non-radiative techniques, power may be transferred over short distances by magnetic fields using inductive coupling between coils of wire or in a few devices by electric fields using capacitive coupling between electrodes. Applications of this type comprise Radio Frequency Identifier (RFID) tags, smartcards, and implantable medical devices like artificial cardiac pacemakers. In radiative or far-field techniques, also called power beaming, power may be transmitted by beams of electromagnetic radiation, like microwaves or laser beams. These techniques may transport energy aimed at the receiver longer distances.

Figure 2:
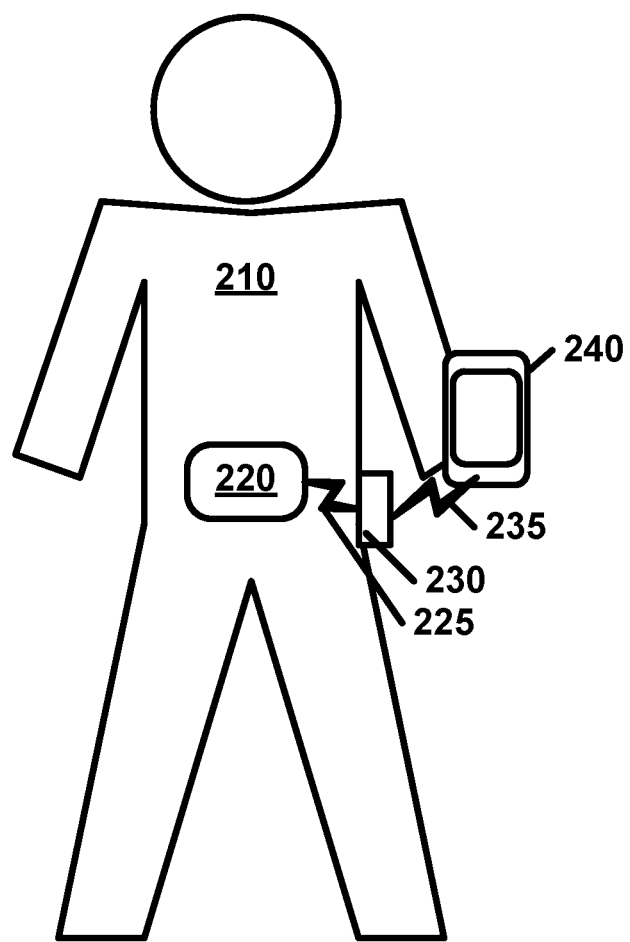
FIG. 2 is a block diagram of a wireless analyte monitoring sensor employed to communicate to a mobile device via a transceiver in accordance with an aspect of an embodiment of the present invention.

FIG. 2 is a block diagram of an analyte monitoring sensor 220 employed to communicate to a mobile device 240 via a transceiver 230 in accordance with an aspect of an embodiment of the present invention. In some non-limiting embodiments, the sensor 220 may be a wireless, implantable sensor implanted inside a patient 210 (e.g., inserted subcutaneously inside a patient 210). The transceiver 230 may be configured to provide power to and/or receive sensor-measured analyte information from the analyte monitoring sensor 220 over communications link 225. The transceiver 230 may communicate the sensor-measured analyte information to another device 240 via a second communications link 235.

Device 240 may comprise, for example, a handheld mobile device (e.g. Smartphone) configured to process the sensor-measured analyte information employing a mobile application, such as the mobile medical application described herein. The mobile application may display analyte related information such as, but not limited to: glucose information, current glucose readings, user notifications, glucose status alerts and alarms, trend graphs and arrows, and user-entered events.

According to some of the various embodiments, device 240 may comprise a handheld mobile device such as a commercially available smartphone, tablet, iPod, personal computer (PC), and/or the like. The handheld mobile device 240 may communicate with the transceiver through a wireless connection 235 such as, for example, Bluetooth™, Wi-Fi_33, and/or the like. According to some of the various embodiments, the mobile application may be configured to run under an operating platform such as iOS (e.g., iPhone) or Android. According to other embodiments, the mobile application may be an embedded application written to operate without the assistance of an operating platform.

FIGS. 3-6 are block diagrams illustrating multi-peer connectivity between processing devices of sensor-measured analyte information obtained from a wireless analyte monitoring sensor in accordance with aspects of various embodiments of the present invention. Multi-peer connectivity comprises a structure of multiple devices connected over communication infrastructure(s) comprising one or more communication links. The term communication link(s) or link, refers to communications of information between two devices over a transmission medium. A communications link may employ a physical communications technology such as wire, fiber optic, and/or the like. Examples of wired links comprise, but are not limited to: cable, wire, twisted-pair wire, fiber-optic, Ethernet, USB, and/or the like. Similarly, a communications link may employ a wireless communications technology. A wireless communications link employs a wireless technology configured to communicate information between two devices without a physical medium such as wire, fiber optic, and/or the like. Examples of wireless communications links comprise, but are not limited to: cellular, Wi-Fi, Bluetooth™, Near-Field Communications (NFC), infrared, radar, satellite, radio frequency, combinations thereof, and/or the like. A link may be employed to convey an information signal, for example a digital bit stream, from one or several senders (or transmitters) to one or several receivers. A link has a certain capacity for transmitting information, often measured by its bandwidth in hertz (Hz) or its data rate in bits per second.

Through multi-peer connectivity, various devices may share, for example, analyte data, health data, customized notifications, analyte level alerts, trend information, combinations thereof, and/or the like. Some of the sharing may be device specific. Some of the sharing may be among identified groups, such as for example, a circle of concern (e.g. people who may have an interest in monitoring data for a patient), specific devices (e.g. web apps, servers, data storage, and/or the like), specific applications (e.g. applications configured to process specific data), and/or the like.

Figure 3:
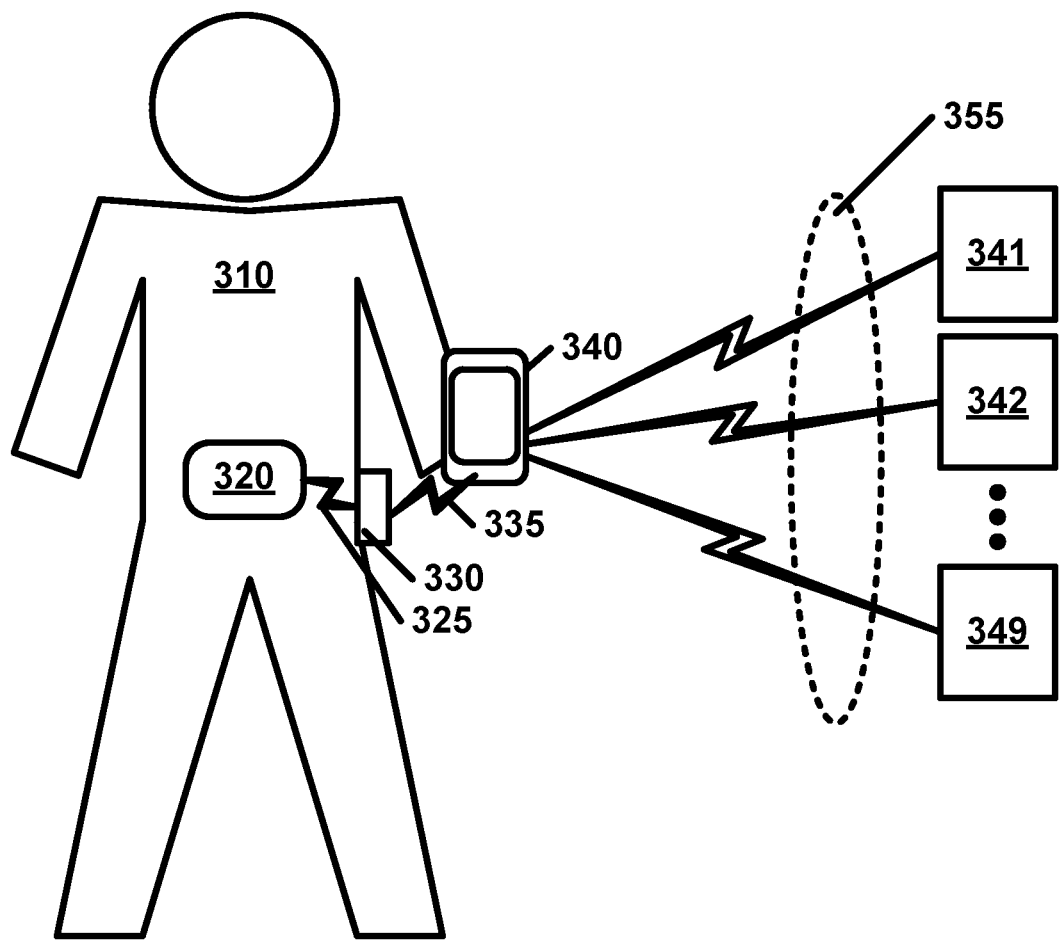
FIGS. 3-6 are block diagrams illustrating multi-peer connectivity between processing devices of sensor-measured analyte information obtained from a wireless analyte monitoring sensor in accordance with aspects of various embodiments of the present invention.

According to another embodiment shown in FIG. 3, a patient 310 has an analyte sensor 320. In some non-limiting embodiments, the sensor 320 may be a wireless sensor implanted in a patient 310. A transceiver 330 may be disposed external to the patient 310 at a location within communications range of analyte sensor 320. The transceiver 330 may be configured to provide power to the analyte sensor 320. Transceiver 330 may be configured to receive biological measurements from the analyte sensor 320 over communications link 325. Transceiver 330 may be configured to communicate to one or more other devices (341, 342 . . . 349) over communications link(s) 335. At least some of the biological measurements may be communicated from transceiver 330 to one or more other devices (341, 342 . . . 349) over communications link(s) 335. According to some of the various embodiments, one or more other devices (341, 342 . . . 349) may comprise a mobile device such as, but not limited to: a smart phone, a tablet, an iPod, and/or the like. However, the embodiments are not so limiting. For example, one or more other devices (341, 342 . . . 349) may comprise another type of device such as, but not limited to: a PC, a netbook, a medical monitoring device, and/or the like. Device 340 may communicate at least some of the data associated with and/or acquired by analyte sensor 320 to one or more other devices (341, 342, . . . 349) over communications link 355.

Figure 4:
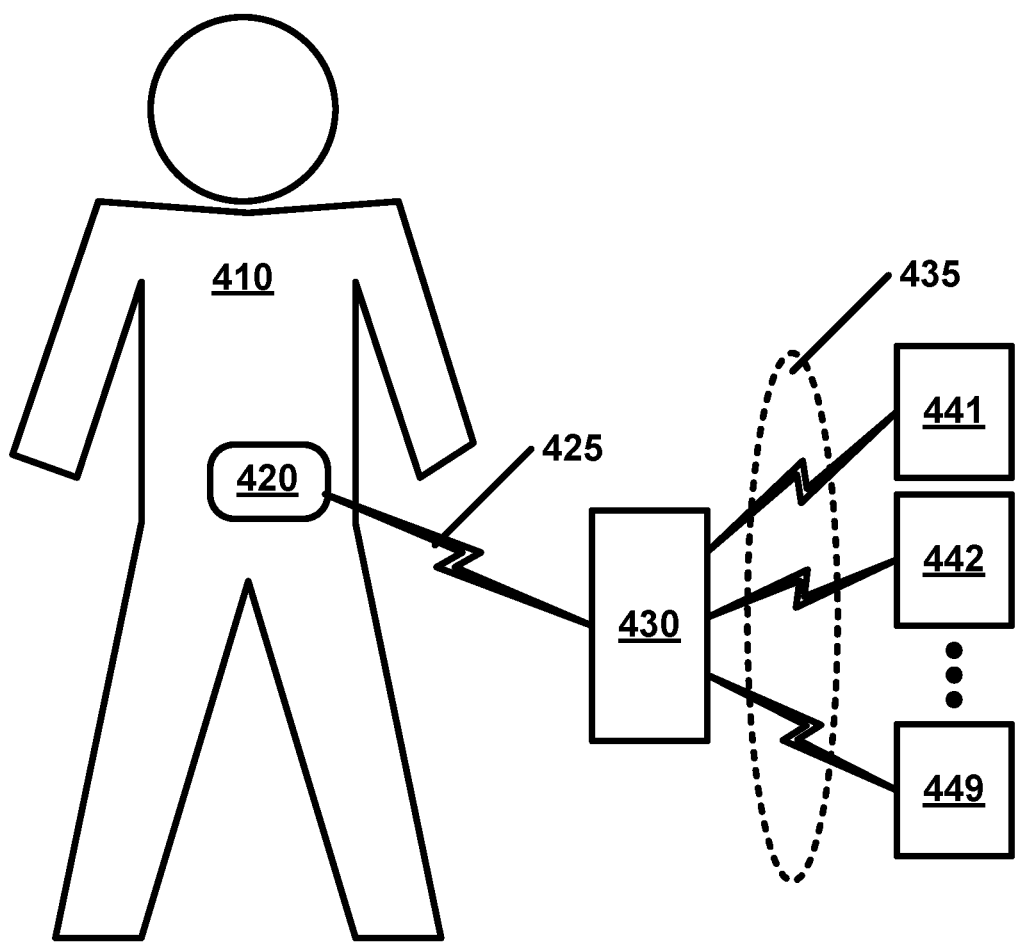

According to another embodiment shown in FIG. 4, a patient 410 has an analyte sensor 420. In some non-limiting embodiments, the sensor 420 may be a wireless sensor implanted in a patient 410. A transceiver 430 may be disposed external to the patient 410 at a location within communications range of analyte sensor 420. The transceiver 430 may be configured to provide power to the analyte sensor 420. Transceiver 430 may be configured to receive biological measurements from the analyte sensor 420 over communications link 425. According to some of the various embodiments, and as shown in this illustration, communications link 425 may have sufficient power to communicate to a location that is external, but not directly touching patient 410.

Transceiver 430 may be configured to communicate to one or more device(s) (441, 442 . . . 449) over communications link(s) 435. At least some of the biological measurements may be communicated from transceiver 430 to one or more device(s) (441, 442 . . . 449) over communications link(s) 435. According to some of the various embodiments, one or more of device(s) (441, 442 . . . 449) may comprise a mobile device such as, but not limited to: a smart phone, a tablet, an iPod, and/or the like. However, the embodiments are not so limiting. For example, one or more of device(s) (441, 442 . . . 449) may comprise another type of device such as, but not limited to: a PC, a netbook, a medical monitoring device, and/or the like.

Figure 5:
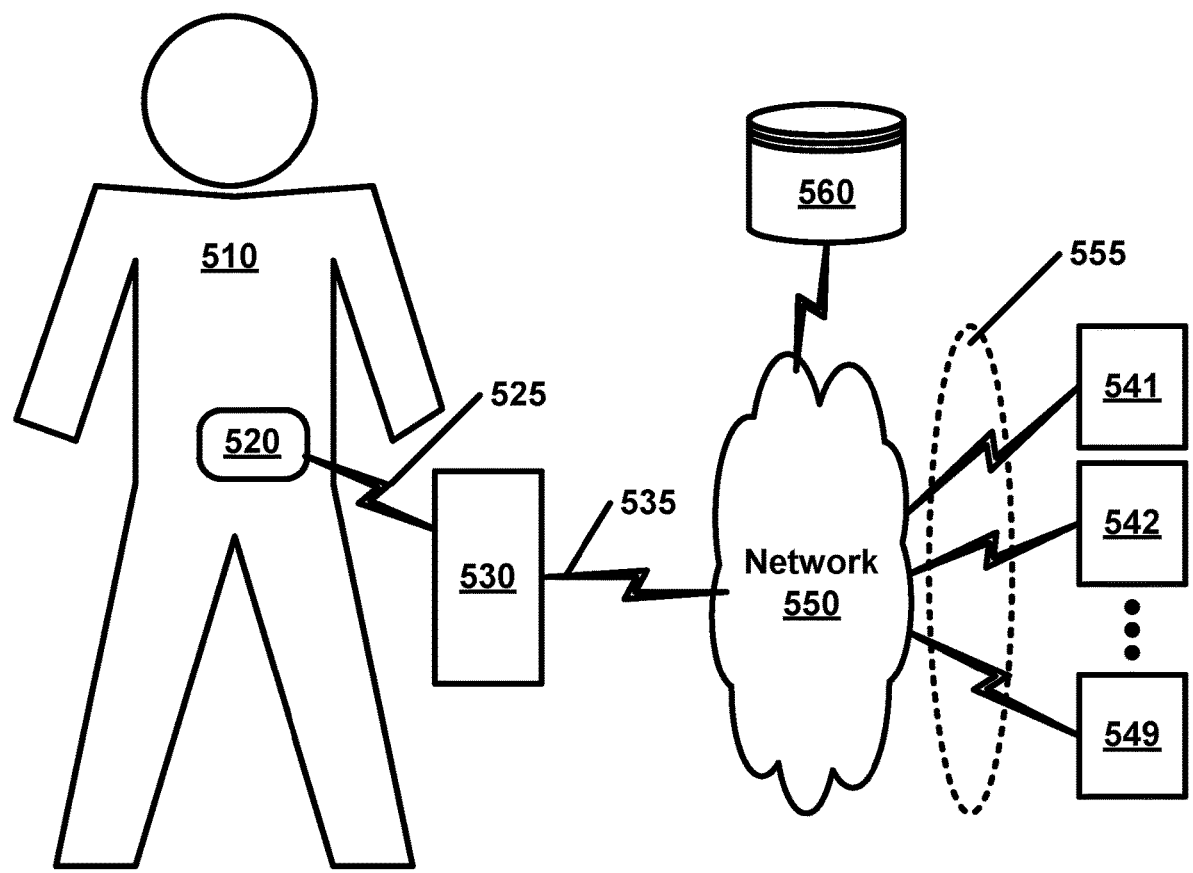

According to another embodiment, shown in FIG. 5, a patient 510 has an analyte sensor 520. In some non-limiting embodiments, the sensor 520 may be a wireless sensor implanted in a patient 510. A transceiver 530 may be disposed external to the patient 510 at a location within communications range of analyte sensor 520. Depending upon the power capabilities of transceiver 530, the location of transceiver 530 may be placed on or near the skin of patient 510 and/or at a distance from patient 510. The transceiver 530 may be configured to provide power to the analyte sensor 520. Transceiver 530 may be configured to receive biological measurements from the analyte sensor 520 over communications link 525.

Transceiver 530 may be configured to communicate to one or more device(s) (541, 542 . . . 549) over communications link(s) 535 and 555 via network 550. Network 550 may comprise, but is not limited to: the Internet, intranets, cellular, combinations thereof, and/or the like. At least some of the biological measurements may be communicated from transceiver 530 to one or more device(s) (541, 542 . . . 549) over communications link(s) 535 and 555 via network 550. According to some of the various embodiments, one or more of device(s) (541, 542 . . . 549) may comprise a mobile device such as, but not limited to: a smart phone, a tablet, an iPod, and/or the like. However, the embodiments are not so limiting. For example, one or more of device(s) (541, 542 . . . 549) may comprise another type of device such as, but not limited to: a PC, a netbook, a medical monitoring device, and/or the like.

According to some of the various embodiments, one or more of transceiver 530 and/or device(s) (541, 542 . . . 549) may communicate over communications link(s) 535 and/or 555 via network 550 to storage device 560. Storage device 560 may comprise, for example, network attached storage, server storage, web storage, combinations thereof, and/or the like. Storage device 560 may act as a depository for data associated with and/or acquired by wireless analyte sensor 520.

Figure 6:
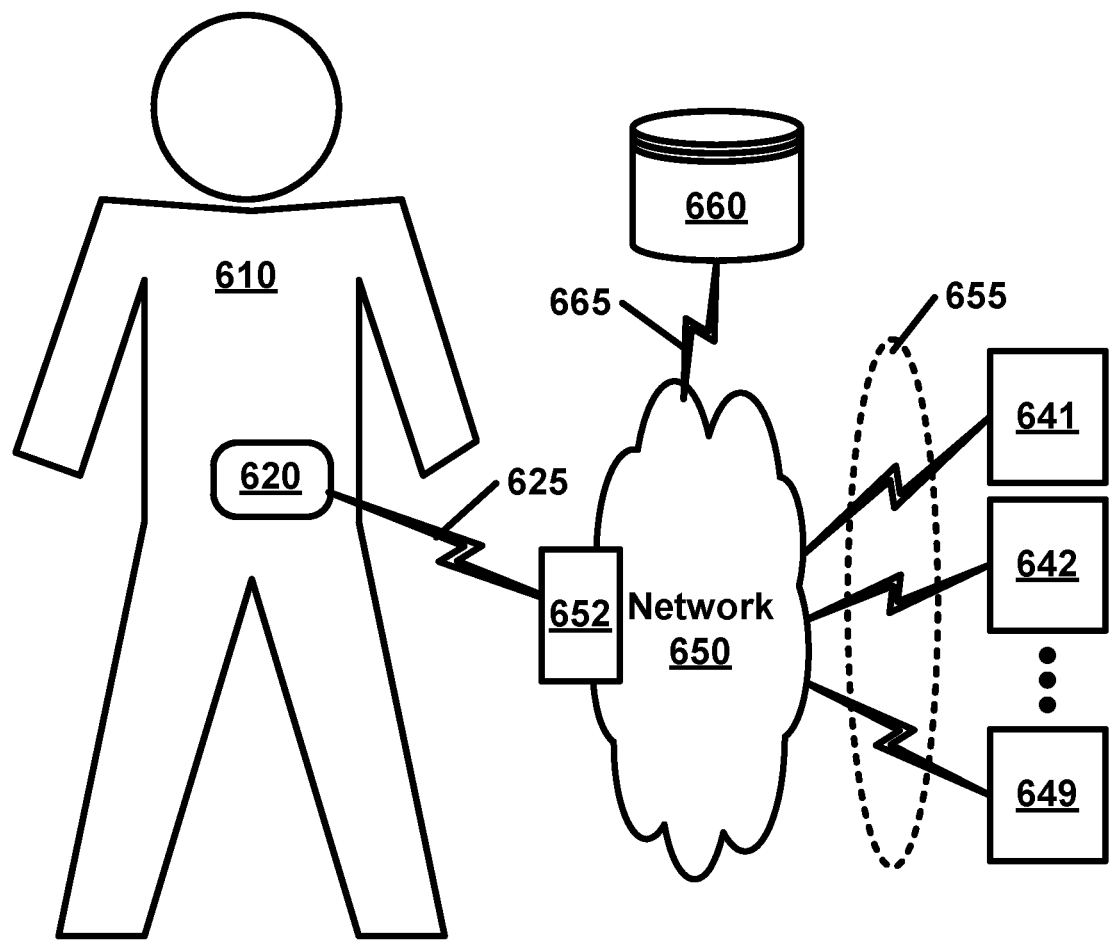

According to another embodiment, shown in FIG. 6, a patient 610 has an analyte sensor 620. In some non-limiting embodiments, the sensor 620 may be a wireless sensor implanted in a patient 610. Analyte sensor 620 may be configured to communicate to one or more device(s) (641, 642 . . . 649, and 660) over communications link(s) 625, 655 and/or 665 via network 650. Network 650 may comprise, but is not limited to: the Internet, intranets, cellular, combinations thereof, and/or the like.

Analyte sensor 620 may communicate to network 650 via a network port 652 such as, but not limited to: a network access point, a Wi-Fi port, a switch, a cellular connection point, combinations thereof, and/or the like. The network port may be disposed external to patient 610 at a location within communications range of the analyte sensor 620. Depending upon power capabilities of the analyte sensor 620, the location of network port 652 may be placed on or near the skin of patient 610 and/or at a distance from patient 610. Power may be provided to the analyte sensor 620 by a power source such as, but not limited to: a wireless power transmitter, an induction source, a battery, a bio-generator, a motion based piezoelectric power generator, combinations thereof, and/or the like. Network port 652 may be configured to pass biological measurements from the analyte sensor 620 over communications link 625.

At least some of the biological measurements may be communicated from the analyte sensor 620 to one or more device(s) (641, 642 . . . 649, and 660) over communications link(s) 625, 655 and/or 665 via network 650. According to some of the various embodiments, one or more of device(s) (641, 642 . . . 649) may comprise a mobile device such as, but not limited to: a smart phone, a tablet, an iPod, and/or the like. However, the embodiments are not so limiting. For example, one or more of device(s) (641, 642 . . . 649) may comprise another type of device such as, but not limited to: a PC, a netbook, a medical monitoring device, and/or the like. According to some of the various embodiments, one or more of analyte sensor 620 and/or device(s) (641, 642 . . . 649) may communicate over communications link(s) 625, 655 and/or 665 via network 650 to storage device 660. Storage device 660 may comprise, for example, network attached storage, server storage, web storage, combinations thereof, and/or the like. Storage device 660 may act as a depository for data associated with and/or acquired by wireless analyte sensor 620.

Figure 7:
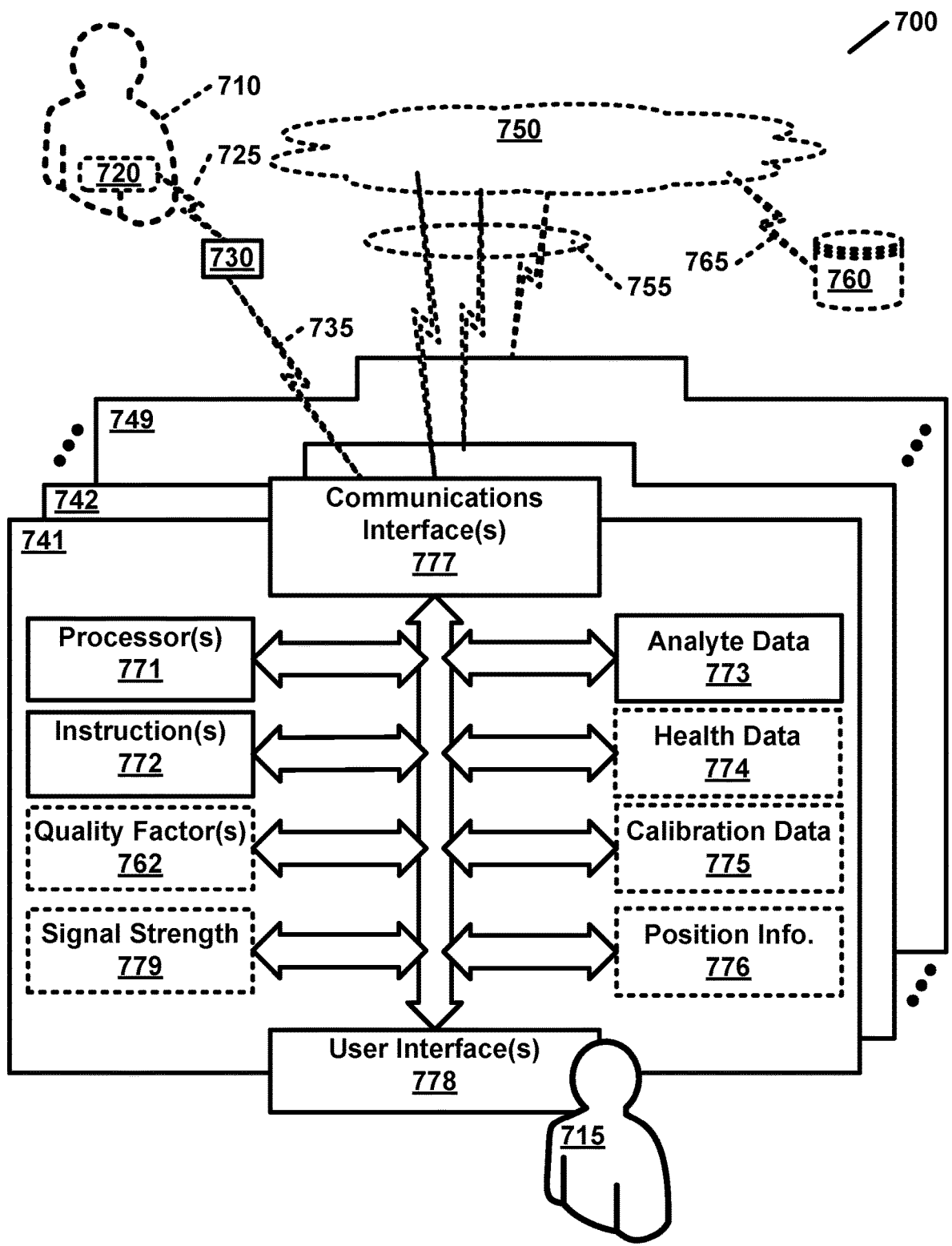
FIG. 7 is a block diagram of an analyte monitoring device communicatively connected to at least a wireless analyte monitoring sensor in accordance with aspects of various embodiments of the present invention.

FIG. 7 is a block diagram of an analyte monitoring system 700 embodying some aspects of the present invention. In some embodiments, the analyte monitoring system may include an analyte monitoring device 741 communicatively connected to at least an analyte monitoring sensor 720 in accordance with aspects of various embodiments of the present invention. In some non-limiting embodiments, the sensor 720 may be a wireless sensor implanted in a patient 710. In some non-limiting embodiments, the analyte monitoring device 741 may be a wireless analyte monitoring device. In some non-limiting embodiments, the analyte monitoring system 700 may be a wireless analyte monitoring system. In some non-limiting embodiments, the analyte monitoring device 741 may include one or more user interfaces 778 for communication with a user 715 (e.g., patient 710, a health care provider, family member, or other person). In some embodiments, one or more user interfaces 778 may include one or more input and/or output devices, such as, for example and without limitation, pushbutton(s), a keyboard, a microphone, a camera, a pointing device (e.g., a mouse, trackball, or touch pad), touch screen(s), voice interfaces(s), multimedia interface(s), audio interface(s), tactile interfaces(s), visual interface(s), combinations thereof, and/or the like. The dashed elements may communicate to the analyte monitoring device 741 according to multiple embodiments, several examples of which have already been discussed with respect to FIGS. 1-6. FIG. 7 will be referenced with respect to several embodiments comprising device positioning, calibration, and data sharing/processing.

Figure 8:
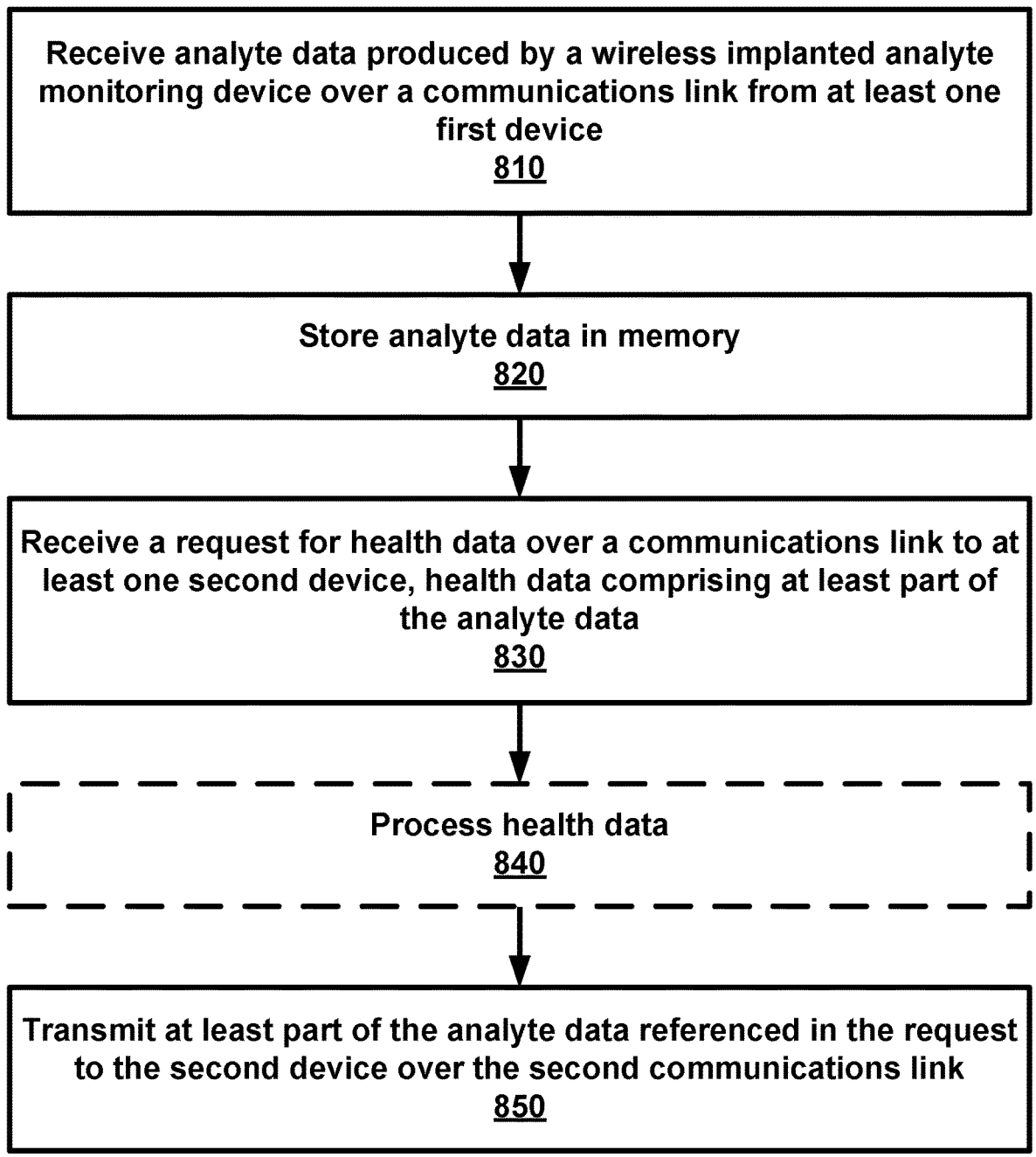
FIG. 8 is a flow diagram illustrating communication between a wireless analyte monitoring sensor and an analyte monitoring device in accordance with aspects of various embodiments of the present invention.

FIG. 8 is a flow diagram illustrating communication between an analyte monitoring device(s) 741 and an analyte monitoring sensor 720 in accordance with aspects of various embodiments of the present invention. Processor(s) 771 in analyte monitoring device(s) 741 may execute computer readable instructions 772 stored on a non-transitory tangible computer readable medium to perform processes that employ systems configured to interact with analyte monitoring device(s) 741. These processes may be configured to improve the technological field of analyte monitoring and drug dispersion on a living patient.

Embodiments add a range of new capabilities to the employment of the analyte monitoring sensor 720 by adding management, calibration, data sharing and reporting functions not otherwise available. For example, some of the embodiments may employ smartphones, tablets, and other computing devices configured to perform as a continuous glucose monitoring system. This configuration may provide people with diabetes a better means to manage diabetes. Diabetes is a metabolic disease in which the body's inability to produce any or enough insulin causes elevated levels of glucose in the blood. Treatment for diabetes includes oral medications and injection or infusion of basal and/or bolus insulin. Traditionally a person with diabetes carries a self-monitoring blood glucose meter (SMBG) to measure their blood glucose at regular intervals. To manage diabetes effectively, a person may need to understand and act upon at least the following: the frequency and timing of blood glucose monitoring; Insulin therapy—types of insulin used, timing of dosing, amount of dose; low blood sugar—how to recognize and treat; high blood sugar—how to recognize and treat; nutrition—types of food and their effect on blood sugar; carbohydrate counting; exercise—adjusting insulin and food intake for activity; medical management—how often to visit the doctor and other diabetes care specialists; combination thereof and/or the like. Failing to treat one or more of these conditions could lead to life threatening events.

In accordance with one embodiment, analyte data for a living being produced by an analyte sensor 720 over a communications link 735 from at least one first device 730 may be received at step 810. The received analyte data may be stored in analyte data memory 773 at step 820. The analyte data may comprise at least one of the following: glucose data; sugar data; oxygen data; antibodies data; temperature data; cell counts data; ph. data; combinations thereof, and/or the like.

According to some of the various embodiments, one or more of the first device(s) 730 may be an analyte monitoring device(s) similar to analyte monitoring device(s) (741, 742 . . . 749), which may include one or more wireless analyte monitoring devices. In one of these embodiments, the analyte monitoring device(s) (741, 742 . . . 749) may be configured so that one or more of the communication interface(s) 777 is configured to communicate directly with analyte sensor 720. In some non-limiting embodiments, one or more of the communication interface(s) 777 may be a wireless communication interface. According to some of the various embodiments, one or more of the first device(s) 730 may be at least one of the second device(s) (741, 742 . . . 749).

According to some of the various embodiments, one or more of the first device(s) 730 may be an intermediary device. In one of these embodiments, the first device 730 may be configured to relay analyte and/or other information from the analyte sensor 720 to one or more of the analyte monitoring device(s) (741, 742 . . . 749). According to some of the various embodiments, the relay may be intelligent (e.g. controlled by logical circuitry). In yet other embodiments, the relay may be a straight relay link in which the communications is passed through without regard to the content. In yet other embodiments, the relay may have an intermediary level of control (e.g. protocol management).

A request for health data may be received over a communications link to at least one second device at step 830, as illustrated in FIG. 8.

According to some of the various embodiments, one or more of the second device(s) (741, 742 . . . 749) may be one of a host of devices configured to communicate within the disclosed framework. For example, one or more of the second device(s) (741, 742 . . . 749) may be a mobile device, a peer device, a personal computer, a tablet, a combination thereof, and/or the like. According to another example, one or more of the second device(s) (741, 742 . . . 749) may comprise a medical device such as, but not limited to: a blood glucose meter, an insulin pump, a combination thereof, and/or the like. According to another example, one or more of the second device(s) (741, 742 . . . 749) may comprise a computing device configured with an application such as, but not limited to: a health monitoring application; a mobile medical application, an electronic health logging application. In yet another example, one or more of the second device(s) (741, 742 . . . 749) may comprise a health monitoring device such as a health monitoring watch, an activity sensor, a food monitoring device, combinations thereof, and/or the like.

Health data 774 may comprise at least part of the analyte data 773. Further, according to some of the various embodiments, the health data 774 may comprise at least one of the following: food data, exercise data, well-being data, fitness data, medicine data, trend data, notification data, reminder data, scheduling data, sleep data, alert data, settings, preferences, calibration data, device health, combinations thereof, and/or the like. According to some of the various embodiments, at least part of the health data 774 may be further processed at step 840 (see FIG. 8). For example, health data 774 may be formatted into one or more of various formats such as, but not limited to: an extensible markup language format, a spreadsheet format, a database format, a communications format, combinations thereof, and/or the like. As another example, health data may be processed to generate trending data, chart data, statistical data, relative data format, alert data, time-stamped data, combinations thereof, and/or the like.

Communication links 725, 735, 755 and 765 may comprise many technologies as discussed earlier in the introduction to the descriptions of FIGS. 3-6. So for example, at least part of the second communications link may communicate over a communications link such as, but not limited to: a cellular network, a wired network, the Internet, an intranet, Wi-Fi, Bluetooth™, Near-Field Communications (NFC), infrared, RF, a combination thereof, and/or the like.

The requested health data, which may include at least part of analyte data 773, may be transmitted to the at least one second device (741, 742 . . . 749) over a second communications link 755 at step 850.

As described, according to some of the various embodiments, at least part of the analyte data may be shared over communications link (e.g. 725, 735, 755, 765, and/or the like) to a multitude of devices. According to some embodiments, some of the device(s) may be a server device employed to allow data to be shared over a network 750 such as the Internet. The server may share data via proprietary formats configured to be employed by hardware computing systems configured, at least in part, with applications to make the hardware computing system into an analyte monitoring system. Some of the multitude of devices may include storage device(s) 760. Some of the storage devices may comprise a web accessible software as a services storage such as, for example, DropBox™, Google™ Drive, Microsoft™ OneDrive™ Amazon™ S3 storage, combinations thereof, and/or the like.

According to some of the various embodiments, a request for health data may be a synchronization request. A synchronization request may be a request to copy information that exists on one device to another device that does not have the information. According to other embodiments, some request(s) may be more specific, such as a request for specific health data, specific analyte data, combinations thereof, and/or the like. Some requests may include filter criteria, such as, but not limited to: data for specific user(s), data for specific time period(s), data for specific device(s), data related to specific activities, combinations thereof, and/or the like.

Figure 9:
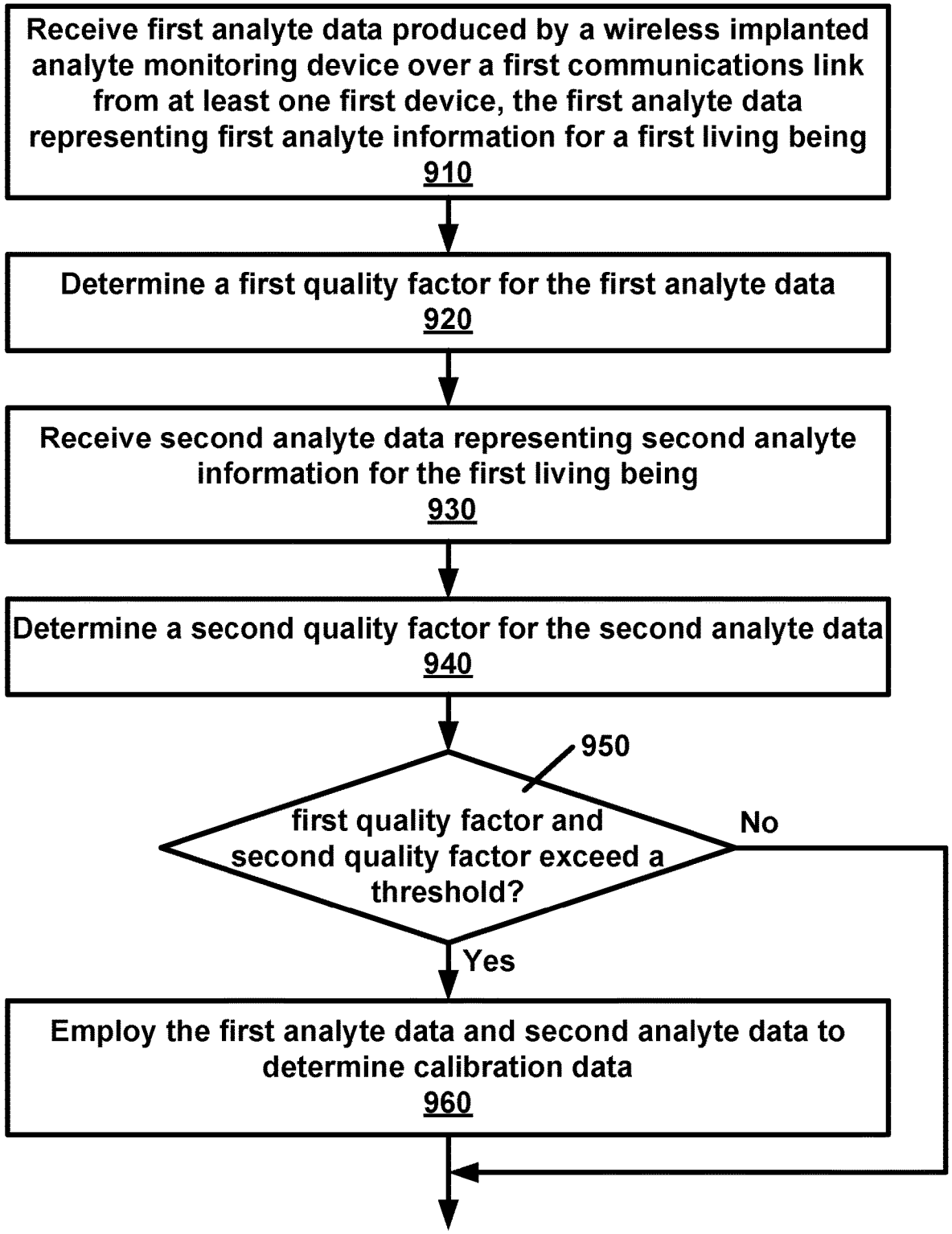
FIG. 9 is a flow diagram illustrating calibration of a wireless analyte monitoring sensor in accordance with aspects of various embodiments of the present invention.

FIG. 9 is a flow diagram illustrating calibration of an analyte monitoring sensor 720 in accordance with aspects of various embodiments of the present invention. According to some of the various embodiments, the analyte monitoring system 700 may be calibrated. According to some of the various embodiments, the calibration may comprise calibrating the analyte monitoring sensor 720 and/or calibrating one or more of the analyte monitoring device(s) (741, 742 . . . 749).

According to some of the various embodiments, first analyte data produced by an analyte monitoring sensor 720 may be received, for example, over a first communications link 735 from at least one first device 730 at step 910. Analyte monitoring sensor 720 may comprise, for example, a fluorometer. A fluorometer or fluorimeter may comprise a device configured to measure parameters of fluorescence: its intensity and wavelength distribution of emission spectrum after excitation by a certain spectrum of light. These parameters may be employed to identify the presence and the amount of specific molecules in a medium. The first analyte data may represent first analyte information for a first living being. First analyte data may be stored in analyte data storage 773.

According to some of the various embodiments, the first device 730 may comprise the analyte monitoring sensor 720. According to other embodiments, the first device 730 may comprise an intermediary device. An intermediary device may be a repeater that moves information to and/or from a monitoring sensor 720 and a monitoring device 741. In yet other embodiments, the first device 730 may comprise one or more of the second device(s) (741, 742 . . . 749). As discussed earlier, communication link(s) may comprise one or more of a multitude of communications mechanisms such as, but not limited to: cellular, wired, wireless, Wi-Fi, Bluetooth™, near-field communication, and infrared communication mechanisms. Bluetooth™ may comprise Bluetooth™ low energy. Some of these mechanisms may be networked. Some parts of a network may comprise the Internet, intranet(s), ad-hoc networks, combinations thereof, and/or the like.

The first analyte data may be, according to some of the various embodiments, received employing one or more manual data input mechanism(s). The manual data input may involve, for example, accepting manual data via a touchscreen, typing, selecting, combinations thereof, and/or the like. The manual data input may involve other graphical control elements. A graphical control element may comprise software component(s) that operate in combination with hardware to enable a user to interact with a system through direct manipulation. Various graphical control elements may provide different user-computer interactions and may involve the display of collections of related items (such as with various list and canvas controls), initiation of actions and processes within the interface (buttons and menus), navigation within the space of the information system (links, tabs and scrollbars), representing and manipulating data values (labels, check boxes, radio buttons, sliders, scroll selectors, spinners . . . ), combinations thereof, and/or the like. Other embodiments may comprise input mechanisms such as, but not limited to: a scroll selector(s) (e.g. horizontal scroll selector(s), vertical scroll selector(s), and wheel scroll selector(s)); a keypad entry; a suggested values list; icon(s); a location on a graphic; a voice entry system; a scanner; an image; optical character recognition (OCR), combinations thereof, and/or the like.

According to some of the various embodiments, second analyte data representing second analyte information for the first living being may be received by, for example, analyte monitoring device 741 at step 930. The second analyte data may be stored in analyte data storage 773. Second analyte data may, according to various embodiments, be entered via manual and/or automated mechanisms. Manual entry may be achieved using mechanisms that are substantially similar to entry mechanisms described above with respect to entry of first analyte data.

The second analyte data may be externally collected analyte data 773 from sources such as, but not limited to: computing capable devices, medical devices, applications, combinations thereof, and/or the like. Examples of computing devices that provide second analyte data comprise, but are not limited to: mobile device(s), peer device(s), server(s), smart phone(s), tablet(s), personal computer(s), iPod(s), netbook(s), combinations thereof, and/or the like. Computing devices may comprise interfaces such as, but not limited to: touch screen(s), voice interfaces(s), multimedia interface(s), audio interface(s), tactile interfaces(s), visual interface(s), combinations thereof, and/or the like. Some of the devices may comprise, but not be limited to: imaging device(s), blood glucose meter(s), insulin pump(s), fingerstick blood glucose tester(s), external analyte measurement device(s), fitness monitoring device(s), combinations thereof, and/or the like. Some of the external monitoring devices may comprise devices that are configured to measure and/or collect data that may affect analyte values such as body temp thermistor(s), hydration monitor(s), blood pressure meter(s), light sensor, chemical sensor, antibody sensor(s), combinations thereof, and/or the like. Some of the fitness devices may comprise devices such as a health monitoring watch, activity monitors, and activity reporting exercise equipment.

Analyte data reporting applications may comprise applications such as fitness and/or health monitoring application(s) that may be configured to collecting data that may affect measurement quality. Examples of data that may affect measurement quality comprise: diet information, exercise information, sleep information, stress information, combinations thereof and/or the like. Examples of other applications that may be configured to collect data that may affect measurement quality comprise mobile medical application(s) and electronic health logging application(s).

The first analyte data and second analyte data may each comprise data such as, for example: glucose data, sugar data, oxygen data, antibodies data, temperature data, cell counts data, ph. data, combinations thereof, and/or the like.

According to some of the various embodiments, analyte data 773 that originates from various sources such as, but not limited to, example sources discussed herein may be pre-processed. Pre-processing may comprise processing input data to produce output that is compatible with other programs, other devices, other processing steps, combinations thereof, and/or the like. The amount and kind of processing done may depend upon requirements and/or configurations of specific embodiments and may range from performing relatively simple textual substitutions and macro expansions to applying relatively complex methodologies to adapt the data. Preprocessing may, for example, modify the format of the analyte data 773 to conform to various formats such as, but not limited to: customized specific data formats, spreadsheet data formats, charting formats, relative data formats, trending data formats, alert formats, statistical formats, time defined formats (e.g. time-stamped), combinations thereof, and/or the like. Some of the preprocessing may comprise normalizing data, applying correction factors to data, combinations thereof, and/or the like.

A first quality factor may be determined for the first analyte data at step 920. Similarly, a second quality factor may be determined for the second analyte data at step 940.

The first quality factor for the first analyte data may comprise verifying that the first analyte data was collected during a proper operating phase. For example, data collected within an insertion phase (a predetermined amount of time after insertion of the sensor 720, e.g. 2 hrs., 12 hrs., 24 hrs.) may be inaccurate. The first quality factor may additionally or alternatively consider other factors such as whether a measurement is out of bounds, an outlier, obtained from an inoperable sensor 720, obtained from an unstable sensor, combinations thereof and/or the like.

Various other factors may be employed in determining at least one of the first quality factor and the second quality factor. For example, the rate of change with respect to earlier analyte data measurements may be employed. The time of an earlier (and/or last) calibration may be taken into account, so that, for example, data from a recent measurement may be ignored. Other factors that may be considered may comprise, but not be limited to: accounting for the amount of analyte data collected, verifying that the analyte data falls within a predetermined and/or dynamic operating range, accounting for the operating conditions when the analyte data was collected (e.g. temperature conditions, humidity conditions, light conditions, chemical exposure conditions, combinations thereof, and/or the like), accounting for statistical changes from previous measurements, accounting for statistical changes from expected results, accounting for unexpected results, combinations thereof, and/or the like.

At step 950, a determination of whether the first analyte data and the second analyte data exceed a threshold is performed. If the determination is positive, then the first analyte data and the second analyte data may be employed to determine calibration data 775 at step 960.

Calibration data 775 may be employed by an analyte monitoring system 700 to correct, at least in part, analyte monitoring sensor 720 measurements. The correction may be applied directly to analyte monitoring sensor 720 or to data obtained from analyte monitoring sensor 720. Applying the correction directly to analyte monitoring sensor 720 may comprise, downloading at least some of the calibration data 775 to the analyte monitoring sensor 720. Applying the correction to data obtained from analyte monitoring sensor 720 may comprise communicating calibration data 775 to one or more of the analyte monitoring devices (741, 742 . . . 749).

According to various embodiments, calibration data 775 may be pre-calibration data, post calibration data, interim calibration data, combinations thereof, and/or the like. Pre-calibration data may be calibration data 775 configured to be applied to sensor 720 prior to taking measurement. Post-calibration data may be calibration data 775 configured to be applied to analyte data 773 after analyte measurements are obtained. Interim calibration data may be calibration data 775 configured to be applied to analyte data during analyte measurement acquisition.

According to various embodiments, calibration data 775 may be derived using numerous techniques such as applying statistics to collected analyte data 773. The statistics may be applied, for example, to normalized data, preexisting data, idealized data, prior measured data, currently measured data, combinations thereof, and/or the like. Statistics may require a minimum number of samples. Some of the statistics may comprise the application of calculations comprising standard deviations, variances, means, least squares, regression, Bayesian probabilities, combinations thereof, and/or the like.

According to various embodiments, calibration data 775 may comprise sensor 720 correction data. The correction data may be applied to correct (and/or modify) known measurements from a particular sensor. Correction data may be applied as, for example, offset data and or curve data. Offset data may shift incorrect sensor data to be correct. For example, if a sensor 720 consistently reports analyte data that is consistently low by one percent, the offset data may be applied to increase the measured data to compensate for this known error. Curve data may be applicable when there is a known error that may be mapped as a function, either mathematically and/or discretely. Curve data may also be useful to correct linear and non-linear relationships between sensor measurements and real values.

Calibration data 775 may comprise various types of data according to various embodiments. For example, calibration data 775 may comprise at least one of the following: quality data, timestamp data, data identifier(s), condition data; location data, calibration phase data; calibration phase transition data, calibration schedule data, calibration readiness value(s), reporting data, updated information, interface, notification data, alarm data, alert data, number of calibration measurements, sensor replacement data, ambient light data, explant information, combinations thereof, and/or the like. Calibration readiness value(s) may be employed to indicate good periods to perform a calibration. Reporting data may be employed to indicate reporting factors and information such as touch display report formats, information updates, interface information, combinations thereof, and/or the like. Alarm or alert data may, for example, comprise alarm or alert values such as glucose alarm or alert data indicating when to report errant glucose measurements.

Further, according to some of the various embodiments, calibration data 775 may be merged with data from other sources such as, for example, other measurement devices, medical devices, applications, tracking devices, mobile devices, position tracking devices. So for example, calibration data 775 may be merged with time stamp and location data from a source that is configured to provide time and position information (e.g. a global positioning system (GPS) capable device). Similarly, according to some of the various embodiments, calibration data 775 may be merged with health data 774. Health data 774 may comprise, but is not limited to: food data, exercise data, well-being data, fitness data, medicine data, notification data, reminder data, scheduling data, sleep data, alert data, settings, preferences, calibration data, device health data, combinations thereof, and/or the like.

Figure 10:
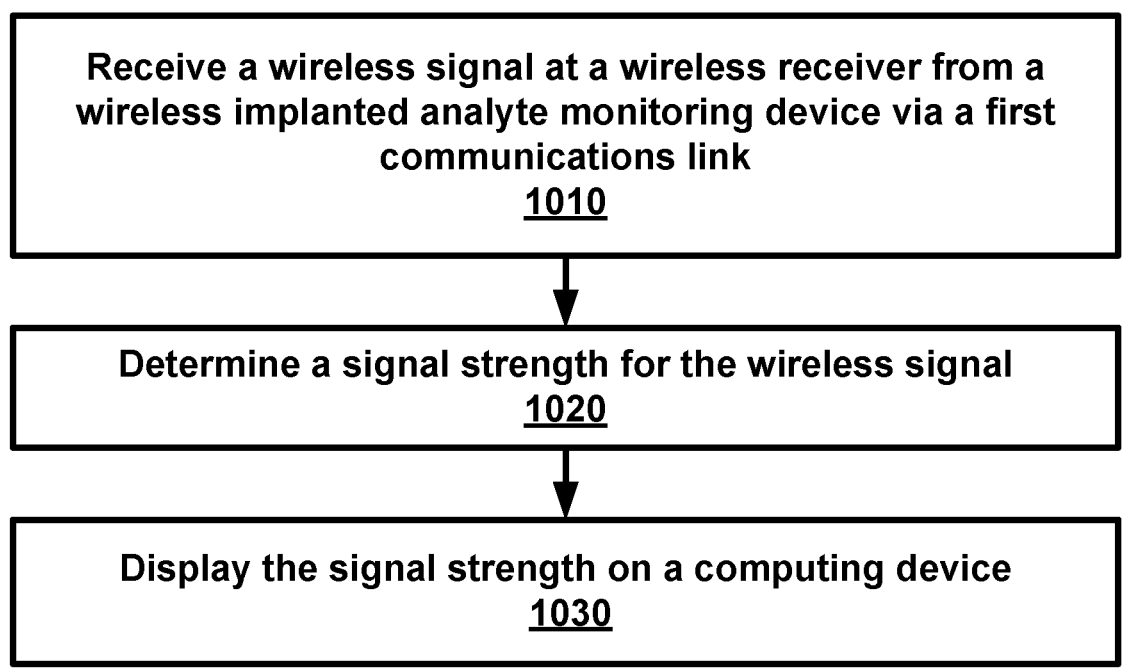
FIG. 10 is a flow diagram illustrating signal strength measurements between a wireless analyte monitoring sensor and an externally located transceiver in accordance with aspects of various embodiments of the present invention.

FIG. 10 is a flow diagram illustrating signal strength measurements between an analyte monitoring sensor 720 and an externally located transceiver 730 in accordance with aspects of various embodiments of the present invention. The analyte monitoring sensor 720 may be a wireless, implantable sensor that is, for example, implanted in a living being subcutaneously.

According to some of the various embodiments, a non-transitory tangible computer readable medium comprising computer readable instruction may be configured to cause one or more processors in a computing device to perform a process to determine the signal strength of an analyte monitoring sensor 720 at the location of a transceiver 730. At step 1010, a signal (e.g., a wireless signal) may be received at a transceiver 730 from an analyte monitoring sensor 720 via a first communications link 725.

A signal strength may be determined for the signal at step 1020. Signal strength may refer to the magnitude of a transmission signal at a reference point that is at a distance from the transmitter. According to some of the various embodiments, the transmission signal may comprise an electric and/or magnetic field. According to other embodiments, other types of signal transmission signals may be employed, such as, for example, a light signal (visible and/or invisible), a vibration signal (e.g. sonic), combinations thereof, and/or the like. Other examples of wireless receivers that may be included in transceiver 730 may comprise a near field communication (NFC) receiver, a Wi-Fi receiver, an infrared receiver, an induction loop, an RF ID tag transducer, combinations thereof, and/or the like. Electric field signals may be expressed in voltage per length or signal power received by a reference antenna. For low-power systems, such as mobile phones, signal strength may be expressed in dB-microvolts per meter (dBµV/m) or in decibels above a reference level of one milliwatt (dBm). According to some of the various embodiments, the wireless receiver may be part of a transceiver. In other words, the wireless receiver may be integrated with a transmitter.

The transceiver may be integrated with a computing device, such as for example, a mobile device. The transceiver 730 may also be configured to provide power to the analyte monitoring sensor 720, which may be a wireless sensor. One mechanism to provide power to the analyte monitoring sensor 720 is via induction.

The transceiver 730 may communicate with the computing device (741, 742 . . . 749) via another communications link 735 such as a cellular communications link. The cellular communications link may be established via a device such as a cell phone, a smart phone, a tablet, a small personal computer, combinations thereof, and/or the like. According to some of the various embodiments, communications link 735 may comprise a wireless link, a wired link, a networked link, combinations thereof, and/or the like. Similarly, according to some of the various embodiments, the computing device (741, 742 . . . 749) may comprise a medical device such as, but not limited to: an ultrasound machine, an x-ray machine, a fluorometer, an MM, other specialized medical device, combinations thereof, and/or the like. According to yet other embodiments, the computing device (741, 742 . . . 749) may comprise a computing device such as, but not limited to: a computer, a server, combinations thereof, and/or the like. The signal strength may be presented on a computing device at step 1030. The presentation may be on one or more user interfaces 778 (e.g., a touch screen display) on the computing device.

Figure 11:
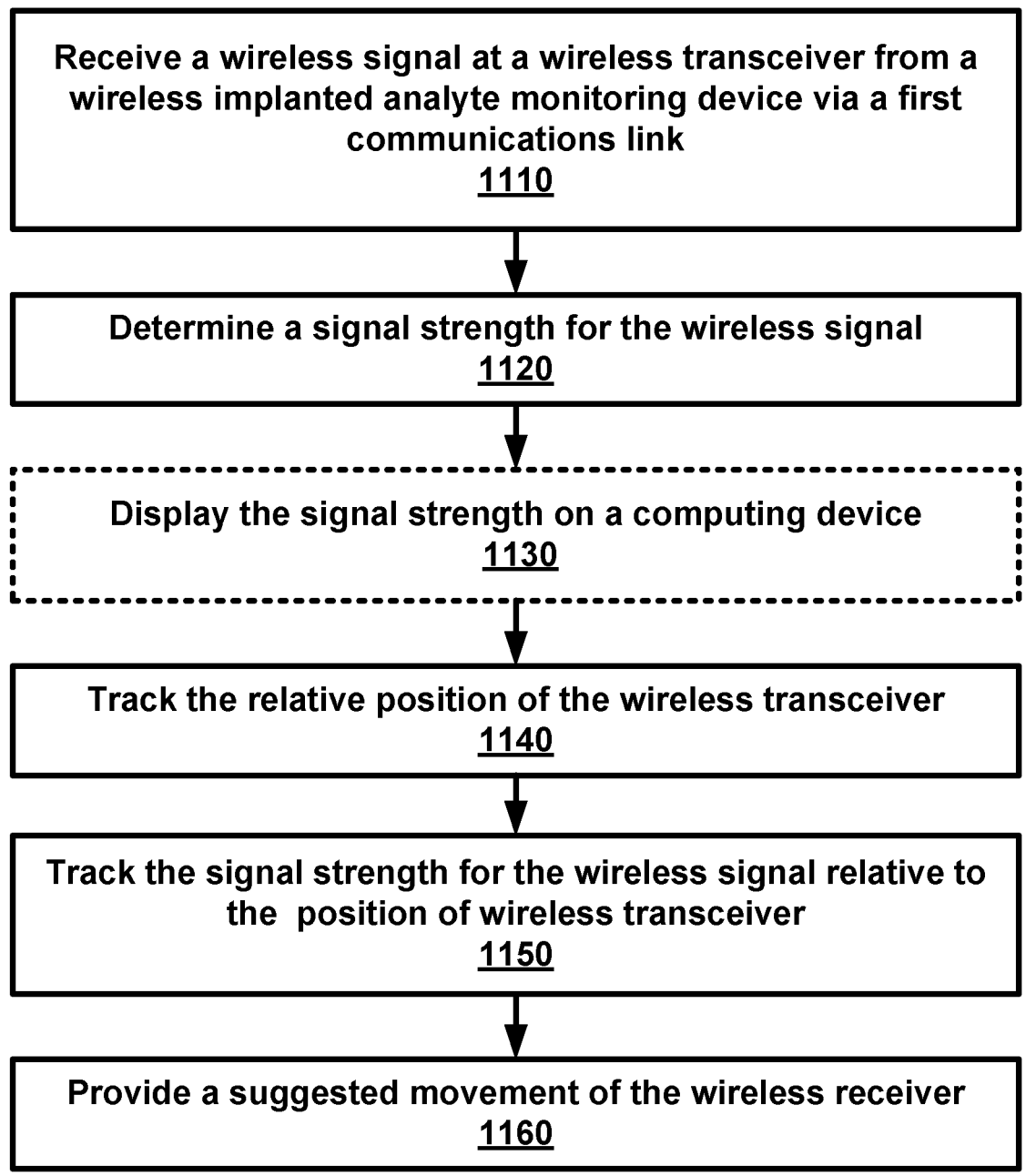
FIG. 11 is a flow diagram illustrating position determination of a wireless analyte monitoring sensor with respect to an externally located transceiver in accordance with aspects of various embodiments of the present invention.

FIG. 11 is a flow diagram illustrating position determination of an analyte monitoring sensor 720 with respect to an externally located transceiver 730 in accordance with aspects of various embodiments of the present invention. This figure illustrates variants of some of various embodiments for positioning transceiver 730 with respect to analyte monitoring sensor 720. According to some of the various embodiments, a wireless signal may be received at a transceiver 730 from an analyte monitoring sensor 720 via a first communications link 725 at step 1110 and a signal strength for the wireless signal may be determined at step 1120. According to some of the various embodiments, the signal strength may be displayed on a computing device at step 1130 (e.g., via one or more user interfaces 778). The computing device may be, according to some of the various embodiments, the transceiver 730 or may be, according to alternative embodiments, another computing device(s) such as one or more of monitoring device (741, 742 . . . 749).

The position of transceiver 730 may be tracked at step 1140. The position of the transceiver 730 may be tracked employing various devices such as, for example, accelerometer(s), GPS device(s), triangulation device(s), optical processing device(s), temperature device(s), ultrasonic device(s), combinations thereof, and/or the like. Accelerometer(s) may be used to track relative motions of the transceiver. In the embodiments where transceiver 730 is a mobile device, an internal accelerometer may be employed. GPS and/or GPS enhanced devices may be employed to track position. Whereas a GPS may work most effectively outdoors with a first resolution, there are enhanced devices that are configured to provide indoor location information with greater resolution than a conventional GPS. Some of the enhanced GPS devices may work reliably indoors and in zero GPS signal conditions by exploiting data available from the cellular, Wi-Fi_33 and other networks to generate position information 776. Some of these systems may employ triangulation techniques from multiple signal sources. Optical processing devices may use optical signals to track the position of transceiver 730 similar to optical mouse tracking. Temperature devices may look at differences in body temperature to map position. Ultrasonic devices may use ultrasonic signals interacting with a body to track position. The tracked position information 776 may be relative position information or absolute position information.

Signal strength of the wireless signal may be mapped with respect to the tracked position at 1150. According to some of the various embodiments, the tracked signal strength and position information 776 may be with respect to the relative position of the transceiver 730 to the analyte monitoring sensor 720.

Some of the various embodiments may employ the position information 776 and signal strength information 779 to determine locations where the transceiver 730 is likely to operate well. According to some of the various embodiments, suggested movement(s) may be determined to increase signal strength. The suggested movement(s) may be communicated to a user at step 1160. According to some of the various embodiments, the suggested movements may be communicated to the user via a display. Depending upon specific hardware configurations, the display may reside on the transceiver (e.g. when the transceiver is a mobile device such as a smart phone). According to alternative embodiments, the suggested movements may be communicated to the user via a display on one or more of the monitoring devices (741, 742 . . . 749). Alternative mechanisms of suggesting movement suggestions may employ other interface devices such as audio devices, touch screen devices, tactile feedback devices, speech synthesis devices, fixed monitors, combinations thereof, and/or the like. So for example, a tactile feedback device may be employed in a transceiver 730 to guide a user to a suggested position using vibration queues. This may be helpful when the device is being positioned in poor visual environments.

According to some of the various embodiments, the suggested movements may be configured to maximize the signal strength. According to some of the various embodiments, the suggested movements may be configured to obtain a signal strength that exceeds a threshold. The threshold may be predetermined and/or dynamic. In many situations, the location may be external to the body part containing the analyte monitoring device. In other situations, the location may be on the surface of the body part containing the analyte monitoring device. In yet other embodiments, the location may also be below the body surface. In such a case, the suggested movement may include a depth value. This may be the case when the transceiver 730 is also implanted. This may also be the case when the suggested movement is guiding the removal of an analyte monitoring sensor 720. Additionally, depth may be a factor when considering the communication link transmission characteristics through body materials.

According to some of the various embodiments the suggested movement may be employed for extraction purposes. In such situations, the suggested movements may be configured to locate the position of the analyte monitoring sensor 720 rather than just the location of maximum signal strength. This capability may be useful in extracting and replacing analyte monitoring sensor(s) 720. To locate the position of an analyte, monitoring sensor 720 may employ a predictive mapping based on the multitude of signal strength measurements and locations in combination with known radiation patterns of the analyte monitoring sensor 720.

Figure 12:
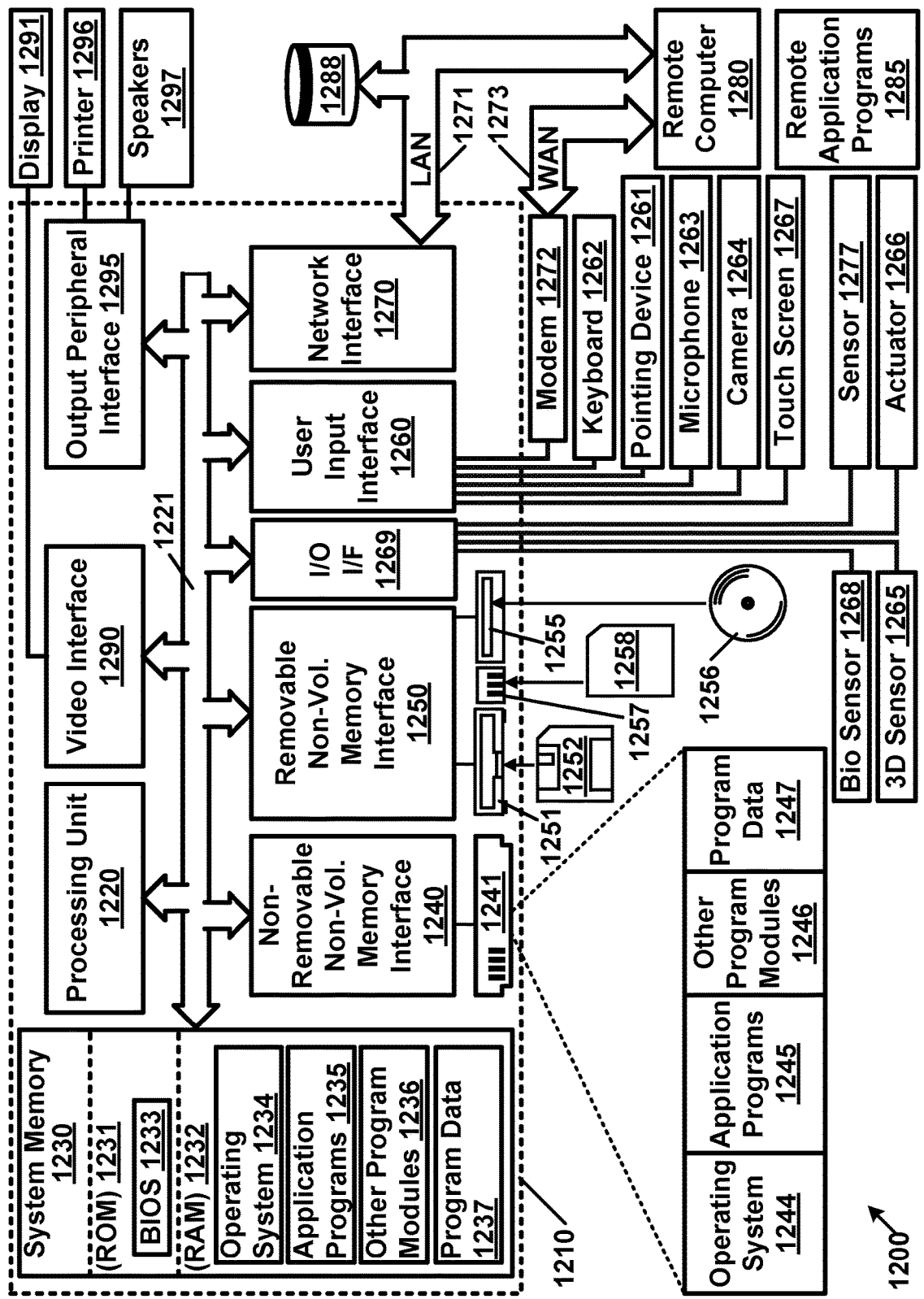
FIG. 12 illustrates an example of a suitable computing system environment on which various aspects of some embodiments may be implemented.

FIG. 12 illustrates an example of a computing system environment 1200 on which aspects of some embodiments may be implemented. The computing system environment 1200 is only one example of a computing environment and is not intended to suggest any limitation as to the scope of use or functionality of the claimed subject matter. Neither should the computing environment 1200 be interpreted as having any dependency or requirement relating to any one or combination of components illustrated in the example operating environment 1200.

Embodiments are operational with numerous other general purpose or special purpose computing system environments or configurations. Examples of well-known computing systems, environments, and/or configurations that may be suitable for use with various embodiments include, but are not limited to, embedded computing systems, personal computers, server computers, mobile devices, hand-held or laptop devices, multiprocessor systems, microprocessor-based systems, set top boxes, programmable consumer electronics, medical device, network PCs, minicomputers, mainframe computers, cloud services, telephonic systems, distributed computing environments that include any of the above systems or devices, and the like.

Embodiments may be described in the general context of computer-executable instructions, such as program modules, being executed by computing capable devices. Generally, program modules include routines, programs, objects, components, data structures, etc. that perform particular tasks or implement particular abstract data types. Some embodiments may be designed to be practiced in distributed computing environments where tasks are performed by remote processing devices that are linked through a communications network. In a distributed computing environment, program modules may be located in both local and remote computer storage media including memory storage devices.

With reference to FIG. 12, an example system for implementing some embodiments includes a computing device 1210. Components of computing device 1210 may include, but are not limited to, a processing unit 1220, a system memory 1230, and a system bus 1221 that couples various system components including the system memory to the processing unit 1220.

Computing device 1210 may comprise a variety of computer readable media. Computer readable media may be any available media that can be accessed by computing device 1210 and includes both volatile and nonvolatile media, and removable and non-removable media. By way of example, and not limitation, computer readable media may comprise computer storage media and communication media. Computer storage media may comprise volatile and/or nonvolatile, and/or removable and/or non-removable media implemented in any method or technology for storage of information such as computer readable instructions, data structures, program modules or other data. Computer storage media comprises, but is not limited to, random access memory (RAM), read-only memory (ROM), electrically erasable programmable read-only memory (EEPROM), flash memory or other memory technology, compact disc read-only memory (CD-ROM), digital versatile disks (DVD) or other optical disk storage, magnetic cassettes, magnetic tape, magnetic disk storage or other magnetic storage devices, or any other medium which can be used to store the desired information and which can be accessed by computing device 1210. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media configured to communicate modulated data signal(s). Combinations of any of the above should also be included within the scope of computer readable media.

The system memory 1230 includes computer storage media in the form of volatile and/or nonvolatile memory such as ROM 1231 and RAM 1232. A basic input/output system 1233 (BIOS), containing the basic routines that help to transfer information between elements within computing device 1210, such as during start-up, is typically stored in ROM 1231. RAM 1232 typically contains data and/or program modules that are immediately accessible to and/or presently being operated on by processing unit 1220. By way of example, and not limitation, FIG. 12 illustrates operating system 1234, application programs 1235, other program modules 1236, and program data 1237 that may be stored in RAM 1232.

Computing device 1210 may also include other removable/non-removable volatile/nonvolatile computer storage media. By way of example only, FIG. 12 illustrates a hard disk drive 1241 that reads from or writes to non-removable, nonvolatile magnetic media, a magnetic disk drive 1251 that reads from or writes to a removable, nonvolatile magnetic disk 1252, a flash drive reader 1257 that reads flash drive 1258, and an optical disk drive 1255 that reads from or writes to a removable, nonvolatile optical disk 1256 such as a Compact Disc Read Only Memory (CD ROM), Digital Versatile Disc (DVD), Blue-ray Disc™ (BD) or other optical media. Other removable/non-removable, volatile/nonvolatile computer storage media that can be used in the example operating environment include, but are not limited to, magnetic tape cassettes, flash memory cards, digital versatile disks, digital video tape, solid state RAM, solid state ROM, and the like. The hard disk drive 1241 is typically connected to the system bus 1221 through a non-removable memory interface such as interface 1240, and magnetic disk drive 1251 and optical disk drive 1255 are typically connected to the system bus 1221 by a removable memory interface, such as interface 1250.

The drives and their associated computer storage media discussed above and illustrated in FIG. 12 provide storage of computer readable instructions, data structures, program modules and other data for the computing device 1210. In FIG. 12, for example, hard disk drive 1241 is illustrated as storing operating system 1244, application programs 1245, program data 1247, and other program modules 1246. Additionally, for example, non-volatile memory may include instructions, for example, to discover and configure IT device(s); to create device neutral user interface command(s); combinations thereof, and/or the like.

A user may enter commands and information into the computing device 1210 through input devices such as a keyboard 1262, a microphone 1263, a camera 1264, touch screen 1267, and a pointing device 1261, such as a mouse, trackball or touch pad. These and other input devices are often connected to the processing unit 1220 through a user input interface 1260 that is coupled to the system bus, but may be connected by other interface and bus structures, such as a parallel port, a game port and/or a universal serial bus (USB).

Sensors and actuators, such as biosensor 1268, 3D sensor 1265, sensor 1277 and actuator 1266 may be connected to the system bus 1221 via an Input/Output Interface (I/O I/F) 1269. Examples of 3D sensor(s) 1265 comprise an accelerometer, an inertial navigation unit, a 3D digitizer, and/or the like. A monitor 1291 or other type of display device may also connect to the system bus 1221 via an interface, such as a video interface 1290. Other devices, such as, for example, speakers 1297 and printer 1296 may be connected to the system via peripheral interface 1295.

The computing device 1210 may be operated in a networked environment using logical connections to one or more remote computers, such as a remote computer 1280. The remote computer 1280 may be a personal computer, a mobile device, a hand-held device, a server, a router, a network PC, a medical device, a peer device or other common network node, and typically includes many or all of the elements described above relative to the computing device 1210. The logical connections depicted in FIG. 12 include a local area network (LAN) 1271 and a wide area network (WAN) 1273, but may also include other networks such as, for example, a cellular network. Such networking environments are commonplace in offices, enterprise-wide computer networks, intranets and the Internet.

When used in a LAN networking environment, the computing device 1210 is connected to the LAN 1271 through a network interface or adapter 1270. When used in a WAN networking environment, the computing device 1210 typically includes a modem 1272 or other means for establishing communications over the WAN 1273, such as the Internet. The modem 1272, which may be internal or external, may be connected to the system bus 1221 via the user input interface 1260, or other appropriate mechanism. The modem 1272 may be wired or wireless. Examples of wireless devices may comprise, but are limited to: Wi-Fi, Near-field Communication (NFC) and Bluetooth™. In a networked environment, program modules depicted relative to the computing device 1210, or portions thereof, may be stored in the remote memory storage device 1288. By way of example, and not limitation, FIG. 12 illustrates remote application programs 1285 as residing on remote computer 1280. It will be appreciated that the network connections shown are exemplary and other means of establishing a communications link between the computers may be used. Additionally, for example, LAN 1271 and WAN 1273 may provide a network interface to communicate with other distributed infrastructure management device(s); with IT device(s); with users remotely accessing the User Input Interface 1260; combinations thereof, and/or the like.

Mobile Medical Application

According to some embodiments, one or more mobile medical applications ("MMA") may be provided, for example, to execute in one or more devices, such as analyte monitoring device 741. In preferred embodiments, the analyte monitoring device 741 may be a standard smart phone, tablet, and/or the like that are commercially available. One or more MMAs may be stored as instructions 772 for execution by one or more processors 771 on analyte monitoring device 741. Where the analyte monitoring device 741 is coupled to a display device, the MMA may cause the analyte monitoring device 741 to provide a series of graphical control elements or widgets in a user interface 778, such as a graphical user interface (GUI), shown on the display device. The MMA may, for example, cause analyte monitoring device 741 to display analyte related information in a GUI 778 such as, but not limited to: one or more of glucose information, current glucose readings, user notifications, glucose status alerts and alarms, trend graphs and arrows, and user-entered events, and may provide one or more graphical control elements that may allow a user to manipulate aspects of the one or more display screens. Although aspects of the MMA are described in the context of glucose monitoring system embodiments, this is not required, and, in some alternative embodiments, the MMA may be employed in other types of analyte monitoring systems.

In some embodiments, an alarm may be a type of notification that may meet a public standard for an alarm. For example, it may include some or any combination of measurable decibel levels, unique patterns, event-specific escalation and de-escalation, fixed repeat intervals, etc. In some embodiments, an alert may be a type of notification that does not need to meet the standard for an alarm. It should be understood that, where alerts or alarms are mentioned herein, an alert may be substituted for an alarm, and an alarm may be substituted for an alert.

In some embodiments where the analyte monitoring device 741 communicates with a transceiver 730, which in turn obtains analyte measurement data from an analyte monitoring sensor 720, the MMA may cause the analyte monitoring device 741 to receive and display one or more of glucose data, trends, graphs, alarms, and alerts from the transceiver 730. In some embodiments, the MMA may store glucose level history and statistics for a patient 710 on the analyte monitoring device 741 and/or in a remote data storage system 760.

In some embodiments, a user 715 of the analyte monitoring device 741, which may be the same or different individual as patient 710, may initiate the download of the MMA from a central repository over a wireless cellular network or packet-switched network, such as the Internet. Different versions of the MMA may be provided to work with different commercial operating systems, such as the Android OS or Apple OS running on commercial smart phones, tablets, and the like. For example, where analyte monitoring device 741 is an Apple iPhone, the user 715 may cause the analyte monitoring device 741 to access the Apple iTunes store to download a MMA compatible with the Apple OS, whereas where analyte monitoring device is an Android mobile device, the user 715 may cause the analyte monitoring device 741 to access the Android App Store to download a MMA compatible with the Android OS.

Pairing the Transceiver and Analyte Monitoring Device

As described above, the analyte monitoring device 741 may communicate with the transceiver 730 through a wired or wireless connection 735 such as, for example, Bluetooth, Wi-Fi_33, and/or the like. In some embodiments, the transceiver 730 may have a button or other user interface element to put the transceiver 730 in "discoverable mode" and thereby enable the analyte monitoring device 741 running a MMA to locate and establish an electronic communication link between the transceiver 730 and analyte monitoring device 741. Alternatively, a user may press the button on the transceiver 730 several times, such as, for example, three, to transition the transceiver 730 to a discoverable mode. The transceiver may additionally or alternatively comprise a user interface that may provide a visual or audio indication to indicate that it is in discoverable mode. For example, a visual interface such as a light emitting diode (LED) on the transceiver 730 may blink a certain number of times and/or change to various colors to indicate the transceiver 730 is in discoverable mode, and/or an audio interface may emit a noise to indicate the same.

When the transceiver 730 is in discoverable mode and the MMA running on analyte monitoring device 741 detects the transceiver 730, a selectable transceiver ID option (e.g., a serial number associated with the transceiver) may be displayed by the MMA on a display of the analyte monitoring device 741. A user 715 may select the transmitter ID option on the GUI in order to select the transceiver 730 associated with the transceiver ID for pairing with the analyte monitoring device 741. In some embodiments, the MMA may display on the GUI a pairing request screen where a user may select an option, such as a button that says "pair," to confirm the pairing of the transceiver 730 with the analyte monitoring device 741. A successful pairing may enable the transceiver 730 to sync glucose or other analyte data stored in and/or collected by the transceiver 730 from analyte monitoring sensor 720 with the analyte monitoring device 741 when the analyte monitoring device 741 is within communication range of the transceiver 730 so that, for example, no glucose or other analyte data will be lost. For example, synchronization of glucose or other analyte data and other information between transceiver 730 and analyte monitoring device 741 may be accomplished using synchronization request messages described above.

In some embodiments, upon a successful pairing of a transceiver 730 with an analyte monitoring device 741 running a MMA, the MMA may prompt the user via the GUI 778 to set one or more calibration times (e.g., morning and evening times for twice a day calibration), at which times the user may receive a notification, described below, for when it is time to perform a calibration entry. In some embodiments, upon a successful pairing of the transceiver 730 with the analyte monitoring device 741 running the MMA, the MMA may prompt the user via the GUI 778 to specify a standard unit of measurement for which glucose values, such as those received from transceiver 730, will be displayed. The standard unit of measurement may or may not be changed once it is set, and, when the unit of measurement may not be changed, the user 715 may have to delete and reinstall the MMA on the analyte monitoring device 741 in order to change the glucose measurement setting.

Linking the Transceiver with a New Sensor

As described above, a communication link 725 may be established between the transceiver 730 and a sensor 720, such as an implantable glucose sensor. The communication link 725 may be established by positioning the transceiver 730 directly over the sensor 720 until electronic communication may be established between the transceiver 730 and sensor 720. In embodiments where the transceiver 730 has a vibratory or visual user interface element, the transceiver 730 may vibrate or flash a LED when a communication link 725 is established between the transceiver 730 and the sensor 720. In addition to or in alternative to the vibratory or visual notification from the transceiver 730, the MMA may display a "New Sensor Detected" message or the like on the GUI 778 of the analyte monitoring device 741.

To link the transceiver 730 with the sensor 720 using the analyte monitoring device 741, a user 715 may select a "Link Sensor" option or the like on a GUI 778 display generated by the MMA. When the sensor 720 and transceiver 730 are successfully linked, the MMA may cause the GUI 778 to display an indication of the successful link, such as a sensor ID number.

In some embodiments, the sensor 720 may require a "Warm-Up Phase" or stabilization period of time, such as 24-hours, in order to stabilize within a patient's 710 body before glucose values can be calculated by the transceiver 730. During such a stabilization period, a patient 710 may not need to secure the transceiver 730 over the sensor 720 initially, but the patient 710 may be prompted by the MMA via a GUI 778 display to link the transceiver 730 with the new sensor 720 to ensure that the transceiver 730 can detect the sensor 720 in order to establish communication. However, if the transceiver 730 is secured over the sensor 720 during the stabilization period, the MMA may display on the GUI 778 a message indicating a "Warm-Up Phase" status or the like of the CGM system and may optionally provide countdown until the end of the stabilization period, such as a 24-hour countdown.

Homescreen of the MMA

Figure 13:
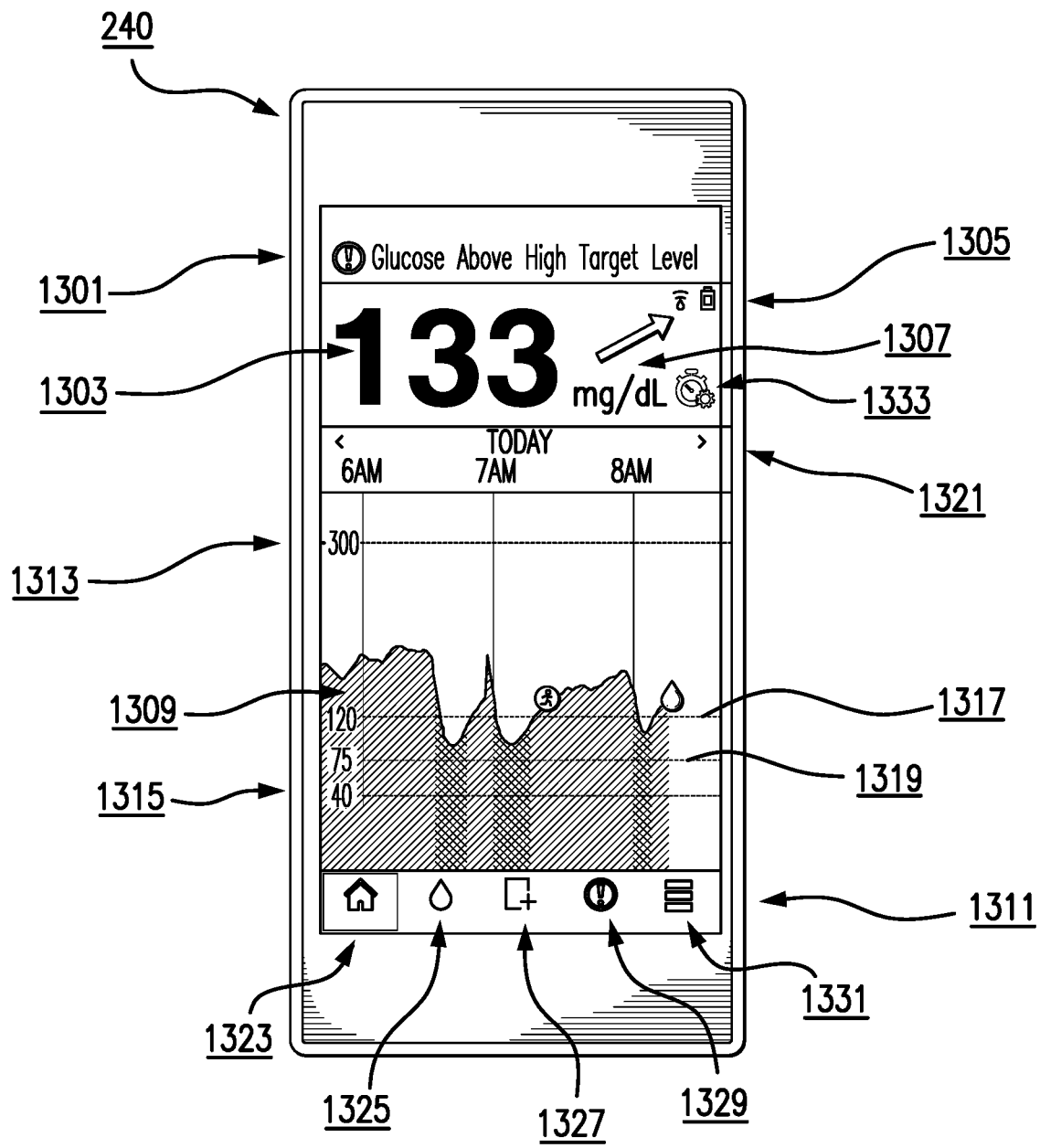
FIG. 13 is an example home screen illustrative display of a medical mobile application in accordance with aspects of various embodiments of the present invention.

FIG. 13 is an example home screen illustrative display of a medical mobile application in accordance with aspects of various embodiments of the present invention. According to some embodiments, the illustrative workspace display of the MMA may be depicted in a GUI 778 on a display connected to an analyte monitoring device 741, such as a mobile device. In some embodiments, the home screen may display one or more of real-time analyte or glucose measurements from transceiver 730 and/or sensor 720, rate and direction of analyte or glucose level change, graphical trends of analyte or glucose levels, alarms or alerts for hypoglycemia or hyperglycemia, and log events such as meals, exercise, and medications. Table 1 below depicts several informational non-limiting examples of items and features that may be depicted on the home screen.

TABLE 1

| Home Screen | |
|---|---|
| Status bar | Shows the status of user's glucose level |
| Transceiver/ Transmitter ID | This is the transceiver being used; the transceiver name can be changed by going to Settings > System |
| Current glucose value | A real-time glucose reading; this may be updated every 5 minutes |
| Date and time | The current date and time with navigational options, such as scroll left or right to see different dates and times |
| Alarm and Events | Shows an icon when an alert, alarm, or event occurs |
| Bluetooth Connection | Shows the strength of the Bluetooth connection 735 |
| Handheld Device Battery Level | Indicates the battery strength of the handheld device |
| Transmitter/ Transceiver Battery Level | Indicates the battery strength of the transceiver |
| Transmitter/ Transceiver Connection Status Icon | Shows the strength of the transceiver connection 725 |
| Trend Arrow | Shows the direction a patient's 710 glucose level is trending |
| Unit of Measurement | This is the units for the glucose value |
| High Glucose Alarm Level | This is the high glucose alarm or alert level set by a user 715 |
| Glucose High Target Level | This is the high glucose target level set by a user 715 |
| Stacked Alerts | Shows when there are several alerts at the same time |
| Glucose Trend Graph | A user 715 can navigate or scroll through the graph to see the trend over time |
| Menu | Navigation to various sections of the MMA, such as: Home    Reports    Settings Calibrate    Share My Data    About Notifications    Placement Guide Event Log    Connect |
| Calibration Point Icon | This icon appears when a calibration is entered |
| Profile Indicator | This indicator may indicate what profile is being applied, such as a normal profile, temporary profile, vacation profile, and the like. |

An example home screen generated by the MMA for display on a GUI 778 is depicted in FIG. 13. As shown in FIG. 13, the home screen may comprise one or more of: a status notification bar 1301 that may depict, for example, alarms, alerts, and notifications related to, for example, glucose levels and system statistics and/or status; a real-time current glucose level 1303 of a patient 710; one or more icons representing sensor 720 or transmitter/transceiver 730 signal strength and transmitter/transceiver 720 battery level 1305; a trend arrow 1307 reflecting a rate and/or direction of change in glucose measurements of a patient 710; a historical graph, such a line graph, 1309 reflecting trends of glucose measurement levels of a patient 710; a profile indicator 133; and navigation tools 1311 that allow a user to navigate through different areas or screens that may be generated in the GUI 778 by the MMA, such as "Home," "Calibrate," "Event Log," "Notifications," and "Menu" screens.

The historical graph 1309 may depict logged events and/or user 715 inputted activities such as meals (nutrition, amount of carbohydrates), exercise (amount of exercise), medication (amount of insulin units), and blood glucose values as icons on positions of the graph corresponding to when such events occurred. The historical graph 1309 may further show one or more of a boundary or indication of a high glucose alarm level 1313, a low glucose alarm level 1315, a high glucose target level 1317, and a low glucose target level 1319, described in further detail below. In some embodiments, a user 715 may interact with a time or date range 1321 option via GUI 778 to adjust the time period of the glucose level displayed on the historical graph 1309. The date range 1321 may be specified by a user 715 and may bet set to different time periods such as 1, 3, 24 hours, 1, 7, 14, 30, and 60 days, weeks, months, etc. In some embodiments, the line graph 1309 may show high, low, and average glucose levels of a patient 710 for the selected date range 1321. In other embodiments, the line graph 1309 may be a pie chart, log book, modal day, or other depiction of glucose levels of a patient 710 over a selectable date range 1321, any of which may further depict high, low, and average glucose levels of the patient 710 over that date range 1321.

In some embodiments, the trend arrow 1307 may be depicted in five different configurations that signify direction (up, down, neutral) and rate (rapidly, very rapidly slow, slow, very slow, and stable) of glucose change. In some embodiments, the MMA and/or the transceiver 730 uses the last twenty minutes of continuous glucose measurement data received from the sensor 720 and/or processed by the transceiver 730 in the calculation used to determine the orientation of the trend arrow 1307. In some embodiments, there may be times when the trend arrow 1307 may not be displayed due to, for example, there being insufficient sensor values available for the trend calculation. In some embodiments, a trend arrow 1307 displayed in a horizontal orientation (approximately 0° along the horizontal direction of the GUI 778 display) may indicate that the glucose level is changing gradually, such as, for example, at a rate between −1.0 mg/dL and 1.0 mg/dL per minute. In some embodiments, a trend arrow 1307 displayed slightly in the upwards direction (approximately 45° up from the horizontal direction of the GUI 778 display) may indicate that the glucose level is rising moderately, such as, for example, at a rate between 1.0 mg/dL and 2.0 mg/dL per minute. In some embodiments, a trend arrow 1307 displayed slightly in the downwards direction (approximately 45° down from the horizontal direction of the GUI 778 display) may indicate that the glucose level is falling moderately, such as, for example, at a rate between 1.0 mg/dL and 2.0 mg/dL per minute. In some embodiments, a trend arrow 1307 displayed in a vertical direction (approximately 90° up from the horizontal direction of the GUI 778 display) may indicate that the glucose level is rising very rapidly, such as, for example, at a rate more than 2.0 mg/dL per minute. In some embodiments, a trend arrow 1307 displayed in a downwards direction (approximately 90° down from the horizontal direction of the GUI 778 display) may indicate that the glucose level is falling very rapidly, such as, for example, at a rate more than 2.0 mg/dL per minute. In some embodiments, the trend arrow 1307 is different from a predicted glucose alarm or alert. For example, the trend arrow 1307 may indicate rate and direction of change regardless of glucose value, whereas predicted glucose alarms or alerts may indicate reaching a certain glucose level based on current trends. For example, the MMA may cause a predicted low glucose alarm or alert to be displayed in the notification bar 1301 while still displaying a relatively stable trend arrow 1307 (e.g., at 0° or 45° from the horizontal direction of the GUI 778 display).

In some embodiments, the MMA may cause the analyte monitoring device 741 to provide auditory readings of the information items depicted on the home screen, for example, to allow users 715 who are visually impaired and/or illiterate to use the MMA and analyte monitoring device 741. For example, the MMA may cause the analyte monitoring device 741 provide an auditory reading via an audio interface 778 of the current glucose level 1303, trend arrow 1307, any alerts or alarms displayed in status notification bar 1301, as well as other information items on the home screen of the MMA.

In some embodiments, the historical line graph 1309 may allow user 715 to quickly review and analyze historical data and/or trend information of a patient's 710 sensor glucose measurement values over time. In some embodiments, the historical line graph 1309 may include icons or markers along the trend line to reflect alarms, alerts, notifications, and/or any events that were automatically or manually logged by the user 715 into the analyte monitoring device 741 via a GUI 778 display generated by the MMA. Where one or more of such icons or markers are displayed on the historical line graph 1309, a user 715 may select any one of the icons or markers to obtain more information about the item. For example, in response to a selection of a mark on the line graph 1309, the GUI 778 may generate a popup window on the display that provides more information about the mark.

In some embodiments, the historical line graph 1309 may enable a user 715 to quickly review how well a patient 710 is doing against glucose targets and/or alarms or alerts. For example, as described in further detail below, a user 715 may establish a high glucose alarm level 1313 and/or a low glucose alarm level 1315, as well as a high glucose target level 1317 and/or a low glucose target level 1319. The high glucose alarm level 1313 and/or low glucose alarm level 1315 may be visually depicted over the historical line graph 1309, for example, using a colored dashed line (such as red). Additionally, the high glucose target level 1317 and low glucose target level 1319 may be visually depicted over the historical line graph 1309, for example, using a color dashed line (such as green).

In some embodiments, the colors of the historical line graph 1309 may change depending on a glucose level 1303 status. For example, during the times where the glucose level 1303 was outside of the high glucose alarm level 1313 or low glucose alarm level 1315, then the portion of the line graph 1309 corresponding to those times may be filled in red. As another example, during the times where the glucose level 1303 is between the high glucose target level 1317 and the low glucose target level 1319, then the portion of the line graph 1309 corresponding to those times may be filled in green. As yet another example, during the times where the glucose level 1303 is between a glucose target level 1317, 1319 and a corresponding alarm level 1313, 1315, then the portion of the line graph 1309 may be filled in yellow.

In some embodiments, the line graph 1309 may be displayed with one or more selectable date range icons 1321 that allow a user 715 to change the day/time period corresponding to the line graph 1309 in real-time. For example, a user 715 may select a forwards or backwards selectable option (such as an arrow) or use a swipe or fling gesture that may be recognized by GUI 778 to navigate to a later or earlier time period, respectively, such as a day, month, etc. In some embodiments a user 715 may choose an older graph 1309 to display by tapping the date on the date range 1321 portion of the screen and submitting or entering a desired date and/or time to review. In some embodiments, a user 715 may use one or more gestures that are recognized by the GUI 778, such as a pinch, zoom, tap, press and hold, or swipe, on graph 1309. For example, a user 715 may pinch the historical line graph 1309 with a thumb and index finger in order to cause the MMA to display different time/dating settings or adjust a time/date setting on the line graph 1309. In some embodiments, a user 715 may tap or press and hold a time event on historical line graph 1309, and in response the MMA may display further detail on the time event, such as a history, reading value, date/time, or association to other events or display a prompt for entry of a time event.

In some embodiments, the MMA may store glucose data 1303 on the analyte monitoring device 741 so long as there is available memory space. Additionally or alternatively, the MMA may cause the analyte monitoring device 741 to send a sync request message to store the glucose data 1303 on a remote storage device 760.

In some embodiments, the MMA will cause the GUI 778 to display navigational tools 1311 that allow a user 715 to navigate to different features and screens provided by the MMA. For example, the navigational tools 1311 may comprise a navigation bar with a plurality of selectable navigation options 1323, 1325, 1327, 1329, and 1331, such as buttons or icons. As shown in FIG. 13, selectable navigation options may allow a user to navigate to the "Home" screen 1323, a "Calibrate" screen 1325, an "Event Log" screen 1327, a "Notifications" screen 1329, and a "Menu" screen 1331. Upon a user selection of one of the selectable navigation options in the navigation tools area 1311, a new screen corresponding to the selected option may be displayed on a display device by the GUI 778.

Calibration Using the MMA

Figure 21:
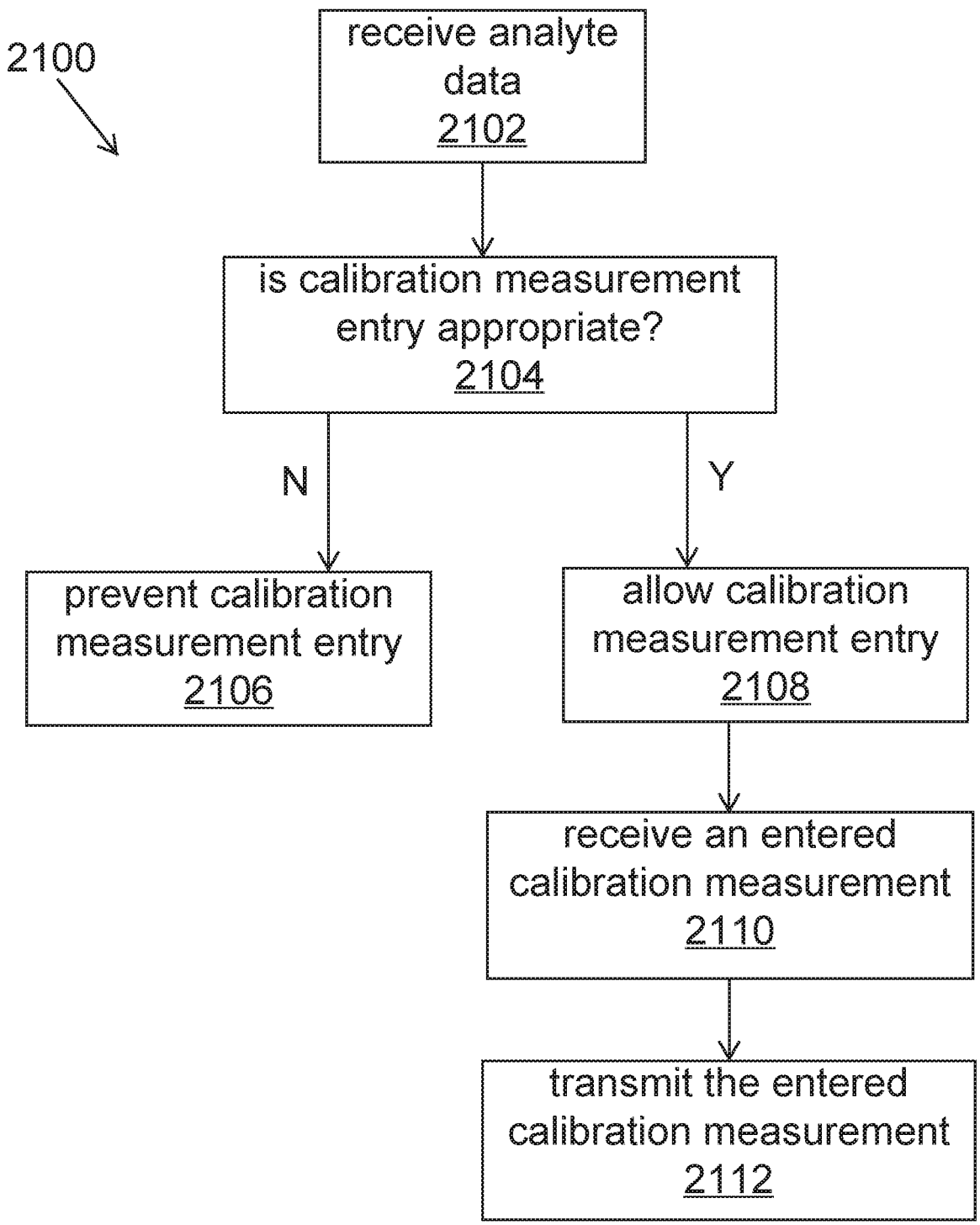
FIGS. 21 is a flow diagram illustrating a calibration process in accordance with various embodiments of the present invention.

To help ensure accuracy of the CGM system, the CGM system may require periodic calibration to fingerstick readings obtained from a blood glucose meter (BGM). FIG. 21 is a flow diagram illustrating a calibration process 2100 according to some embodiments. In some embodiments, the process 2100 may be performed by the analyte monitoring device 741. In some embodiments, the process 2100 may include a step 2102 of receiving analyte data. In some embodiments, as in steps 810 and 910 of the flow diagram of FIGS. 8 and 9, the analyte data may be received over the communications link 735 from at least one first device (e.g., transceiver 730). In some embodiments, the process 2100 may include a step 2104 of determining whether or not calibration measurement entry is appropriate. In some embodiments, the process 2100 may include a step 2106 of, in response to determining that calibration measurement entry is not appropriate, preventing calibration measurement entry. In some embodiments, the process 2100 may include a step 2108 of, in response to determining that calibration measurement entry is appropriate, allowing calibration measurement entry. In some embodiments, the process 2100 may include a step 2110 of receiving an entered calibration measurement. In some embodiments, the process 2100 may include a step 2112 of transmitting the entered calibration measurement. In some embodiments, the calibration measurement may be transmitted over the communications link 735 to the at least one first device (e.g., transceiver 730). In some embodiments, any commercially available BGM may be used and the readings may be submitted to the transceiver 730 via a GUI 778 provided by the MMA on the analyte monitoring device 741. For example, a user 715 may manually enter a BGM measurement into a MMA calibration screen, which in turn may be transmitted by the analyte monitoring device 741 to transceiver 730 for calibration.

In some embodiments, the CGM system may enter different phases of calibration. For example, the CGM system may require an initialization phase of calibration that may span the first twenty-four hours after sensor 720 insertion into a patient 710. In some embodiments, four fingerstick BGM calibration measurements may be required in the initialization phase. In some embodiments, the initialization phase may require the patient 710 to perform each of the four fingerstick BGM tests 2-12 hours apart. However, if more than 12 hours pass between any of the four initialization phase calibrations, then the twenty-four hour period for the initialization may restart and the four fingerstick BGM tests, each 2-12 hours apart, may again be required from the patient 710.

As another example, the system may enter a daily calibration phase, such as after an initialization phase terminates (e.g., after a twenty-four hour initialization phase period). In some embodiments, the MMA may indicate that the system is entering a daily calibration phase by displaying on the GUI 778 a daily calibration notice after successful completion of the initialization phase. In the daily calibration phase, only two calibration measurements may be required daily from the patient 710 during the life of the sensor. For example, the daily calibration phase may require obtaining and entering two BGM measurement values from a patient 710 at a scheduled morning and evening calibration time. While a user 715 of the MMA may define the two daily calibration times, it may be preferred that the calibration times are at a minimum of ten hours apart and a maximum of fourteen apart.

In some embodiments, if a daily calibration is missed, then the MMA may cause the GUI 778 for the home screen to stop displaying the real-time glucose level 1303 after a certain time period after the missed calibration (e.g., sixteen hours). In some embodiments, if a calibration is not entered within a predetermined time period (e.g., twenty-four hours) after the last accepted calibration value, then the CGM system may re-enter the initialization phase.

The MMA, via the GUI 778, may automatically alert, alarm, or notify a user 715 when it is time to perform a fingerstick BGM calibration of a patient 710. In some embodiments, a user 715 may set up daily calibration times in the MMA, and may subsequently adjust the daily calibration times by adjusting the daily calibration settings of the MMA.

FIG. 14A is an example calibration notification screen display of a medical mobile application in accordance with aspects of various embodiments of the present invention. As shown in FIG. 14A, a calibration notification popup window 1401 may be displayed on a GUI 778 of the analyte monitoring device 741 by the MMA in order to, for example, notify a user 715 that a fingerstick BGM measurement is required from the patient 710 for calibration. For example, the calibration notification popup window 1401 may be displayed during the daily calibration time or at one or more points during a range of daily calibration times set by a user 715. In some embodiments, the user 715 may select any one of three selectable options on the GUI 778, such as buttons or icons, in connection with calibration notification popup window 1401: 1) defer or delay calibration by selecting a "Not Now" selectable option 1403; 2) perform a calibration by selecting a "Calibrate" selectable option 1407; and/or 3) request more information about the calibration by selecting an information icon 1405.

If calibration is deferred by a user selection 715 of the "Not Now" selectable option 1403 in notification window 1401, then the notification window 1401 may be removed from the display and may be reasserted after a predetermined time interval or a time interval set by the user 715. For example, a new calibration notification window 1401 may be displayed after a certain time interval. In some embodiments, a calibration notification may also be displayed in the status notification bar 1301. In some embodiments, the MMA may allow or accept the calibration measurement from the patient 710 and/or user 715 to be taken up to two hours prior and one hour after a scheduled morning or evening calibration time.

If the information icon 1405 is selected by the user 710, the MMA may generate a popup display of information about calibration to a user in the GUI 778, containing, for example information on a BGM, frequency of fingerstick BGM measurements, time settings for fingerstick BGM measurements, and the like. In some embodiments, no information icon 1405 is displayed in calibration notification window 1401.

In some embodiments, calibration notification 1401 may display a selectable "Calibrate" option 1407 that allows the user 715 to submit a fingerstick BGM measurement to the analyte monitoring device 741 to be used for calibration.

FIG. 14B is an example calibration screen display of a medical mobile application in accordance with aspects of various embodiments of the present invention. Upon selection of the "Calibrate" option 1407, the MMA may cause the GUI 778 display a Calibrate screen 1409b. In some embodiments, the step 2104 of the calibration process 2100 may include determining whether or not the current time is within a calibration window. In some embodiments, if the current time is not within a calibration window (e.g., one hour before or two hours after a scheduled calibration), then (e.g., in the step 2106 of the calibration process 2100)a notification may be displayed on the Calibrate screen 1409b and/or a selectable option "Submit" 1411b may be disabled, thereby preventing a user 715 from entering a fingerstick BGM measurement for calibration. A patient 715 may obtain a fingerstick BGM measurement from any commercially available BGM. Once patient 710 and/or user 715 has obtained a fingerstick BGM measurement, the user 715 may select the selectable "Time" option 1413b and/or the selectable "Glucose" option 1415b on the calibrate screen 1409b to enter the time of day when the fingerstick BGM measurement was taken and the value of that fingerstick BGM measurement, respectively. The calibrate screen 1409b may, in some embodiments, display one or more of a next scheduled calibration time, a number of sensor days remaining reflecting the remaining life of the sensor, and a selectable "Calibration Tips" option 1417b.

In some embodiments (e.g., in the step 2108 of the calibration process 2100), the MMA may enable a user to directly enter a time the fingerstick BGM measurement was taken via the GUI 778, and in other embodiments a selectable "Time" option 1413b may be provided on the GUI 778 such that, when selected, the GUI 778 displays a drop down menu with selectable date/time entries. Likewise, in some embodiments, the MMA may enable a user to directly enter a glucose fingerstick BGM measurement via the GUI 778, and in other embodiments a selectable "Glucose" option 1415b may be provided on the GUI 778 such that, when selected, the GUI 778 displays a drop down menu with selectable glucose value entries.

In some embodiments, upon selection of the "Calibration Tips" option 1417b, the MMA may cause the GUI 778 to display information to help improve calibration. For example, the displayed calibration tips may indicate when calibration will not be ready or accepted, such as, for example: the transceiver 730 had not been worn for at least five minutes before and after attempting to calibrate; the BGM reading is less than or equal to 40 mg/dL; the BGM reading is greater than or equal to 400 mg/dL; the BGM reading was taken more than 5 minutes prior to entering in the MMA; sensor glucose values are changing rapidly, such as greater than 2.5 mg/dL/min; sensor glucose value is significantly different than the BGM reading; and/or it is not yet time for calibration.

FIG. 14C is an example calibration screen display of a medical mobile application in accordance with aspects of various embodiments of the present invention. Once the time and glucose values associated with a BGM measurement are entered into the MMA via the GUI 778, as described above in connection with FIG. 14B, the MMA may display a calibration screen 1409c on the GUI 778 with the entered time and glucose values for verification by a user 715 next to the selectable "Time" 1413c and "Glucose" 1415c options. Thus, a user 715 may confirm that the BGM measurement values were entered correctly before selecting the selectable "Submit" option 1411c that may submit the BGM measurement values for calibration (e.g., from the analyte monitoring device 741 to the transceiver 730).

FIG. 14D is an example calibration confirmation screen display of a medical mobile application in accordance with aspects of various embodiments of the present invention. Upon submission of a BGM measurement as described in connection with FIG. 14C, the MMA may cause the GUI 778 to display a Confirm Calibration screen 1419. Confirm calibration screen 1419 may depict the submitted BGM measurement value for verification by the user 715, and in some embodiments, may display a selectable "Cancel" option 1421 and a selectable "Submit" option 1423. If the calibration measurements are incorrect, the selectable "Cancel" option 1421 may be selected by the user 715, thereby allowing the user 715 to go back to the Calibration screen 1409 as shown in FIGS. 14B-C to modify the entered calibration values. Alternatively, if the calibration measurements are correct, the selectable "Submit" option 1423 may be selected by the user 715 in order to submit the BGM measurements for calibration by the CGM system.

Figures 14E, 14F:
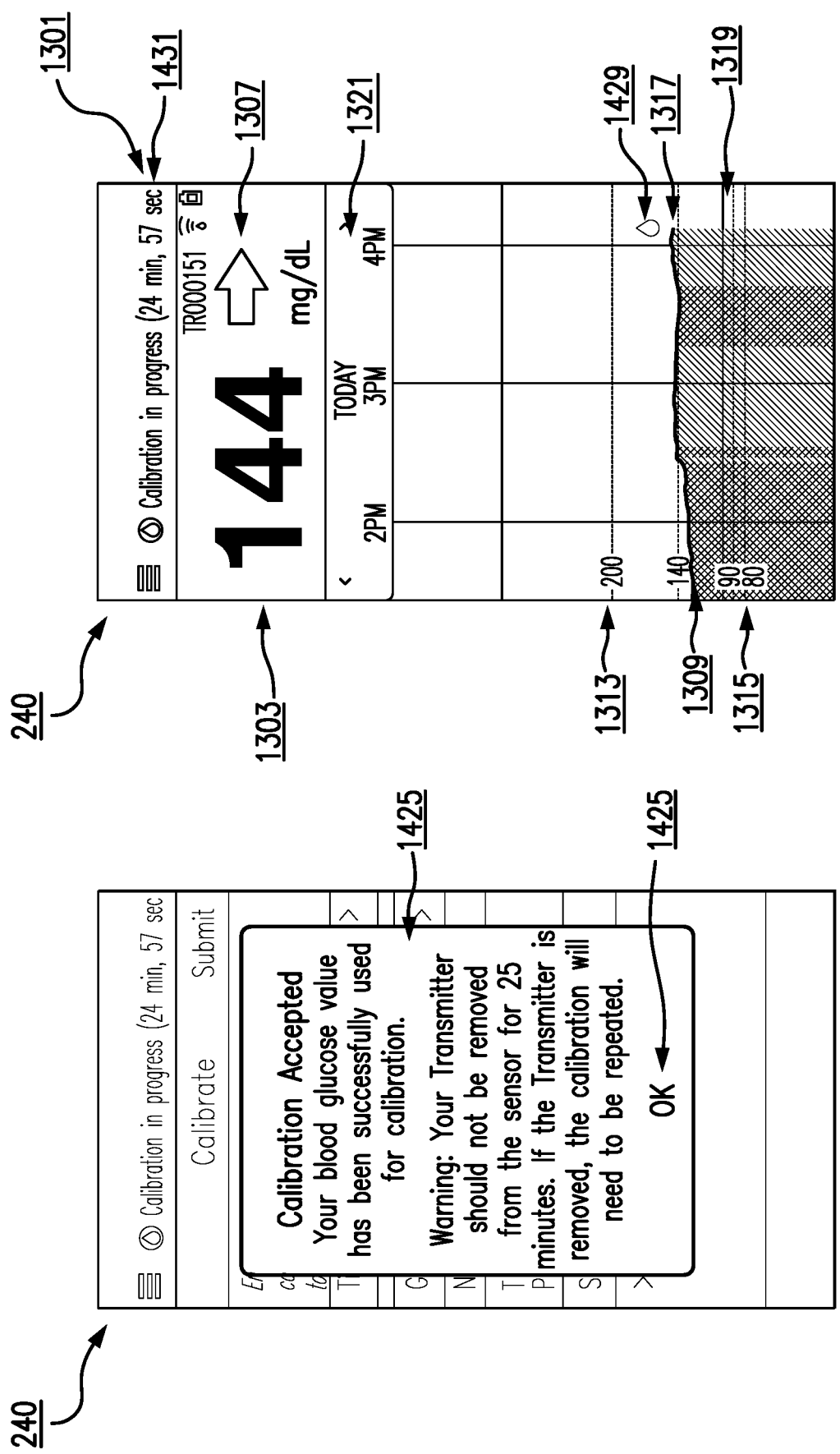
FIG. 14E is an example calibration accepted screen display of a medical mobile application in accordance with aspects of various embodiments of the present invention.
FIG. 14F is an example home screen display of a medical mobile application in accordance with aspects of various embodiments of the present invention.

FIG. 14E is an example calibration accepted screen display of a medical mobile application in accordance with aspects of various embodiments of the present invention. After submission of a BGM measurement for calibration as described above in connection with FIG. 14D, the MMA may cause the GUI 778 to display a calibration accepted screen 1425. As shown in FIG. 14E, the calibration accepted screen 1425 may include information indicating that the BGM measurement was successfully used for calibration by the CGM system. In some embodiments, the calibration accepted screen 1425 may include a warning that the transceiver/transmitter 730 should not be removed from the sensor 720 for a period of time, such as, for example, 25 minutes, to allow the CGM system to obtain sufficient sensor measurements of glucose concentration to perform a successful calibration. In some embodiments, after accepting a BGM measurement, the analyte monitoring device 778 may transmit the BGM measurement to the transceiver 730 for calibration. As shown in FIG. 14E, a selectable "OK" option 1427 may be displayed in the GUI 778, and upon selection of the option 1427, the MMA may cause the GUI 778 to remove the calibration accepted screen 1425 from the display.

In some embodiments, there may be one or more conditions where calibration may not be accepted and/or calibration is not ready for the CGM system. In some embodiments, the step 2104 of the calibration process 2100 may include considering the one or more conditions. In some embodiments (e.g., in the step 2106 of the calibration process 2100), the MMA may prohibit the entry of a BGM measurement from a user 715 and/or delay notification of a scheduled BGM measurement from a user 715 where one or more conditions are met, such as, for example: the transceiver 730 had not been worn for at least five minutes before and after attempting to calibration; the BGM measurement was taken more than five minutes prior to entering in the MMA; sensor glucose values are changing rapidly, such as greater than 2.5 mg/dL/min; and it is not yet time for calibration. According to some aspects, prohibiting entry of a BGM measurement when calibration may not be accepted and/or calibration is not ready may prevent a patient 710 from taking excessive or unnecessary BGM measurements that may not be used for calibration. In some embodiments (e.g., in the step 2108 of the calibration process 2100), the MMA may allow entry of a BGM measurement yet reject the BGM measurement when one or more conditions are met, such as, for example: the BGM measurement is less than or equal to 40 mg/dL, the BGM measurement is greater than or equal to 400 mg/dL, and the BGM measurement was taken more than 5 minutes prior to entering in the MMA.

FIG. 14F is an example home screen display of a medical mobile application in accordance with aspects of various embodiments of the present invention. In some embodiments, the home screen display of FIG. 14F may be displayed in the GUI 778 after a user 715 has submitted a BGM measurement that has been accepted for calibration as described above. Like the home screen depicted in FIG. 13, the home screen depicted in FIG. 14F may include one or more of a status notification bar 1301, a real-time current glucose level of a patient 1303; a trend arrow 1307 reflecting a rate and/or direction of change in glucose measurements; a historical graph, such a line graph, 1309 reflecting trends of glucose measurement levels that includes one or more of a boundary or indication of a high glucose alarm level 1313, a low glucose alarm level 1315, a high glucose target level 1317, and a low glucose target level 1319; and selectable time or date range 1321 of glucose levels to display on the historical graph 1309.

The home screen of FIG. 14F may depict a calibration notification 1431 in status notification bar 1301 that includes an indication that a calibration is in progress by the CGM system. Calibration notification 1431 may display immediately or shortly after a user 715 successfully submits a BGM measurement as described above to the MMA. In some embodiments where the transceiver 730 must remain in communication with the sensor for a predetermined time period (e.g., 25 minutes) to perform a calibration, the calibration notification 1431 may depict a timer or countdown indicating when the time period expires. In some embodiments, the historical line graph 1309 of FIG. 14F may depict an event indicator icon 1429 that indicates that a BGM measurement was submitted for calibration. As shown in FIG. 14F, the event indicator icon 1429 may be a blood drop icon, or some other symbol that allows a user 715 of the MMA to readily identify the event of submitting a BGM measurement for calibration.

MMA Event Screen

Figure 15:
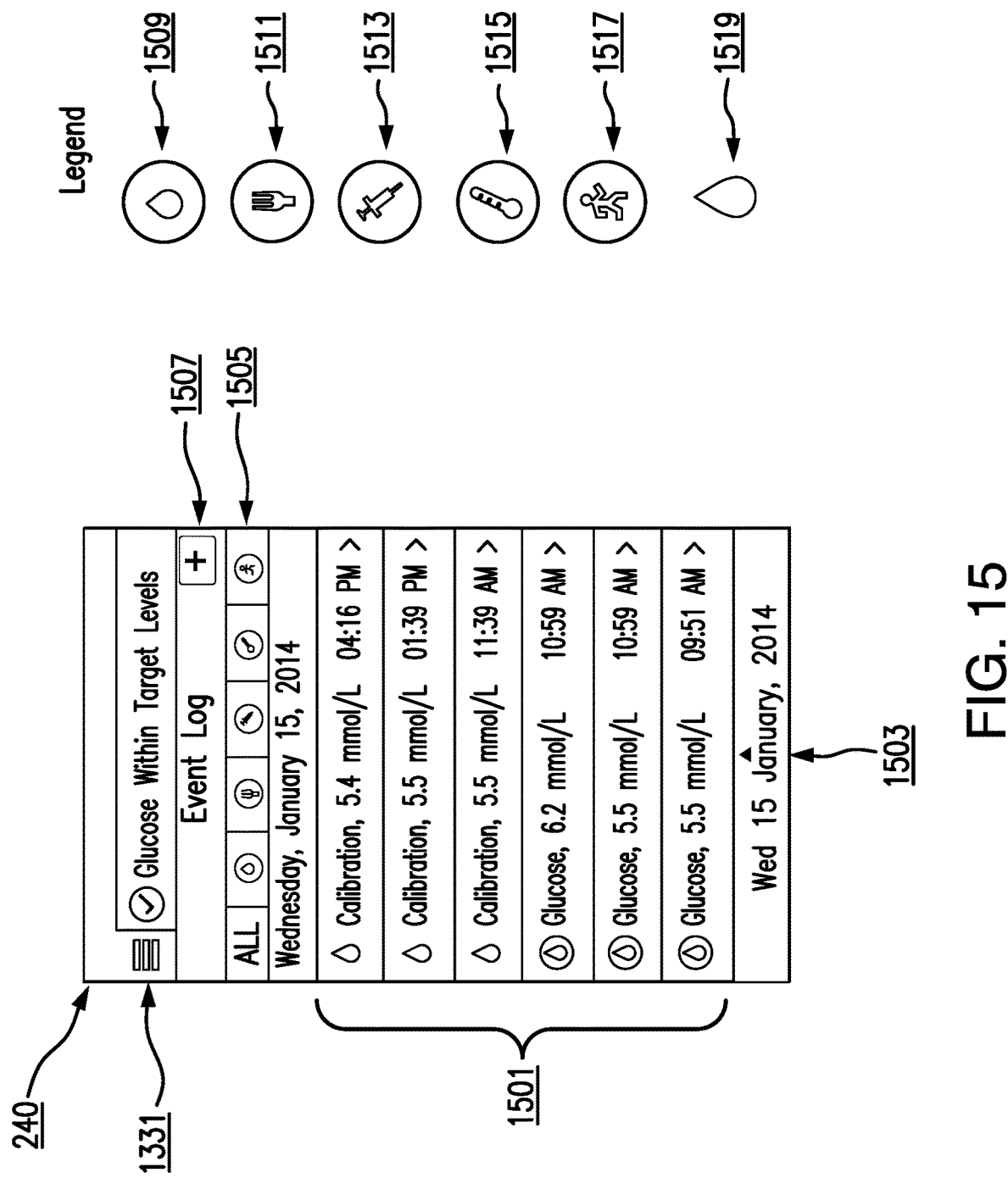
FIG. 15 is an example event screen display of a medical mobile application in accordance with aspects of various embodiments of the present invention.

FIG. 15 is an example event screen display of a medical mobile application in accordance with aspects of various embodiments of the present invention. In some embodiments, a user 715 may navigate to the event screen by selecting an "Event Log" navigational tool 1327 or by using a menu navigation tool 1331 as shown in FIG. 13. In some embodiments, the MMA may cause the GUI 778 to display the menu navigation tool or selectable option 1331 at the upper left corner of the display of the analyte monitoring device in addition to or in alternative to displaying the menu selectable option on the bottom of the display with additional navigation tools 1311. The system may allow a user 715 to log and track a plurality of events in addition to continually monitoring glucose levels of a patient 710. A user 715 may manually enter events, which may appear on the trend graph 1309 and/or in any glucose reports. Such events may assist a user 715/patient 710 in finding patterns in a glucose profile of a patient 710.

As shown in FIG. 15, the event screen may depict an event log 1501 with one or more past events. The event log 1501 may list all or a subset of events entered by a user 715 over a specific time period (e.g., a day, a week, a month, a year, etc.). Where the events in the event log 1501 span beyond the display area of the analyte monitoring device 741, the MMA may configure the GUI 778 to allow a user 715 to use a gesture, such as a scroll or flick, that is recognized by the GUI 778 to navigate through the event entries or configure the GUI 778 to provide a selectable date option 1503 to allow a user 715 to navigate to a different date of events. In some embodiments, each event in the event log 1501 may be selectable in the GUI 778, and upon selection of the event a screen may appear indicating one or more additional details of the event, such as the time, notes, values, measurements, etc. associated with the event.

Each event may correspond to an event type, which may be represented in short-hand with a symbol and/or a specific icon such as those shown in FIG. 15. For example, icon 1509 may indicate a BGM test event, icon 1511 may indicate a meal event, icon 1513 may indicate an insulin dosage event, icon 1515 may indicate a health condition event, icon 1517 may indicate an exercise event, and icon 1519 may indicate a calibration measurement. In some embodiments, different icons may be used to indicate the same or different events as those shown in the legend.

Where the MMA specifies event types, such as those shown in the legend in FIG. 15, the event screen may display a set of one or more selectable filtering options 1505 to filter the types of events displayed in the event log 1501. When the "all" events option is selected by a user 715, all events regardless of type may be displayed in the event log 1501. However, upon the selection of a selectable event filtering option 1505 by a user 715, which may be represented as one or more icons, such as those shown in the legend, only events corresponding to the selected filtering option 1505 may be displayed. For example, if a user 715 selects the icon 1509 corresponding to BGM tests, then the MMA may only display events, if any, that reflect BGM tests in the event log 1501.

In some embodiments, a user 715 may manually add event entries by selecting an add event option 1507. Upon selection by a user 715 of the add event option 1507, the MMA may cause the GUI 778 to prompt the user 715 to specify the type of the event, such as, for example, a BGM test event, a meal event, an insulin dosage event, a health condition event, an exercise event, or the like. After selection by the user of the type of event, the MMA may cause the GUI 778 to display one or more parameters associated with the event. For example, where a patient 710 and/or user 715 takes a blood glucose test outside of a calibration measurement window and wishes to simply log the measurement, the user 715 may select the add event option 1507, select "Glucose" to specify the type of event, and then enter parameters into the GUI 778 associated with the event, such as time, date, glucose value, notes and the like. As another example, for a meal event, a user 715 may enter parameters associated with the event such as time, date, type of meal, carbohydrates, and any notes. As another example, for an insulin dosage event, a user 715 may enter parameters associated with the event such as time, date, units, type of insulin, and notes. As another example, for a health event, a user 715 may enter parameters associated with the event such as time, date, severity (low, medium, high), condition, and notes. As yet another example, for an exercise event, a user 715 may enter parameters associated with the event such as time, date, intensity (low, medium, high), duration, and notes.

In some embodiments, when entering a meal event, the user 715 may be presented with an option to "select from a database" of foods. For example, the user may be able to indicate portion size as a multiplier, and carbohydrate values associated with a selected food item from the database of foods may be used in an event log. In some embodiments, the user may be able to select multiple food items from the food database to compose one "meal" associated with a meal event entry, and the total carbohydrate value for the meal may be used in, for example, the event log.

In some embodiments, the user 715 may be presented with an option to "select from a database" of activity. For example, the user may be able to indicate intensity level and duration associated with the activity item, and the activity item may be used in, for example, the event log.

In some embodiments, one or more different event types may be predefined by the MMA. In some embodiments, a user 715 may be able to customize or define a new event type in addition to or in lieu of any MMA predefined event types.

MMA Notification Screen

Figure 16:
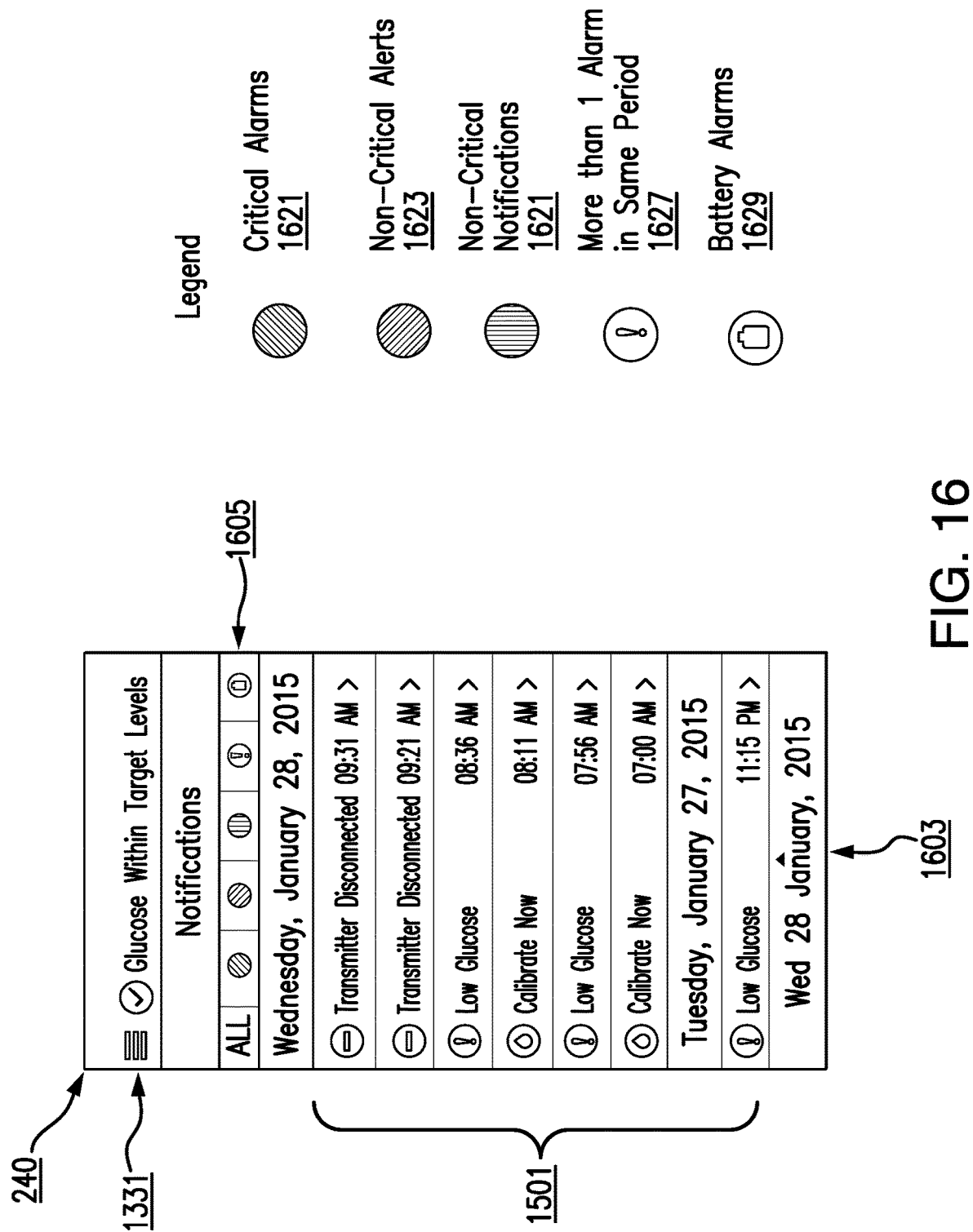
FIG. 16 is an example notification screen display of a medical mobile application in accordance with aspects of various embodiments of the present invention.

FIG. 16 is an example notification screen display of a medical mobile application in accordance with aspects of various embodiments of the present invention. In some embodiments, the notification screen illustrated in FIG. 16 lists alarms, alerts, and notifications that may be generated by the MMA over time, thereby enabling a user 715 to review past messages that may have been missed or to help a user 715 understand more about the glucose status of a patient 710. The notification screen may display alarms, alerts, and notifications in list 1601. In some embodiments, all alarms, alerts, and notifications for a specific date, such as today's date, may be display in list 1601.

Each alarm, alert, or notification in list 1601 may be accompanied by one or more information items, such as a brief textual description, a time and/or date, and an icon that may indicate the type, severity, and/or frequency of the notification, alarm, or alert. In some embodiments, each notification, alert, and/or alarm in the list 1601 may be selectable in the GUI 778, and upon selection of a notification, alert, and/or alarm, the MMA may cause a screen to appear indicating additional details of the alarm, notification, and/or alert, such as the time, actions to take, recommendations, etc. Where the notifications, alerts, and/or alarms in the list 1601 span beyond the display area of the analyte monitoring device 741, the MMA may configure the GUI 778 to allow a user 715 to navigate through the list 1601 using a gesture, such as a scroll or flick, recognized by GUI 778 and/or provide a selectable date option 1603 to allow a user 715 to jump to a different date of notifications, alarms, and/or alerts.

Each notification, alarm, and/or alert may correspond to a different type, severity, and/or frequency, which may be represented as a specific icon as shown in FIG. 16. For example, icon 1621 may indicate a critical alarm, icon 1623 may indicate a non-critical alert, icon 1625 may indicate a non-critical notification, icon 1627 may indicate more than one alarm in the same period, and icon 1629 may indicate a battery alarm 1629 for the transceiver 730. In some embodiments, different icons may be used to indicate the same or different types, frequency, and/or severity of alarms, alerts, and notifications as shown in the legend.

Where the MMA includes different notification, alert, and/or alarm types, such as those shown in the legend in FIG. 16, the MMA may configure the GUI 778 to depict a set of one or more selectable filtering options 1605 on the notification screen to allow a user 715 to filter the list 1601 display by types of notifications, alerts, and/or alarms. When the "all" events option is selected, all notifications, alarms, and/or alerts regardless of type may be displayed in the list 1601. However, upon the selection of a selectable notification filtering option 1605, which may be represented as one or more icons, such as those shown in the legend, only notifications, alerts, and/or alarms corresponding to the selected filtering option 1605 may be displayed in the list 1601. For example, if a user of a MMA selects the icon 1621 corresponding to critical alarms, then the MMA may only display critical alarms, if any, in the list 1601.

Table 2 below lists some non-limiting examples of the alarms, alerts, and notifications that the MMA may transmit for display on the GUI 778 of the analyte monitoring device, and responsive action(s) to take to address the alarm, alert, and/or notification.

TABLE 2

| Description of Alarm/Alert/Notification | Responsive User Action(s) |
| --- | --- |
| Low Glucose: This alarm or alert may appear when a user's glucose value is at or below a preset low glucose alarm or alert level. | Pay close attention to glucose values, symptoms, and trends. Confirm glucose value with a blood glucose meter test before making a treatment decision. |
| Out of Range Low Glucose: This alarm or alert may appear when the glucose value is lower than 40 mg/dL. No glucose value can be displayed (only a LO | Measure glucose manually by using blood glucose meter. Always confirm glucose value with a blood glucose meter test before making a treatment decision. |

TABLE 2-continued

| Description of Alarm/Alert/Notification | Responsive User Action(s) |
|---|---|
| display on the home screen in lieu of the current glucose level 1303). | Once the sensor glucose value is at or higher than 40 mg/dL, display of glucose levels 1303 will resume. |
| High Glucose Alarm/Alert: This alarm or alert may appear when the glucose value is at or above a preset high glucose alarm or alert level. | Pay close attention to glucose values, symptoms, and trends. Please confirm glucose value with a blood glucose meter test before making a treatment decision. |
| Out of Range High Glucose: This alarm or alert may appear when the glucose value is higher than 400 mg/dL. No glucose value can be displayed (only a HI display on the home screen in lieu of the current glucose level 1303). | Measure glucose manually by using blood glucose meter. Always confirm glucose value with a blood glucose meter test before making a treatment decision. Once the sensor glucose value is at or higher than 40 mg/dL, display of glucose values will resume. |
| Calibration Past Due: This alarm or alert may appear when the system is past due for calibration. No glucose value can be displayed until calibration is performed. | Perform a fingerstick calibration in order to resume displaying glucose values. |
| Calibration Expired: This alarm or alert may appear when a calibration has not been performed in 24 hours. The system is returned to initialization phase. No glucose value can be displayed until calibration is performed. | In initialization phase, a user must perform 4 fingerstick calibration tests at 2-12 hours apart. Display of glucose values may resume after the $2^{nd}$ successful fingerstick calibration test. |
| Battery Empty: This alarm or alert may appear when the transceiver/transmitter battery is empty and needs to be recharged. No glucose value can be displayed until the transceiver/transmitter is recharged. | Recharge the transceiver immediately. Remove the transceiver from body before connecting the transceiver to the power supply. |
| Sensor Replacement: This alarm or alert may appear when the sensor needs to be replaced. No glucose value can be displayed until sensor is replaced. | Contact physician to have sensor replaced. |
| High Ambient Light: This alarm or alert may appear when the transceiver is receiving too much ambient light affecting its ability to communicate with the sensor. No glucose value can be displayed until ambient light is reduced. | Reduce ambient light by considering one or more of the following: Move to area where there is less light exposure Place a dark material over the transceiver Wear the transceiver under a jacket |
| High Transmitter Temparature: This alarm or alert may appear when the transceiver's temperature is too high. No glucose value can be displayed until transceiver's temperature returns to normal operating condition. | Reduce temperature by moving to a cooler environment. Once the transceiver's temperature is below 42° C, it will resume providing glucose values. User may temporarily remove the transceiver to cool it down but must make sure to replace the transceiver back over the sensor so that it can provide glucose readings when back to normal condition. |
| Low Sensor Temperature: This alarm or alert may appear when the sensor temperature is too low. No glucose value can be displayed until sensor temperature is within normal operating condition. | Go to a warmer environment to increase the temperature. Keep transceiver on so you user will start receiving glucose value when the temperature is between 27-40° C. |
| High Sensor Temperature: This alarm or alert may appear when the sensor temperature is too high. No glucose value can be displayed until sensor temperature is within normal operating condition. | Go to a cooler environment to reduce the temperature. Keep transceiver on so user may start receiving glucose value when the temperature is between 27-40° C. |
| Transmitter Error: This alarm or alert may appear when the system's internal checks detects a transceiver error. No glucose value can be displayed until the error is corrected. | Contact system provider immediately to resolve the issue. |
| Sensor Instability: This alarm or alert may appear when the system internal checks detects instability with the sensor which requires a return to calibration initialization phase. | In initialization phase, a user must perform 4 fingerstick calibration tests at 2-12 hours apart. Display of glucose values may resume after the $2^{nd}$ successful fingerstick calibration test. |
| Predicted Low Glucose: This alarm or alert may appear when the glucose value is strending low and will reach a Low Glucose Alarm or Alert value within a preset predictive alert amount of time. | Pay close attention to glucose values, symptoms, and trends. Please confirm glucose value with a blood glucose meter test before making a treatment decision. |
| Predicted High Glucose: This alarm or alert may appear when the glucose value is trending low and may reach a High Glucose Alarm or | Pay close attention to glucose values, symptoms, and trends. Please confirm glucose value with a blood glucose meter test before |

TABLE 2-continued

| Description of Alarm/Alert/Notification | Responsive User Action(s) |
|---|---|
| Alert value within a preset predictive alert amount of time. | making a treatment decision. |
| Rate Falling: This alert may appear when the glucose value is falling with a rate equal to or faster than a preset rate of change setting. | Pay close attention to glucose values, symptoms, and trends. Please confirm glucose value with a blood glucose meter test before making a treatment decision. |
| Rate Rising: This alert may appear when the glucose value is rising with a rate equal to or faster than a preset rate of change setting. | Pay close attention to glucose values, symptoms, and trends. Please confirm glucose value with a blood glucose meter test before making a treatment decision. |
| Calibrate Now: This notification may appear when it's time to calibrate. | Do a fingerstick blood glucose test and enter the reading as the calibration value. Do not use an alternate site (such as forearm) to obtain a blood glucose reading. |
| Charge Transmitter: This alert may appear when the transceiver battery is very low and will need to be charged very soon. | Please recharge the transceiver now. |
| New Sensor Detected: This notification may appear when the transceiver detects a new sensor not previously linked to the transceiver. The inserted sensor and the transceiver must be linked together to begin communication. | Go through the linking/sensor insertion process. The new sensor may need to acclimate to a patient's body's response. Please wait 24 hours before wearing the smart transmitter over the sensor and begin the calibration initialization phase. |
| Sensor Days: This notification may appear 30, 21, 14, 7, 6, 5, 4, 3, 2, and 1 day(s) before a sensor has completed its 90 day term to serve as a reminder to schedule a sensor removal and replacement with a physician. | Contact physician to schedule the removal and replacement of sensor. |
| Invalid Transmitter Time: This notification may appear when the MMA detects a different time with the transceiver time. | The MMA may adjust the transceiver to the current date and time based on the mobile device setting. Smart transceiver is preferentially charged daily to prevent the occurrence of an invalid date/time. |
| Temporary Profile Duration Ended: This notification may appear when the MMA detects that a duration time for a temporary profile has ended. | Temp Profile Off - a temporary profile duration has ended, and the MMA will resume using standard glucose settings. The user may select an "OK" or "Temp Profile" selectable option from this notification. |
| Basal Rate Testing: This notification may appear when the MMA detects conditions that would be appropriate for basal rate testing (for example, no carbs for X hours after last bolus, glucose values have been in a certain range and for a certain duration). | Basal Rate Test - User's glucose has been between X and X for the past X hrs. X mins since user's last recorded bolus. The user may select an "OK" or "Start Now" selectable option from this notification. |

In some embodiments where the transceiver has one or more user interfaces 778, such as a vibratory interface, LED light, button, or the like, the transceiver 730 may also provide one or more vibratory or visual alarms or alerts to indicate, for example, when a glucose alarm or alert level has been reached. The MMA may in turn cause the GUI 778 of the analyte monitoring device 741 to display the alarms, alerts, and/or messages on the home screen of the MMA. Table 3 below describes some non-limiting example vibration patterns from the transceiver 730 and/or the analyte monitoring device 741, as well as a corresponding display pattern on the MMA home screen on the analyte monitoring device 741.

TABLE 3

| Alarm or Alert Types | Transceiver and/ or Analyte Moni- toring Device Vibration Pattern | Mobile Device Display Pattern |
|---|---|---|
| Critical: No glucose values can be displayed-related alarms/alerts Requires immediate and appropriate action | 3 long beeps | Appears in RED |
| Critical: Low readings-related alarms/alerts: Low Glucose Alarm, Projected Low Glucose Alarm, Out-of-Range Low Requires immediate and appropriate action | 3 short beeps | Appears in RED |
| Critical: High readings-related alarms/alerts: High Glucose Alarm, Projected High Glucose Alarm, Out-of-Range High Requires immediate and appropriate action | 1 long then 2 short beeps | Appears in RED |
| Non-Critical Alerts/Alarms Requires some action but may not be as critical in nature | 1 short beep | Appears in YELLOW |
| Non-Critical Notifications Requires some actions but not critical inn ature | 1 short beep | Appears in BLUE |

The vibration and display patterns are not limited to the foregoing examples. For example, fast vibrations for high glucose and/or slower vibrations for low glucose may be used. The higher or lower frequency can be either vibration frequency or vibration pulses.

MMA Menu Navigational Bar

Figure 17:
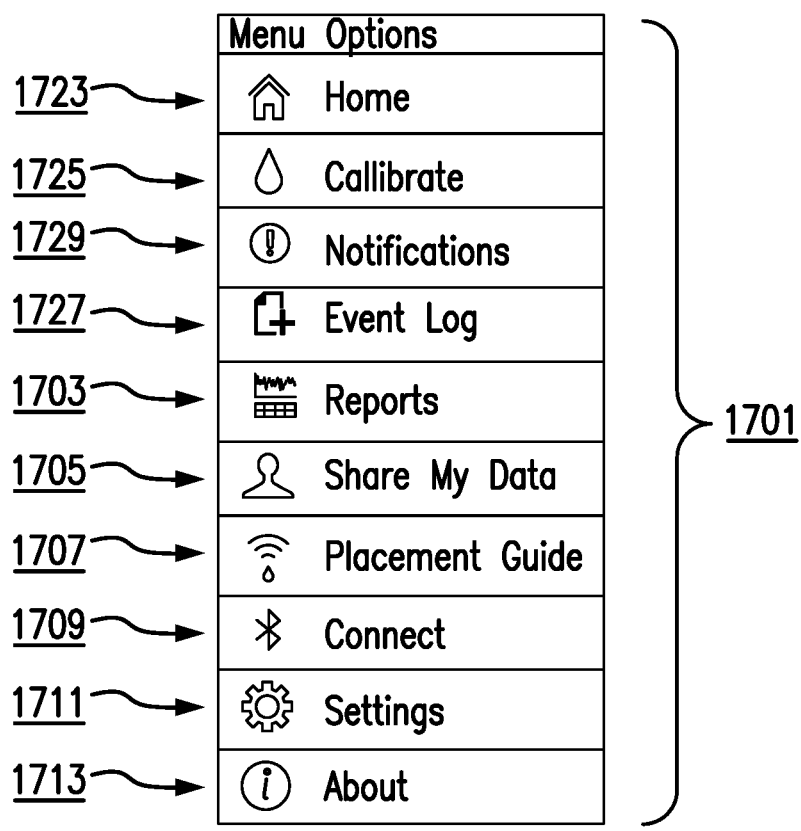
FIG. 17 is an example menu navigational bar screen display of a medical mobile application in accordance with aspects of various embodiments of the present invention.

FIG. 17 is an example menu navigational bar screen display of a medical mobile application in accordance with aspects of various embodiments of the present invention. As described above, in some embodiments the MMA home screen may include interactive navigational tools including a menu navigational bar 1329 with a selectable menu option 1331. Additionally, or in the alternative, a selectable menu option 1331 may persist in specific location across multiple screens generated by the MMA and displayed in the GUI 778, such as in the top left corner of the display or another location. On selection of the selectable menu option 1331 by a user 715, a menu bar 1701 of one or more selectable options may be displayed by the MMA on the GUI 778. For example, as shown in FIG. 17, the one or more selectable options may correspond to a home or home screen 1723 (e.g., as shown in FIGS. 13 and 14F), a calibrate screen 1725 (e.g., as shown in FIG. 14B), a notification screen 1729 (e.g., as shown in FIG. 16), an event screen 1727 (e.g., as shown in FIG. 16), a reports screen 1603, a share my data screen 1705, a placement guide 1707, a connect screen 1609, a settings screen 1711, and an about screen 1713. In response to a selection of one of the selectable options in menu bar 1601, the MMA may display one or more screens associated with the selectable options.

As described above, the home screen corresponding to selectable option 1723 may be a main screen with glucose information for a patient 710, including current glucose level, trends, status, and/or graph information. The calibrate screen corresponding to selectable option 1725 may be a screen where a user 715 can submit a calibration BGM measurement value. The notification screen corresponding to selectable option 1729 may correspond to a display of a list of past notifications, alerts, and alarms. The event log screen corresponding to selectable option 1727 may correspond to a display of a list of events such as meals, insulin, and exercise, of a patient 710 and provide an option for a user 715 to submit a new event.

In some embodiments, the reports selectable option 1723 may cause the MMA to configure the GUI 778 to display one or more screens that allow a user 715 to view pre-formatted reports based on glucose data. In some embodiments, one or more of the following types of reports may be selected by the MMA and/or a user 715 to be displayed: a weekly summary report with a seven-day summary graph and statistics; a modal day with a graphical view of continuous glucose readings over several days displayed in a 24-hour timeline; statistics; glucose distribution; and a logbook.

In some embodiments, the share my data selectable option 1705 may cause the MMA to display one or more screens that allow a user 715 to share reports and other information with others via email or to another analyte monitoring device 742 . . . 749. In some embodiments, the MMA may include a "share my data" setting that enable or disable sharing of patient information 710 with other individuals. For example, the MMA may maintain a list of one or more members with whom data may be shared and their associated contact information, such as email addresses, telephone number, social media account. If the "share my data" setting is enabled, the MMA may cause the analyte monitoring device 741 to transmit shared information over a wireless and/or wired communication link 755 using, for example, one or more simple mail transfer protocol (SMTP) messages, short message service (SMS) messages, social media (e.g., Twitter) messages, enhanced messaging service (EMS) messages, or telephonic messages. For example, the MMA may cause the monitoring device 741 to transmit shared information via one or more SMTP messages to the email addresses corresponding to the list of members. In some embodiments, members may include one or more of a caregiver, physician, or family member. In some embodiments, the MMA may allow the sharing of glucose reports with up to five people, or more. In some embodiments, the MMA may allow a user 715 to share CGM data, such as glucose and trend graph and/or CGM notifications, alerts, and alarms as described above.

Referring back to FIG. 17, in some embodiments, the placement guide selectable option 1707 may cause the MMA to display one or more screens in the GUI 778 that allow a user to see signal strength between the sensor and the transceiver as described above in connection with FIG. 10 and below in connection with FIGS. 19A-B. It may be recommended to have a signal strength at or above a predetermined amount, such as a "Good" or "Excellent" signal, and a user 715/patient 710 may reposition the transceiver 730 over the sensor 720 until the predetermined signal strength level is attained. In some embodiments, the connect selectable option 1709 may cause the MMA to display one or more screens in the GUI 778 that show a status of a communication link 725 between the transceiver 730 and the analyte monitoring device 741, as described below in connection with FIGS. 19A-B.

In some embodiments, the settings selectable option 1711 may cause the MMA to display one or more screens in the GUI 778 that allow a user to customize settings such as alarms, alerts, calibration schedule, and system information. In some embodiments, customization of the settings may better help create a glucose profile that fits a patient's 710 needs. There may be four areas where the MMA may provide customization, including: 1) glucose settings—glucose levels and rates that will set an alarm or alert (audible or vibratory) once the level or rate is crossed; 2) daily calibration settings—the morning and afternoon calibration reminder in the daily calibration phase; 3) system settings—identifies or sets various system-related information; and 4) mealtimes settings—designated times for meals so as to format glucose reports Glucose Settings In some embodiments, the CGM system may be designed to provide alarms and/or alerts to a user via one or more user interfaces coupled to the transceiver 730 and/or the analyte monitoring device 741 when a user's glucose level has reached preset levels. A user 715 may customize the glucose alarms, alerts targets, and/or rates of change values, for example, based on input from a healthcare provider. In some embodiments, a user 715 may be able to set one or more profiles with customized fields, such as, for example, glucose alarms, alerts, targets, and rates of change values. Additionally, in some embodiments, a user 715 may be able to set a temporary profile that will only be applicable for a specified duration of time. Examples of conditions and situations that might be appropriate for different or temporary profiles include but are not limited to Work Day, Weekend, Shift Work variations, Illness, Vacation, Exercise variations (running versus gardening, etc.), Post-Exercise, Menstruation, Nighttime, Daytime, etc.

In some embodiments, low and high glucose alarms or alerts may cause the MMA to generate an alarm or alert when the current glucose level has crossed a certain low or high threshold value. In some embodiments, the transceiver 730 may issue a vibratory alarm or alert and the MMA may display an alarm/alert message on the home screen of the MMA to alert when a high or low glucose value is reached. For example, by default the MMA may set a high glucose alarm or alert threshold at 200 mg/dL and a low glucose alarm or alert threshold at 70 mg/dL, and the MMA may allow a user to adjust the low glucose alarm or alert threshold to be between 60-100 mg/dL and the high glucose alarm or alert threshold to be between 150-350 mg/dL. However, it should be appreciated that the high glucose alarm or alert threshold and the low glucose alarm or alert threshold may be set at different ranges. In some embodiments, a user of the MMA may not disable the low and high glucose alarms and/or alerts.

In contrast, high and low glucose targets are displayed on the reports and line graph to show how glucose levels have been performing as compared to set targets. For example, the glucose target levels may be the high and low target level a user may be aiming for glucose levels throughout the day. In some embodiments, the default target glucose levels may be low: 80 mg/dL and high: 140 mg/dL, and the MMA may allow a user 715 to adjust the low target glucose level to be between 80-105 mg/dL and the high target glucose level to be between 140-180 mg/dL. In some embodiments, a user 715 of the MMA may not disable the low and high glucose targets.

In some embodiments, the MMA may provide a predictive alarm or alert that issues a notification to the GUI 778 in advance of an event that is likely to occur if current glucose level trends continue. Predictive alarms or alerts may use high and low glucose alarm or alert thresholds to provide the early warning, and the notification time may be set at, for example, 10, 20, 30, or 45 minutes prior to crossing the glucose alarm or alert threshold. In some embodiments, a user 715 of the MMA may disable the predictive alarms or alerts in their entirety.

In some embodiments, the MMA may provide a rate of change alarm or alert that issues a notification when the glucose level is changing (i.e., rising or falling) faster than a set glucose alarm or alert rate. In some embodiments, the MMA may by default not enable rate of change alarms and/or alerts, and a user 715 can configure a rate of change alarm and/or alert by specifying a rate of change between 1.0-5.0 mg/dL per minute. In some embodiments, a user 715 may disable the rate of change alarms or alerts in their entirety. In some embodiments, when a rate of change exceeds the specified rate of change alarm or alert value, the transceiver 730 may issue a vibratory alarm or alert and the MMA may initiate and display a rate of change alarm or alert on the analyte monitoring device 741.

Daily Calibration Settings

As described above, in the daily calibration phase the CGM system may require two daily calibrations. In some embodiments, the first and second calibration times must be between 10 and 14 hours apart. The MMA may allow a user 715 to set the daily calibration times, such as a morning calibration time and an evening calibration time. When the morning or evening calibration time occurs, the MMA may issue a notification for calibration as described above. In some embodiments, different sounds or vibration patterns associated with the calibration notification may be initiated depending on whether it is daytime or nighttime. In some embodiments, a user may calibrate up to two hours before and one hour after a set calibration time. However, in other embodiments, in the daily calibration phase the CGM system may instead require one or more daily calibrations, and the embodiments disclosed herein should not be limited to two required daily calibrations.

Systems Information Settings

In some embodiments, the MMA may provide one or more system parameters that may be viewed and/or modified and set by a user 715, such as: glucose units—unit of measurement of glucose readings; name—name of the transceiver 730; linked sensor—the sensor identity of the sensor communicating with the transceiver 730; do not disturb—places the transceiver 730 in a do not disturb mode. For example, the do not disturb setting may be set by a user to "OFF," where the MMA will provide all set alarms or alerts, or "ON," where the MMA will not provide notifications for certain alarms or alerts, such as non-critical alarms or alerts. In some embodiments, the do not disturb setting may support different interaction based on the time of day.

Mealtimes Settings

In some embodiments, the MMA may provide default time intervals for regular hours of Breakfast, Lunch, Snack, Dinner, and Sleep events. In some embodiments, a user 715 may adjust these default time intervals for Breakfast, Lunch, Snack, Dinner, and/or Sleep events. In some embodiments, the time intervals corresponding to the meal times and sleep time may be utilized on a reports graph to indicate the high, low, and average sensor glucose values during each event.

In some embodiments, the about selectable option 1713 may cause the MMA to display in the GUI 778 one or more screens that allow a user 715 to review information related to the CGM system version and identifiers. In some embodiments, the "about" screen may provide a frequently asked questions (FAQ) section that provides answers to most commonly asked questions as well as a digital copy of a user guide.

In some embodiments, the MMA may enable software upgrades of the transmitter. For example, device 240 executing the MMA may obtain a new firmware image from a server over a connection, such as a Wi-Fi_33 connection. The MMA may then cause the device 240 to send a command to the transceiver over a connection, such as a Bluetooth, with a first segment of the firmware image (e.g., segment 0). The transceiver may in turn erase its serial flash drive or other local memory and write the first segment (segment 0) of data to the serial flash drive. The MMA may cause each subsequent segment (e.g., segment 0 . . . segment n) of the firmware image to be serially sent by the device 240 to the transceiver using a command. The user 715 may initiate a "Request Update" command from the MMA to the transceiver, where the payload of the command includes an expected CRC bit and a size of the firmware image. In response to the request update command, the transceiver may verify that the firmware image stored in its local memory, such as a serial flash drive, has the correct size and CRC. Upon verification of the firmware image, the transceiver may reset itself to jump to a bootloader application that may confirm that a new firmware image is ready to be installed. Upon confirmation, the transceiver bootloader application may copy the firmware image from a serial flash drive to program memory. After copying, the transceiver may jump to the application firmware. Next, the application firmware of the transceiver may verify the CRC of the firmware image.

Figure 18:
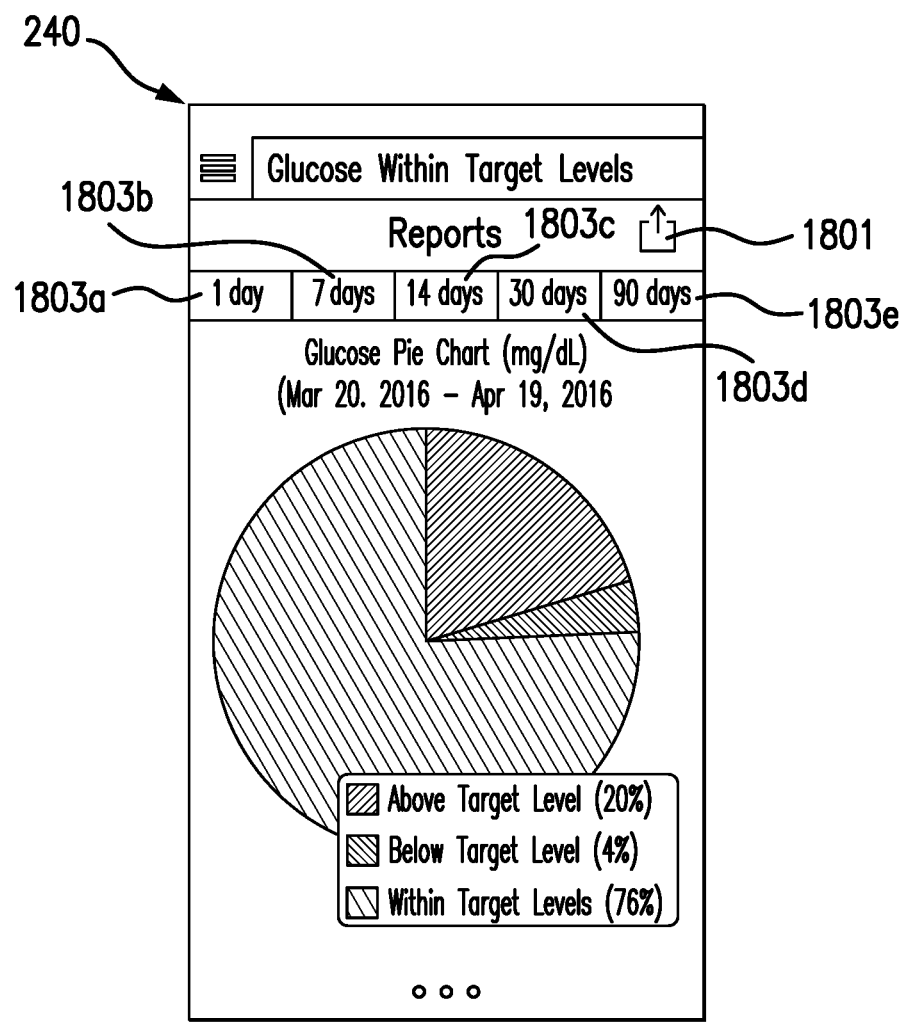
FIG. 18 is an example report screen display of a medical mobile application in accordance with aspects of various embodiments of the present invention.

FIG. 18 is an example report screen display of a medical mobile application in accordance with aspects of various embodiments of the present invention. As shown in FIG. 18, the report screen may be displayed by the MMA on device 240 and may comprise a pie chart or other graphical representation of categories or ranges of analyte values, such as glucose values, over a specific time interval. For example, the pie chart of FIG. 18 depicts a measure of the percentage of time for which glucose values were above a target level, below a target level, or within a target level. A user 715 may customize the categories or ranges of analyte values displayed in the report to include additional or alternative categories or ranges of analyte values, such as, for example, glucose values above an alarm value, glucose values below an alarm value, glucose values between alarm level, and the like.

In some embodiments, the reports screen may further include one or more selectable time interval options 1803*a-e* that enable a user 715 to adjust the relevant time period for the report. For example, selectable time interval options may include 1 day 1803*a*, 7 days 1803*b*, 14 days 1803*c*, 30 days 1803*d*, and 90 days 1803*e*; however, the embodiments disclosed herein are not limited to these specific time interval options.

In some embodiments, the reports screen may further include a single tap electronic communication icon 1801. In response to receiving a selection of the electronic communication icon 1801, the MMA may automatically open and attach the displayed report in an electronic communication, such as, for example and without limitation, an email message (e.g., an SMTP message), a text message (e.g., an SMS message), a social media (e.g., Twitter) message, an EMS message, or a telephonic message. In some embodiments, in response to receiving a selection of the electronic communication icon 1801, the MMA may automatically transmit the displayed report in an electronic communication to a recipient.

FIG. 18 depicts a non-limiting example of a reports screen, and additional reports relating to analyte measurements may be generated and displayed, such as, for example, a glucose modal summary, a pie chart, a plot, and the like. In some embodiments, reports may be generated and displayed that include non-analyte related data over time, such as compliance of CGM wear, which may depicted as CGM wear over time in one or more of a line graph, a pie chart, a plot, and the like. In embodiments where multiple reports may be generated, the GUI 778 may enable one or more navigational tools to allow a user 715 to navigate between different reports, such as, for example, one or more interactive user interface elements (e.g., a selectable icon) and/or gesture recognition (e.g., swipe, flick, scroll, and the like).

Figure 19B:
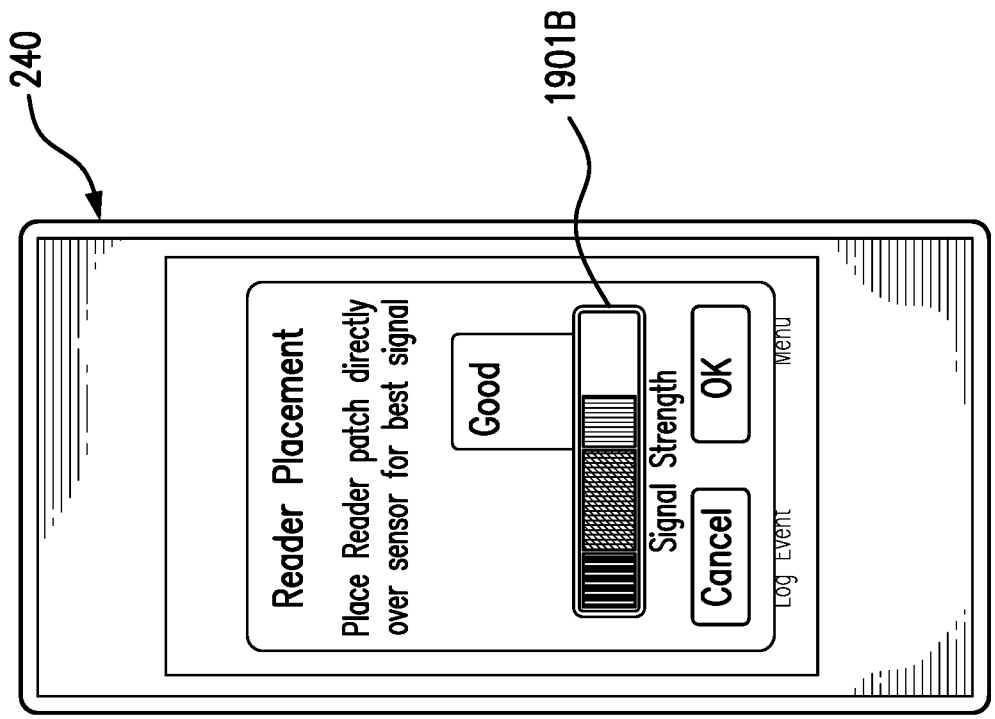
FIGS. 19A-B are example placement screen displays of a medical mobile application in accordance with aspects of various embodiments of the present invention.
Figure 19A:
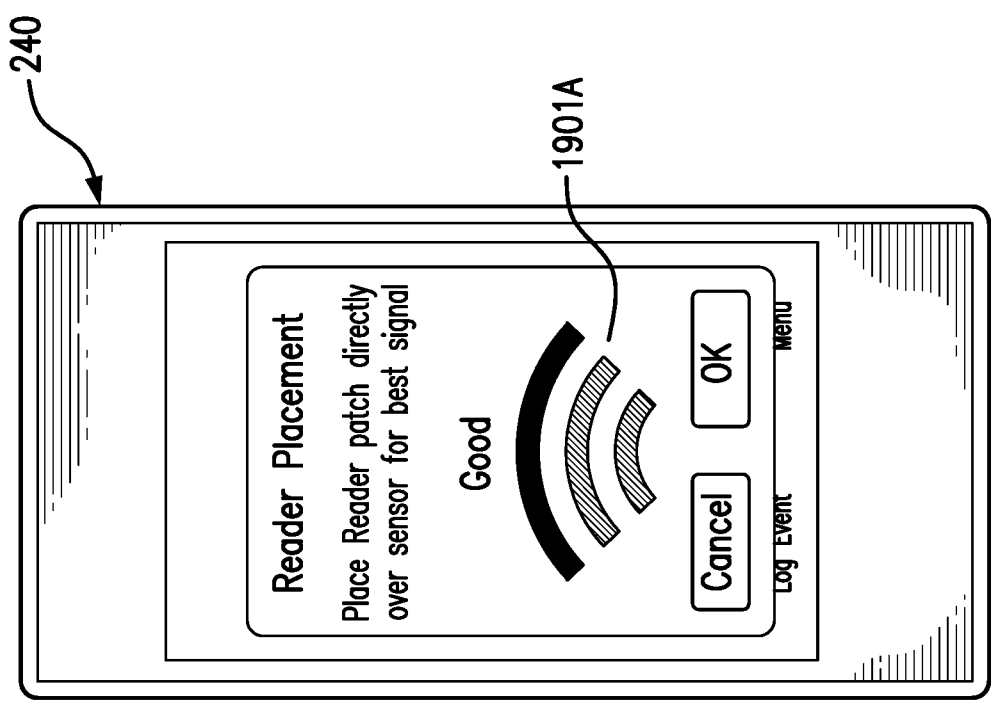

FIGS. 19A-B are example placement screen displays of a medical mobile application in accordance with aspects of various embodiments of the present invention. As described above, the MMA may display one or more screens in the GUI 778 on device 240 that allow a user to see signal strength between the sensor/reader and the transceiver. In some embodiments, a measure of the signal strength between the sensor and the transceiver may be updated in real time or near real time using one or more dynamic graphical icons 1901A-B. The placement guide thus may provide real time or near real time feedback to help enable a user 715 to correctly align the transceiver over the sensor, or simply to locate the sensor using a transceiver or other device.

FIG. 19A depicts an example dynamic graphical icon 1901A that comprises a series of vertically aligned bars that may be lit up or changed color based on received signal strength measurements. For example, fewer bars may be lit up and/or changed color when signal strength is weak, and more bars may be lit up and/or changed color when signal strength is strong. FIG. 19B depicts an alternative or additional example dynamic graphical icon 1901B that comprises a series of horizontally aligned bars that may displayed and/or changed colors based on received signal strength measurements. For example, when signal strength is weak, dynamic graphical icon 1901B may depict very few bars, which may be displayed in a first color (e.g., red). When signal strength is moderate, dynamic graphical icon 1901B may depict additional bars, some of which may be displayed in a second color (e.g., yellow). Additionally, when signal strength is good or strong, dynamic graphical icon 1901B may depict additional bars, some of which may be displayed in a third color (e.g., green). However, the placement guide is not limited to the examples shown in FIGS. 19A-B, and additional colors, icons, graphics, or text may be displayed and updated in real time or near real time to indicate signal strength.

FIGS. 20A-B are an example home screen displays in portrait and landscape mode of a medical mobile application in accordance with aspects of various embodiments of the present invention. In some embodiments, the home screen may switch from portrait mode to landscape mode automatically or selectively where device 240 supports a portrait and landscape display mode.

For example, FIG. 20A shows an example home screen displayed by the MMA on device 240 in portrait mode. The home screen may comprise a plurality of information items, such as for example, a trend arrow 2007, a historical graph, such as a line graph 2009A, a boundary or indication of a high glucose alarm level 2013A, a low glucose alarm level 2015A, a high glucose target level 2017A, and a low glucose target level 2019A, as described herein. In order to selectively switch to a landscape display mode from a portrait display mode, a user 715 may select an icon, such as icon 2050.

As another example, FIG. 20B depicts an example home screen display in landscape mode displayed by the MMA on device 240. As shown in FIG. 20B, the landscape mode display may also comprise a plurality of information items, which may be the same or different than the information items shown on the home screen in portrait mode. For example, FIG. 20B depicts the historical graph, such as line graph 2009B, a boundary or indication of a high glucose alarm level 2013B, a low glucose alarm level 2015B, a high glucose target level 2017B, and a low glucose target level 2019B, as described herein. In some embodiments, the landscape mode display may comprise a plurality of predetermined selectable date range options 2070, such as, for example, 1, 7, 14, 30, and/or 90 days.

In some embodiments, the landscape mode display may comprise a single-tap electronic communication icon 2060 that enables a user 715 to cause the MMA to transmit the displayed historical graph 2009B in an electronic communication, such as, for example and without limitation, an email message (e.g., an SMTP message) to one or more email addresses, a text message to one or more telephone numbers (e.g., an SMS message), a social media (e.g., Twitter) message, an EMS message, or a telephonic message. For example, upon selection of the selectable single-tap electronic communication icon 2060, the MMA may automatically open and attach a displayed report or graph to an electronic communication.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In this specification, "a" and "an" and similar phrases are to be interpreted as "at least one" and "one or more." References to "an" embodiment in this disclosure are not necessarily to the same embodiment.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element) or a combination thereof, all of which are behaviorally equivalent. For example, modules may be implemented using computer hardware in combination with software routine(s) written in a computer language (such as C, C++, Fortran, Java, Basic, Matlab or the like) or a modeling/simulation program such as Simulink, Stateflow, GNU Octave, or LabVIEW MathScript. In some embodiments, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation has focused on the example(s) a wireless analyte monitoring system. However, one skilled in the art will recognize that embodiments of the invention could be employed for devices other than just for analyte monitoring such as for nerve monitoring devices, blood flow devices, digestive monitoring devices, combinations thereof, and/or the like.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

What is claimed is:

1. A non-transitory tangible computer readable medium comprising computer readable instructions configured to cause one or more processors in an analyte monitoring device to perform a process comprising:
   receiving first analyte data over a communications link from at least one first device;
   determining whether or not calibration measurement entry is appropriate;
   in response to determining that calibration measurement entry is appropriate, configuring a graphical user interface on a display of the analyte monitoring device to allow calibration measurement entry;
   in response to determining that calibration measurement entry is not appropriate, configuring the graphical user interface on the display of the analyte monitoring device to prevent calibration measurement entry;
   receiving an entered calibration measurement from the graphical user interface on the display of the analyte monitoring device; and
   using a communications interface of the analyte monitoring device to transmit the entered calibration measurement over the communications link to the at least one first device.

2. The medium according to claim 1, wherein the received first analyte data is based on measurements obtained from an analyte monitoring sensor.

3. The medium according to claim 1, wherein the computer readable instructions are further configured to cause the one or more processors in the analyte monitoring device to receive the first analyte data wirelessly.

4. The medium according to claim 1, wherein receiving the entered calibration measurement comprises accepting manual data input via the graphical user interface on the display of the analyte monitoring device.

5. The medium according to claim 1, wherein the entered calibration measurement is a finger-stick blood glucose measurement.

6. The medium according to claim 1, wherein the at least one first device comprises at least one of: an analyte monitoring sensor, an intermediary device, and a data repeating device.

7. The medium according to claim 1, wherein the computer readable instructions are further configured to cause the one or more processors in the analyte monitoring device to display on the graphical user interface one or more of: a next scheduled calibration time, a number of calibrations completed, and a calibration phase.

8. The medium of claim 1, wherein configuring the graphical user interface on the display to prevent calibration measurement entry comprises configuring the graphical user interface on the display to disable a selectable option for calibration measurement submission.

9. The medium of claim 1, wherein determining whether or not calibration measurement entry is appropriate comprises determining whether or not a user has worn the at least one first device for at least a threshold period of time, and calibration measurement entry is determined to be not appropriate if the user was determined to not have worn the at least one first device for at least the threshold period of time.

10. The medium of claim 1, wherein determining whether or not calibration measurement entry is appropriate comprises (i) receiving an entry of a time at which a blood glucose measurement was taken and (ii) determining whether or not the time at which the blood glucose measurement was taken is more than a threshold period of time prior to entry of the time at which the blood glucose measurement was taken, and calibration measurement entry is determined to be not appropriate if the blood glucose measurement was determined to have been taken more than the threshold period of time prior to entry of the time at which the blood glucose measurement was taken.

11. The medium of claim 1, wherein determining whether or not calibration measurement entry is appropriate comprises two or more of (i) determining or not whether a current time is within a calibration window, (ii) determining or not whether a user has worn the at least one first device for at least a first threshold period of time, (iii) determining whether or not a blood glucose measurement was taken more than a second threshold period of time prior to the current time, and (iv) determining whether or not analyte values are changing faster than a threshold rate; and
    calibration measurement entry is determined to be not appropriate if the current time was determined to not be within the calibration window, the user was determined to not have worn the at least one first device for at least the first threshold period of time, the blood glucose measurement is determined to have been taken more than the second threshold period of time prior to the current time, or the analyte values were determined to be changing faster than the threshold rate.

12. The medium of claim 1, wherein determining whether or not calibration measurement entry is appropriate comprises three or more of (i) determining whether or not a current time is within a calibration window, (ii) determining whether or not a user has worn the at least one first device for at least a first threshold period of time, (iii) determining whether or not a blood glucose measurement was taken more than a second threshold period of time prior to the current time, and (iv) determining whether or not analyte values are changing faster than a threshold rate; and
    calibration measurement entry is determined to be not appropriate if the current time is determined to not be within the calibration window, the user was determined to not have worn the at least one first device for at least the first threshold period of time, the blood glucose measurement was determined to have been taken more than the second threshold period of time prior to the current time, or the analyte values were determined to be changing faster than the threshold rate.

13. The medium of claim 1, wherein determining whether or not calibration measurement entry is appropriate comprises (i) determining whether or not a current time is within a calibration window, (ii) determining whether or not a user has worn the at least one first device for at least a first threshold period of time, (iii) determining whether or not a blood glucose measurement was taken more than a second threshold period of time prior to the current time, and (iv) determining whether or not analyte values are changing faster than a threshold rate; and
    calibration measurement entry is determined to be not appropriate if the current time is determined to not be within the calibration window, the user was determined to not have worn the at least one first device for at least the first threshold period of time, the blood glucose measurement was determined to have been taken more than the second threshold period of time prior to the current time, or the analyte values were determined to be changing faster than the threshold rate.

14. The medium of claim 1, wherein determining whether or not calibration measurement entry is appropriate comprises determining whether or not a current time is within a calibration window, and calibration measurement entry is determined to be not appropriate if the current time was determined to not be within the calibration window.

15. The medium of claim 14, wherein the calibration window is one hour before to two hours after a scheduled calibration.

16. The medium of claim 1, wherein determining whether or not calibration measurement entry is appropriate comprises determining whether or not analyte values are changing faster than a threshold rate, and calibration measurement entry is determined to be not appropriate if the analyte values were determined to be changing faster than the threshold rate.

17. The medium of claim 16, wherein the threshold rate is 2.5 mg/dL/min.

18. The medium of claim 1, wherein the process further comprises:
    receiving an entered calibration measurement from the graphical user interface on the display of the analyte monitoring device; and
    determining whether to reject the entered calibration measurement.

19. The medium of claim 18, wherein determining whether or not to reject the entered calibration measurement comprises determining whether or not the entered calibration measurement is less than or equal to a first threshold level and determining whether or not the entered calibration measurement is greater than or equal to a second threshold level, which is different than the first level threshold; and
    the process further comprises rejecting the entered calibration if the entered calibration measurement was determined to be less than or equal to the first threshold level or if the entered calibration measurement was determined to be greater than or equal to the second threshold level.

20. The medium of claim 19, wherein the first threshold level is 40 mg/Dl, and the second threshold level is 400 mg/dL.

21. The medium according to claim 1, wherein the process further comprises:
    determining a first quality factor for the first analyte data;
    using a communications interface of the analyte monitoring device to receive second analyte data from the at least one first device;
    determining a second quality factor for the second analyte data;
    determining whether both the first quality factor and the second quality factor exceed a threshold; and
    if both the first quality factor and the second quality factor exceed the threshold, employing the first analyte data and the second analyte data to determine calibration data.

22. The medium according to claim 21, wherein determining at least one of the first quality factor and the second quality factor comprises determining the rate of change with respect to earlier analyte data measurements.

23. The medium according to claim 21, wherein determining at least one of the first quality factor and the second quality factor comprises accounting for the time of the last calibration.

24. The medium according to claim 21, wherein determining at least one of the first quality factor and the second quality factor comprises accounting for the amount of analyte data collected.

25. The medium according to claim 21, wherein determining at least one of the first quality factor and the second quality factor comprises verifying that the first analyte data falls within an operating range.

26. The medium according to claim 21, wherein determining at least one of the first quality factor and the second quality factor comprises accounting for the operating conditions when the analyte data was collected.

27. The medium according to claim 21, wherein determining at least one of the first quality factor and the second quality factor comprises accounting for statistical changes from previous measurements.

28. A process performed by an analyte monitoring device, the process comprising:
    receiving first analyte data over a communications link from at least one first device;

at a first time, determining that calibration measurement entry is not appropriate;

in response to determining that calibration measurement entry is not appropriate at the first time, configuring a graphical user interface on a display of the analyte monitoring device to prevent calibration measurement entry;

at a second time that is different than the first time, determining that calibration measurement entry is appropriate;

in response to determining that calibration measurement entry is appropriate at the second time, configuring the graphical user interface on the display of the analyte monitoring device to allow calibration measurement entry;

receiving an entered calibration measurement from the graphical user interface on the display of the analyte monitoring device; and using a communications interface of the analyte monitoring device to transmit the entered calibration measurement over the communications link to the first device.

29. The process of claim 28, wherein the received first analyte data is based on measurements obtained from an analyte monitoring sensor.

30. The process of claim 28, wherein receiving the first analyte data comprises receiving the first analyte data wirelessly.

31. The process according to claim 28, wherein receiving the entered calibration measurement comprises accepting manual data input via the graphical user interface on the display.

32. The process according to claim 28, wherein the entered calibration measurement is a finger-stick blood glucose measurement.

33. The process according to claim 28, wherein the at least one first device comprises at least one of: an analyte monitoring sensor, an intermediary device, and a data repeating device.

34. The process according to claim 28, wherein the process further comprises configuring the graphical user interface to display one or more of: a next scheduled calibration time, a number of calibrations completed, and a calibration phase.

35. The process of claim 28, wherein configuring the graphical user interface on the display to prevent calibration measurement entry comprises configuring the graphical user interface on the display to disable a selectable option for calibration measurement submission.

36. The process of claim 28, wherein determining that calibration measurement entry is not appropriate comprises determining that a user has worn the at least one first device for less than a threshold period of time.

37. The process of claim 28, wherein determining that calibration measurement entry is not appropriate comprises determining that a blood glucose measurement was taken more than a threshold period of time prior to a current time.

38. The process of claim 28, wherein determining that calibration measurement entry is not appropriate comprises determining that a current time is not within a calibration window.

39. The process of claim 38, wherein the calibration window is one hour before to two hours after a scheduled calibration.

40. The process of claim 28, wherein determining that calibration measurement entry is not appropriate comprises determining that analyte values are changing faster than a threshold rate.

41. The process of claim 40, wherein the threshold rate is 2.5 mg/dL/min.

42. The process of claim 28, further comprising:
receiving an entered calibration measurement from the graphical user interface on the display of the analyte monitoring device; and
determining whether or not to reject the entered calibration measurement.

43. The process of claim 42, wherein determining whether or not to reject the entered calibration measurement comprises determining whether or not the entered calibration measurement is less than or equal to a first threshold level and determining whether or not the entered calibration measurement is greater than or equal to a second threshold level, which is different than the first level threshold; and
the process further comprises rejecting the entered calibration if the entered calibration measurement was determined to be less than or equal to the first threshold level or if the entered calibration measurement was determined to be greater than or equal to the second threshold level.

44. The process of claim 43, wherein the first threshold level is 40 mg/Dl, and the second threshold level is 400 mg/dL.

45. The process according to claim 28, further comprising:
determining a first quality factor for the first analyte data;
receiving second analyte data over the communications link from the at least one first device;
determining a second quality factor for the second analyte data;
determining whether both the first quality factor and the second quality factor exceed a threshold; and
if both the first quality factor and the second quality factor exceed the threshold, employing the first analyte data and the second analyte data to determine calibration data.

46. The process according to claim 45, wherein determining at least one of the first quality factor and the second quality factor comprises determining the rate of change with respect to earlier analyte data measurements.

47. The process according to claim 45, wherein determining at least one of the first quality factor and the second quality factor comprises accounting for the time of the last calibration.

48. The process according to claim 45, wherein determining at least one of the first quality factor and the second quality factor comprises accounting for the amount of analyte data collected.

49. The process according to claim 45, wherein determining at least one of the first quality factor and the second quality factor comprises verifying that the first analyte data falls within an operating range.

50. The process according to claim 45, wherein determining at least one of the first quality factor and the second quality factor comprises accounting for the operating conditions when the analyte data was collected.

51. The process according to claim 45, wherein determining at least one of the first quality factor and the second quality factor comprises accounting for statistical changes from previous measurements.

52. An analyte monitoring device comprising:
a display;
one or more processors;
a communications interface; and a non-transitory tangible computer readable medium comprising computer readable instructions configured to cause the one or more processors to:
receive first analyte data over the communications interface from at least one first device;
determine whether or not calibration measurement entry is appropriate;
in response to determining that calibration measurement entry is appropriate, configure a graphical user interface on the display to allow calibration measurement entry;
in response to determining that calibration measurement entry is not appropriate, configure the graphical user interface on the display to prevent calibration measurement entry;
receive an entered calibration measurement from the graphical user interface on the display of the analyte monitoring device; and
use the communications interface to transmit the entered calibration measurement over a communications link to the first device.

53. The analyte monitoring device according to claim 52, wherein the received first analyte data is based on measurements obtained from an analyte monitoring sensor.

54. The analyte monitoring device according to claim 52, wherein the communications interface comprises a wireless communications interface.

55. The analyte monitoring device according to claim 52, wherein receiving the entered calibration measurement comprises accepting manual data input via the graphical user interface on the display.

56. The analyte monitoring device according to claim 52, wherein the entered calibration measurement is a fingerstick blood glucose measurement.

57. The analyte device according to claim 52, wherein the at least one first device comprises at least one of: a wireless analyte monitoring sensor, an intermediary device, and a data repeating device.

58. The analyte device according to claim 52, wherein the computer readable instructions are further configured to cause the one or more processors to display on the graphical user interface one or more of: a next scheduled calibration time, a number of calibrations completed, and a calibration phase.

59. The analyte monitoring device of claim 52, wherein configuring the graphical user interface on the display to prevent calibration measurement entry comprises configuring the graphical user interface on the display to disable a selectable option for calibration measurement submission.

60. The analyte monitoring device of claim 52, wherein determining whether or not calibration measurement entry is appropriate comprises determining whether or not a user has worn the at least one first device for at least a threshold period of time, and calibration measurement entry is determined to be not appropriate if the user was determined to not have worn the at least one first device for at least the threshold period of time.

61. The analyte monitoring device of claim 52, wherein determining whether or not calibration measurement entry is appropriate comprises (i) receiving an entry of a time at which a blood glucose measurement was taken and (ii) determining whether or not the time at which the blood glucose measurement was taken is more than a threshold period of time prior to entry of the time at which the blood glucose measurement was taken, and calibration measurement entry is determined to be not appropriate if the blood glucose measurement was determined to have been taken more than the threshold period of time prior to entry of the time at which the blood glucose measurement was taken.

62. The analyte monitoring device of claim 52, wherein determining whether or not calibration measurement entry is appropriate comprises determining whether or not analyte values are changing faster than a threshold rate, and calibration measurement entry is determined to be not appropriate if the analyte values were determined to be changing faster than the threshold rate.

63. The analyte monitoring device of claim 62, wherein the threshold rate is 2.5 mg/dL/min.

64. The analyte monitoring device of claim 52, wherein determining whether or not calibration measurement entry is appropriate comprises two or more of (i) determining whether or not a current time is within a calibration window, (ii) determining whether or not a user has worn the at least one first device for at least a first threshold period of time, (iii) determining whether or not a blood glucose measurement was taken more than a second threshold period of time prior to the current time, and (iv) determining whether or not analyte values are changing faster than a threshold rate; and
calibration measurement entry is determined to be not appropriate if the current time was determined to not be within the calibration window, the user was determined to not have worn the at least one first device for at least the first threshold period of time, the blood glucose measurement was determined to have been taken more than the second threshold period of time prior to the current time, or the analyte values were determined to be changing faster than the threshold rate.

65. The analyte monitoring device of claim 52, wherein determining whether or not calibration measurement entry is appropriate comprises three or more of (i) determining whether or not a current time is within a calibration window, (ii) determining whether or not a user has worn the at least one first device for at least a first threshold period of time, (iii) determining whether or not a blood glucose measurement was taken more than a second threshold period of time prior to the current time, and (iv) determining whether or not analyte values are changing faster than a threshold rate; and
calibration measurement entry is determined to be not appropriate if the current time was determined to not be within the calibration window, the user was determined to not have worn the at least one first device for at least the first threshold period of time, the blood glucose measurement was determined to have been taken more than the second threshold period of time prior to the current time, or the analyte values were determined to be changing faster than the threshold rate.

66. The analyte monitoring device of claim 52, wherein determining whether or not calibration measurement entry is appropriate comprises (i) determining whether or not a current time is within a calibration window, (ii) determining whether or not a user has worn the at least one first device for at least a first threshold period of time, (iii) determining whether or not a blood glucose measurement was taken more than a second threshold period of time prior to the current time, and (iv) determining whether or not analyte values are changing faster than a threshold rate; and
calibration measurement entry is determined to be not appropriate if the current time was determined to not be within the calibration window, the user was determined to not have worn the at least one first device for at least the first threshold period of time, the blood glucose measurement was determined to have been taken more than the second threshold period of time prior to the current time, or the analyte values were determined to be changing faster than the threshold rate.

67. The analyte monitoring device of claim 52, wherein determining whether or not calibration measurement entry is appropriate comprises determining whether or not a current time is within a calibration window, and calibration measurement entry is determined to be not appropriate if the current time was determined to not be within the calibration window.

68. The analyte monitoring device of claim 67, wherein the calibration window is one hour before to two hours after a scheduled calibration.

69. The analyte monitoring device of claim 52, wherein the computer readable instructions are further configured to cause the one or more processors to:
receive an entered calibration measurement from the graphical user interface on the display of the analyte monitoring device; and
determine whether or not to reject the entered calibration measurement.

70. The analyte monitoring device of claim 69, wherein determining whether or not to reject the entered calibration measurement comprises determining whether or not the entered calibration measurement is less than or equal to a first threshold level and determining whether or not the entered calibration measurement is greater than or equal to a second threshold level, which is different than the first level threshold; and
the computer readable instructions are further configured to cause the one or more processors to reject the entered calibration if the entered calibration measurement was determined to be less than or equal to the first threshold level or if the entered calibration measurement was determined to be greater than or equal to the second threshold level.

71. The analyte monitoring device of claim 70, wherein the first threshold level is 40 mg/Dl, and the second threshold level is 400 mg/dL.

72. The analyte monitoring device according to claim 52, wherein the computer readable instructions are further configured to cause the one or more processors to:
determine a first quality factor for the first analyte data;
use the communications interface to receive second analyte data from the at least one first device;
determine a second quality factor for the second analyte data;
determine whether both the first quality factor and the second quality factor exceed a threshold; and
if both the first quality factor and the second quality factor exceed the threshold, employ the first analyte data and the second analyte data to determine calibration data.

73. The analyte monitoring device according to claim 72, wherein determining at least one of the first quality factor and the second quality factor comprises determining the rate of change with respect to earlier analyte data measurements.

74. The analyte monitoring device according to claim 72, wherein determining at least one of the first quality factor and the second quality factor comprises accounting for the time of the last calibration.

75. The analyte monitoring device according to claim 72, wherein determining at least one of the first quality factor and the second quality factor comprises accounting for the amount of analyte data collected.

76. The analyte monitoring device according to claim 72, wherein determining at least one of the first quality factor and the second quality factor comprises verifying that the first analyte data falls within an operating range.

77. The analyte monitoring device according to claim 72, wherein determining at least one of the first quality factor and the second quality factor comprises accounting for the operating conditions when the analyte data was collected.

78. The analyte monitoring device according to claim 72, wherein determining at least one of the first quality factor and the second quality factor comprises accounting for statistical changes from previous measurements.

\* \* \* \* \*